(12) United States Patent
Wooley et al.

(10) Patent No.: US 9,545,447 B2
(45) Date of Patent: Jan. 17, 2017

(54) POLYMER-DRUG SYSTEMS

(71) Applicant: THE TEXAS A&M UNIVERSITY SYSTEM, College Station, TX (US)

(72) Inventors: Karen Wooley, College Station, TX (US); Jiong Zou, College Station, TX (US); Mahmoud El Sabahy, College Station, TX (US); Shiyi Zhang, Bryan, TX (US); Fuwu Zhang, College Station, TX (US)

(73) Assignee: The Texas A&M University System, College Station, TX (US)

( * ) Notice: Subject to any disclaimer, the term of this patent is extended or adjusted under 35 U.S.C. 154(b) by 49 days.

(21) Appl. No.: 14/043,456

(22) Filed: Oct. 1, 2013

(65) Prior Publication Data
US 2014/0193504 A1 Jul. 10, 2014

Related U.S. Application Data

(60) Provisional application No. 61/708,911, filed on Jan. 4, 2013.

(51) Int. Cl.
*A61K 47/48* (2006.01)
*A61K 47/34* (2006.01)
*A61K 31/337* (2006.01)

(52) U.S. Cl.
CPC .......... *A61K 47/34* (2013.01); *A61K 31/337* (2013.01); *A61K 47/482* (2013.01); *A61K 47/48192* (2013.01)

(58) Field of Classification Search
None
See application file for complete search history.

(56) References Cited

U.S. PATENT DOCUMENTS

| | | | |
|---|---|---|---|
| 6,537,585 B1 | 3/2003 | Dang et al. | |
| 7,345,138 B2 | 3/2008 | Wang et al. | |
| 2012/0225129 A1* | 9/2012 | Eliasof | C12N 15/87 424/499 |

FOREIGN PATENT DOCUMENTS

WO  WO 2011/143524  11/2011  ............. A61K 47/48

OTHER PUBLICATIONS

Wang, Y., et al., "Functionalized micelles from block copolymer of polyphosphoester and poly(ε-caprolactone) for receptor-mediated drug delivery," Journal of Controlled Release 128 (2008) 32-40.*
Oerlemans, C. et al., "Polymeric Micelles in Anticancer Thearpy: Targeting, Imaging, and Triggered Release," Pharm Res (2010) 27:2569-2589.*

(Continued)

*Primary Examiner* — Tracy Vivlemore
*Assistant Examiner* — Monica Shin
(74) *Attorney, Agent, or Firm* — Baker & Botts L.L.P.

(57) ABSTRACT

The present disclosure generally relates to polymer-drug systems, and more particularly to nanoscopic particles comprising amphiphilic block copolymers conjugated, physically encapsulated, or otherwise combined with chemotherapeutic agents along a selective region or regions of the backbone of the copolymer, so as to package the chemotherapeutic agent in selective domains within each nanoscopic particle, as well as to methods for making such particles, and applications and methods for using such particles, including in the formation of polymer micelles.

10 Claims, 41 Drawing Sheets
(35 of 41 Drawing Sheet(s) Filed in Color)

(56) References Cited

OTHER PUBLICATIONS

Gaucher, G. et al., "Block copolymer micelles: preparation, characterization and application in drug delivery," Journal of Controlled Release 109 (2005) 169-188.*
Zhao, Z. et al., "Polyphosphoesters in drug and gene delivery," Advanced Drug Delivery Reviews 55 (2003) 438-499.*
Zhang, S. et al., "Rapid and Versatile Construction of Diverse and Functional Nanostructures Derived from a Polyphosphoester-Based Biomimetic Block Copolymer System," Journal of the American Chemical Society, Oct. 23, 2012, 134, 18467-18474.*
International Search Report and Written Opinion; PCT/US2013/062974; pp. 9, Feb. 11, 2014.
Wang et al.; "Self-Assembled Micelles of Biodegradable Triblock Copolymers Based on Poly(ethyl ethylene phosphate) and Poly(-Caprolactone) as Drug Carriers"; Biomacromolecules; vol. 9; pp. 388-395, 2008.

* cited by examiner

POLYMER-DRUG SYSTEMS

PRIORITY CLAIM

The present application claims priority under 35. U.S.C. §119 to U.S. Provisional Patent Application Ser. No. 61/708,911, filed Oct. 2, 2012, titled Polymer-Drug Systems, which is incorporate by reference herein in its entirety.

STATEMENT OF GOVERNMENT INTEREST

This invention was made with government support under Grant No. HHSN268201000046C awarded by the National Institutes of Health, and under Grant No. DMR 1105304 awarded by the National Science Foundation. The government has certain rights in the invention.

The Welch Foundation has contributed to the development of the invention through support provided by the W. T. Doherty-Welch Chair (A-0001).

BACKGROUND

Polymer micelles are one type of nanovector formed by the aqueous assembly of block copolymers that are polymer chains containing both hydrophilic and hydrophobic portions. These structures often exist as spherical particles with a core-shell morphology and sub-micron diameter. The design of nanovectors, such as block copolymer micelles, that effectively mimic the selectivity and evasiveness of viral particles remains a major goal of drug delivery research.

The chemotherapeutic agent paclitaxel (PTX), a microtubule-interfering agent, has demonstrated a broad spectrum of antitumor activity against various cancers including breast, lung and advanced ovarian cancers. The low solubility of PTX and the difficulty of achieving sufficiently high concentration in solution that is suitable for in vivo administration and clinical applications have led to the development of various strategies to increase its bioavailability, which utilize low molecular weight surfactants (e.g., Taxol®), coat the drug with albumin (e.g., Abraxane®), or conjugate it to water-soluble polymers (e.g., PTX poliglumex, OPAXIO™, CT-2103, Xyotax®). Other delivery mechanisms for PTX that have been developed include a number of degradable and non-degradable drug conjugates, such as PTX-conjugated polyvalent DNA-functionalized gold nanoparticles, polylactide (PLA)-PTX conjugated nanoparticles and PTX cross-linked PLA-based nanocomposites.

However, there are several challenges with the formulation of PTX that remain unmet. For example, present formulations fail to achieve the desired high PTX loading (e.g., due to reaction non-selectivity in many present formulations) while also maintaining high water solubility so as to be suitable for in vivo administration and clinical applications. Also, the toxicity and hypersensitivity reactions associated with vehicles for the delivery of many present formulations of PTX (e.g., Cremophor-EL, polyethoxylated castor oil) remain problematic.

The present disclosure addresses these needs, among others, by providing compounds, methods for synthesizing compounds, and formulations and applications of compounds, that, in some embodiments, achieve high loading of PTX, increase PTX solubility, and other chemotherapeutic agents, and that exhibit low toxicity, allow controlled PTX release kinetics, and are capable of extended circulation in vivo, and have a possibility of versatile chemical modifications—for instance, the conjugation of imaging agents and/or targeting ligands.

SUMMARY

The present disclosure generally relates to polymer-drug systems, and more particularly to nanoscopic particles comprising amphiphilic block copolymers conjugated, physically encapsulated, or otherwise combined with chemotherapeutic agents along a selective region or regions of the backbone of the copolymer, so as to package the chemotherapeutic agent in selective domains within each nanoscopic particle, as well as to methods for making such particles, and applications and methods for using such particles, including in the formation of polymer micelles.

The features and advantages of the present invention will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings. The patent or application file contains at least one drawing executed in color. Copies of this patent or patent application publication with color drawing(s) will be provided by the Office upon request and payment of the necessary fee.

FIGS. 8A-8D depict aser scanning confocal microscopy analysis of the cellular uptake of fluorescein-labeled PPE-PTX nanoparticles (green panel) into RAW 264.7 mouse macrophages. Two- and three-dimensional images were collected for both the control-untreated cells (FIG. 8A and FIG. 8B) and the cell-treated with the PTX-loaded nanoparticles (15 µM, FIG. 8C and FIG. 8D). The nucleus were stained with DRAQ5 nuclear stain (blue panel), whereas the fluorescein appears in green. The transmitted light-images and merged images are also indicated. The changes in the nuclear morphology after the treatment with the nanoparticles are indicated by the red arrows.

Figure 9:
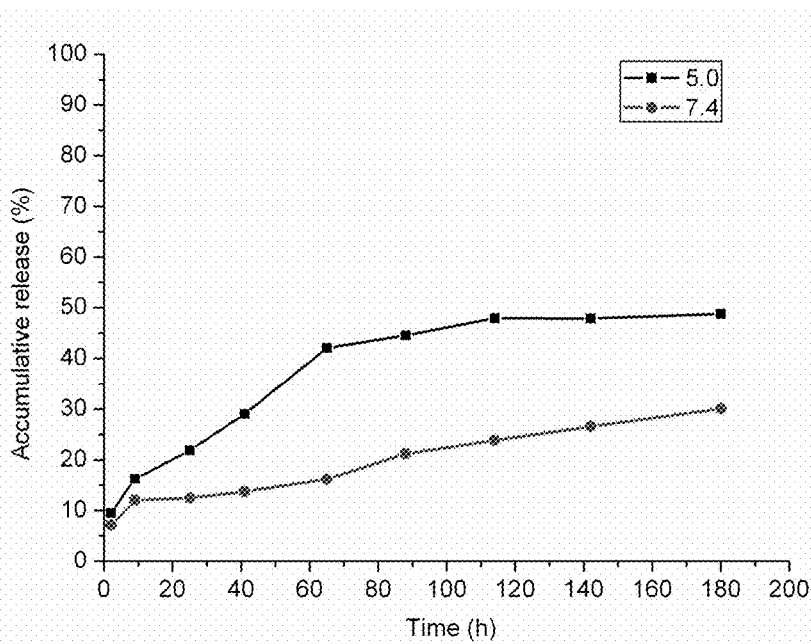

FIG. 9 depicts PTX release from PPE-PTX-G2 at different pH.

Figure 10A:
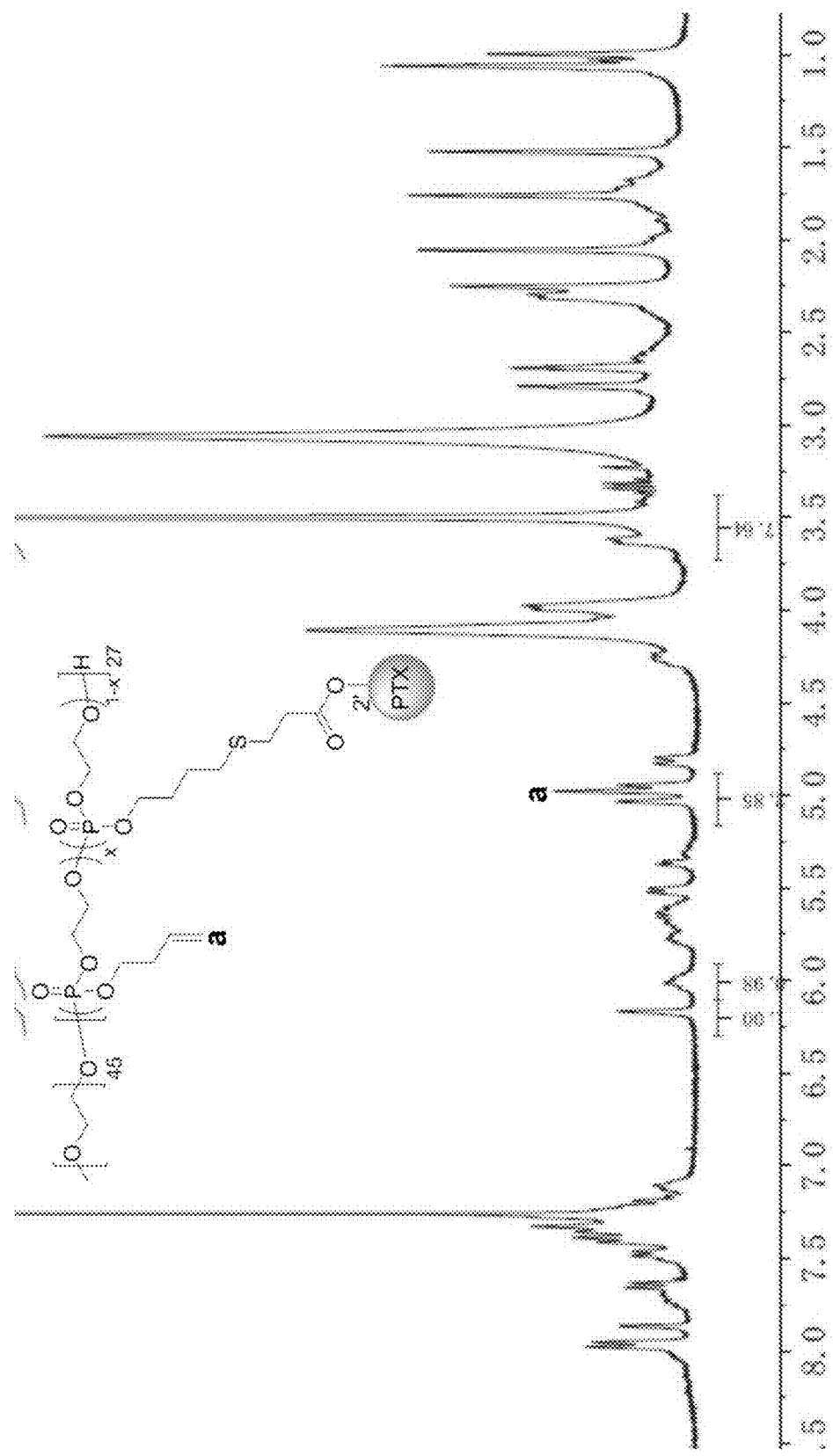

FIG. 10A depicts a $^1$H NMR spectrum for PPE-PTX-G2.

Figure 10B:
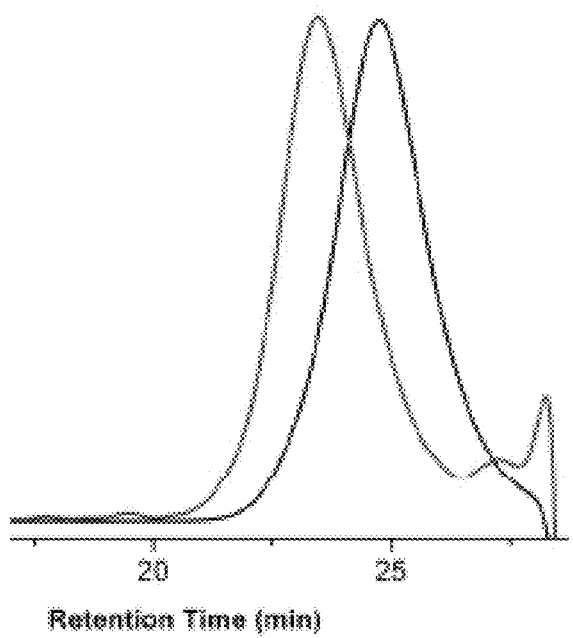

FIG. 10B depicts GPC for PPE-PTX-G2.

Figure 11A:
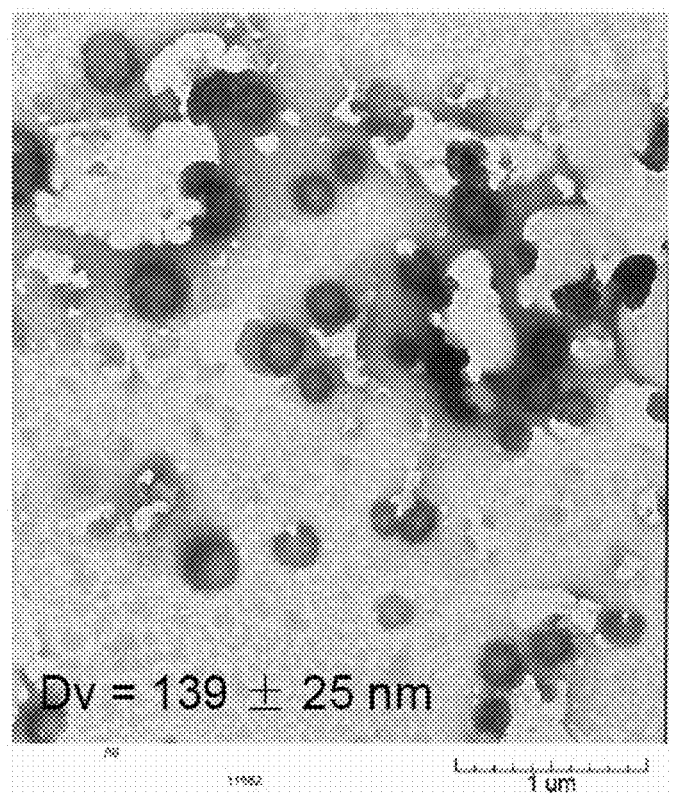

FIG. 11A depicts a TEM image showing the morphology of PPE-PTX-G2.

Figure 11B:
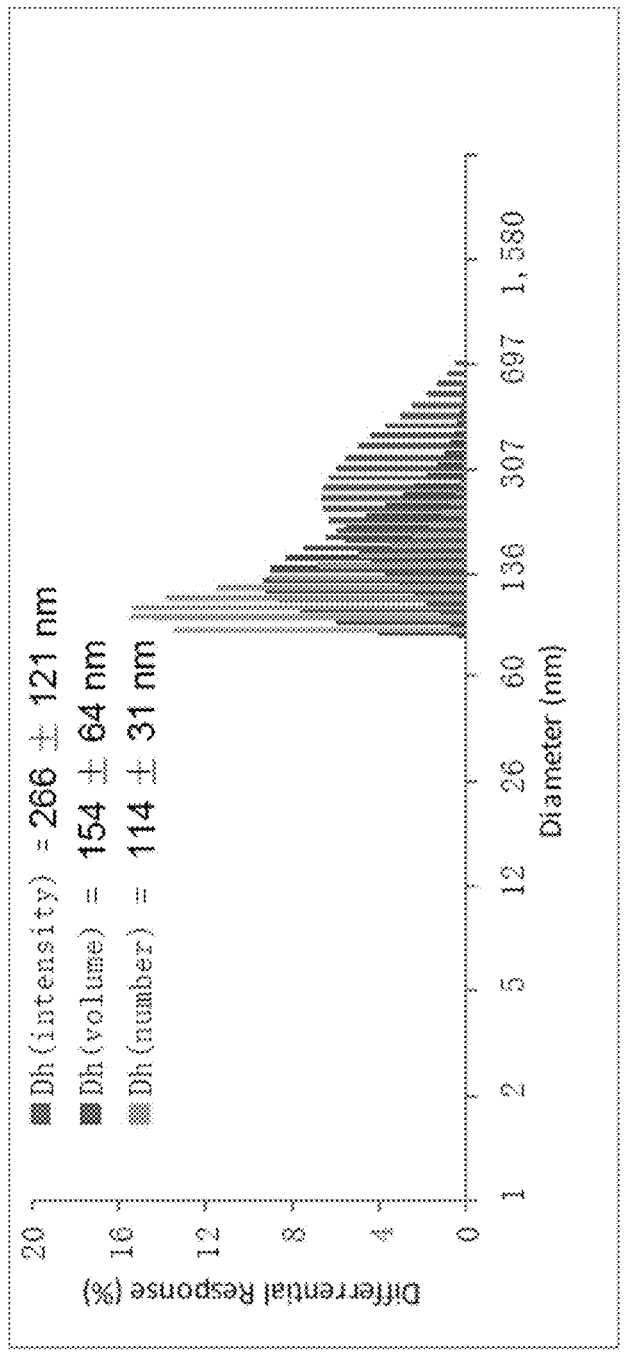

FIG. 11B depicts the size distribution of PPE-PTX-G2 as examined with DLS.

Figure 12A:
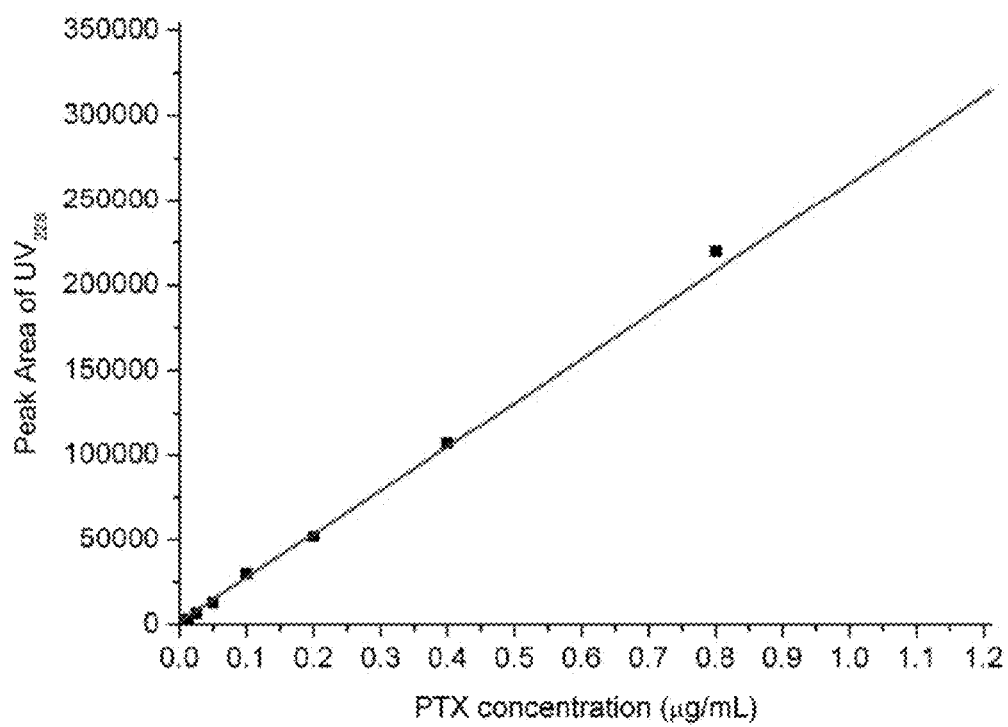

FIG. 12A depicts the saturate concentration of PTX in PBS buffer as determined by UV.

Figure 12B:
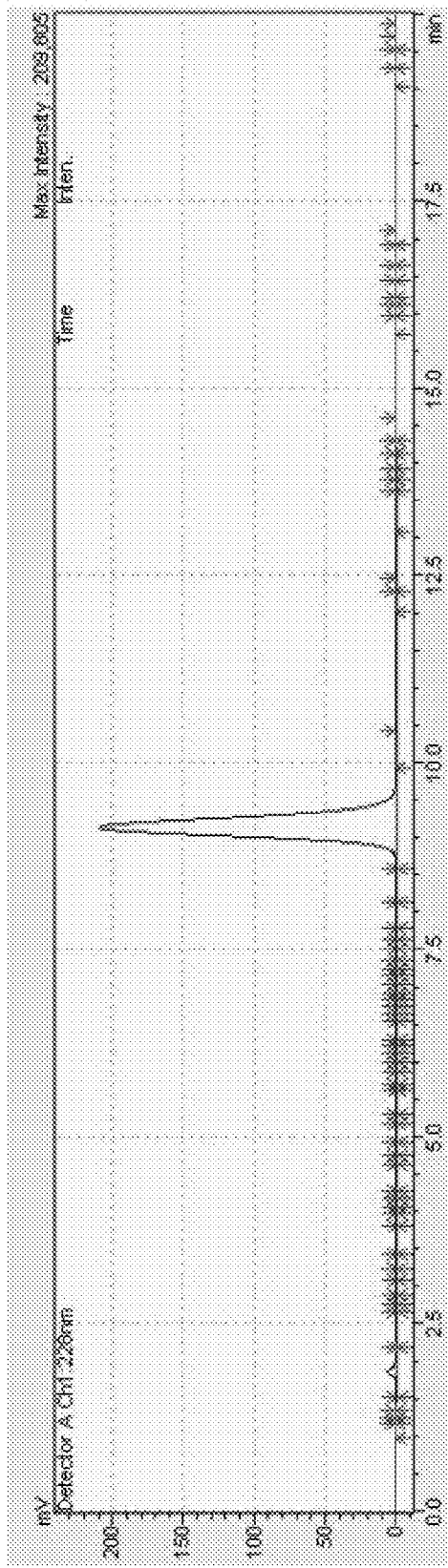

FIG. 12B depicts an example UV spectrum.

Figure 13:
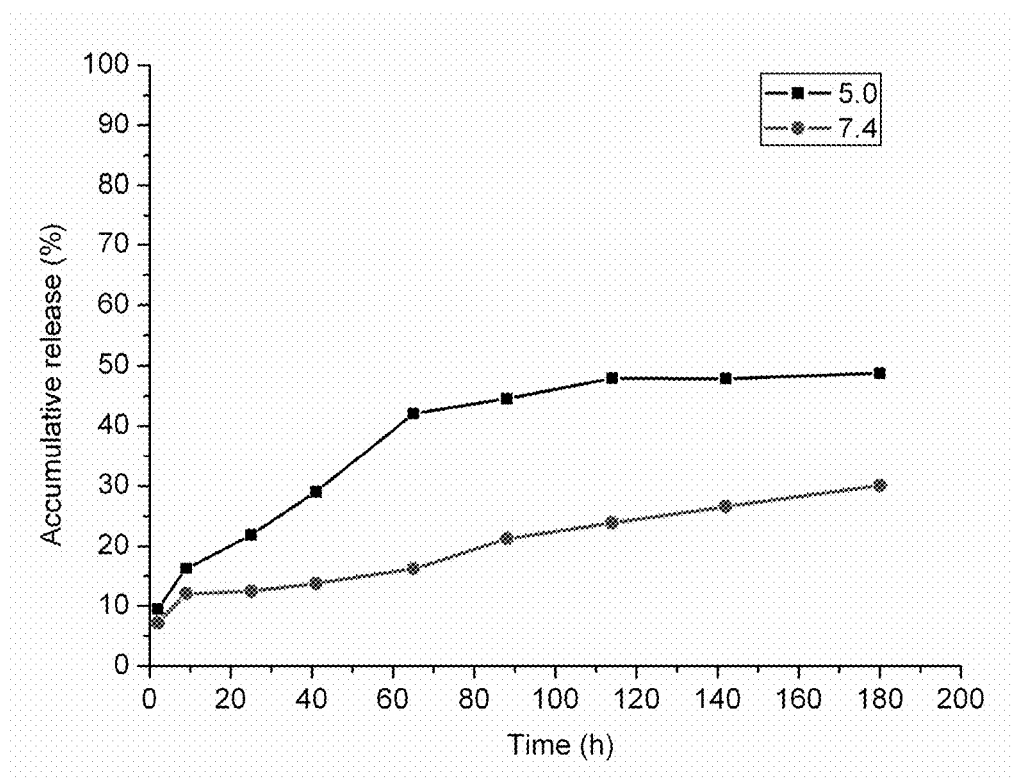

FIG. 13 depicts the release of PTX from PPE-PTX-G2 at different pHs as determined using HPLC.

Figure 14:
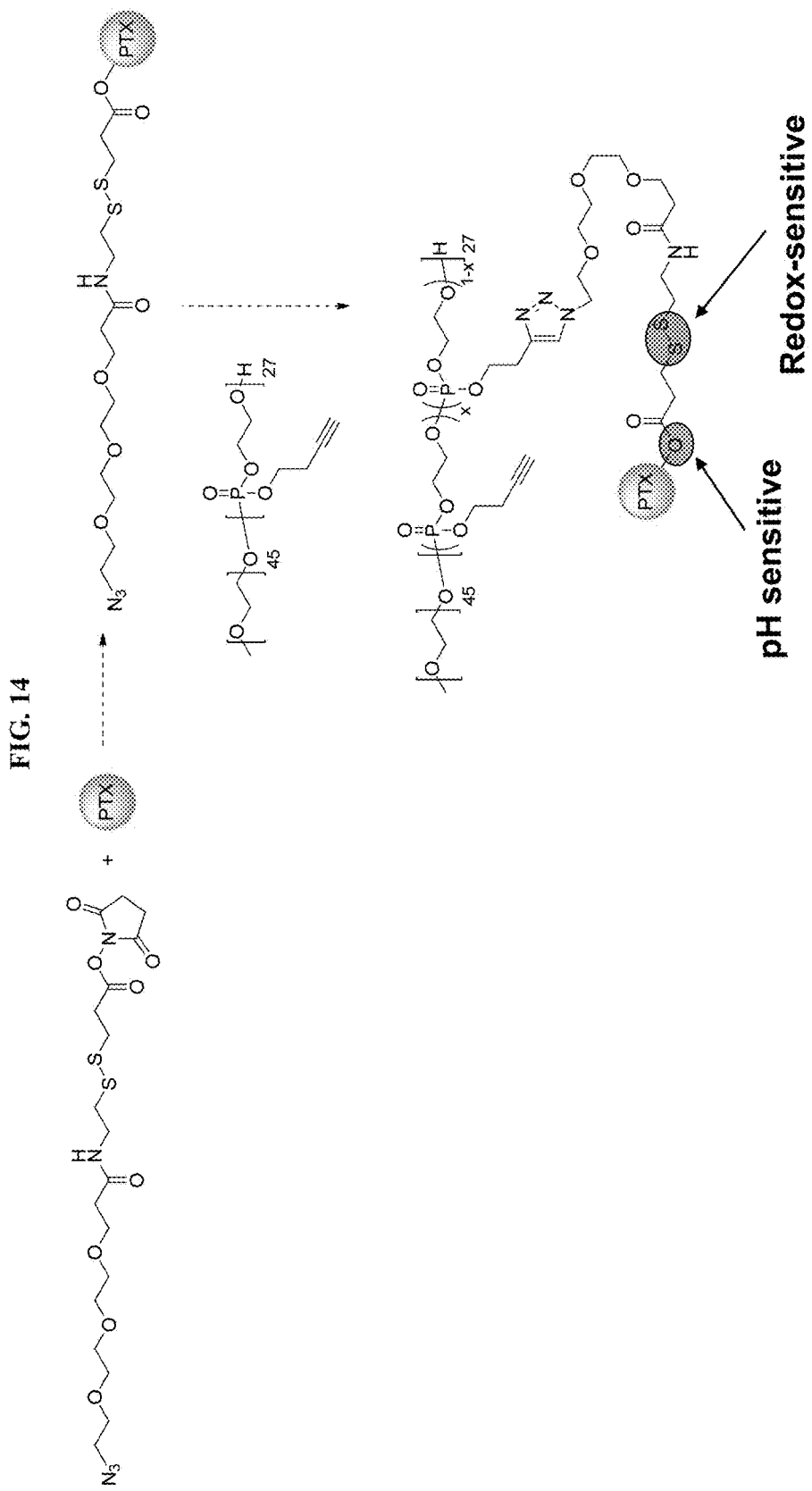

FIG. 14 depicts a synthesis scheme for PPE-TX-G3. A redox-sensitive disulfide bond and a pH-sensitive bond are indicated.

Figure 15:
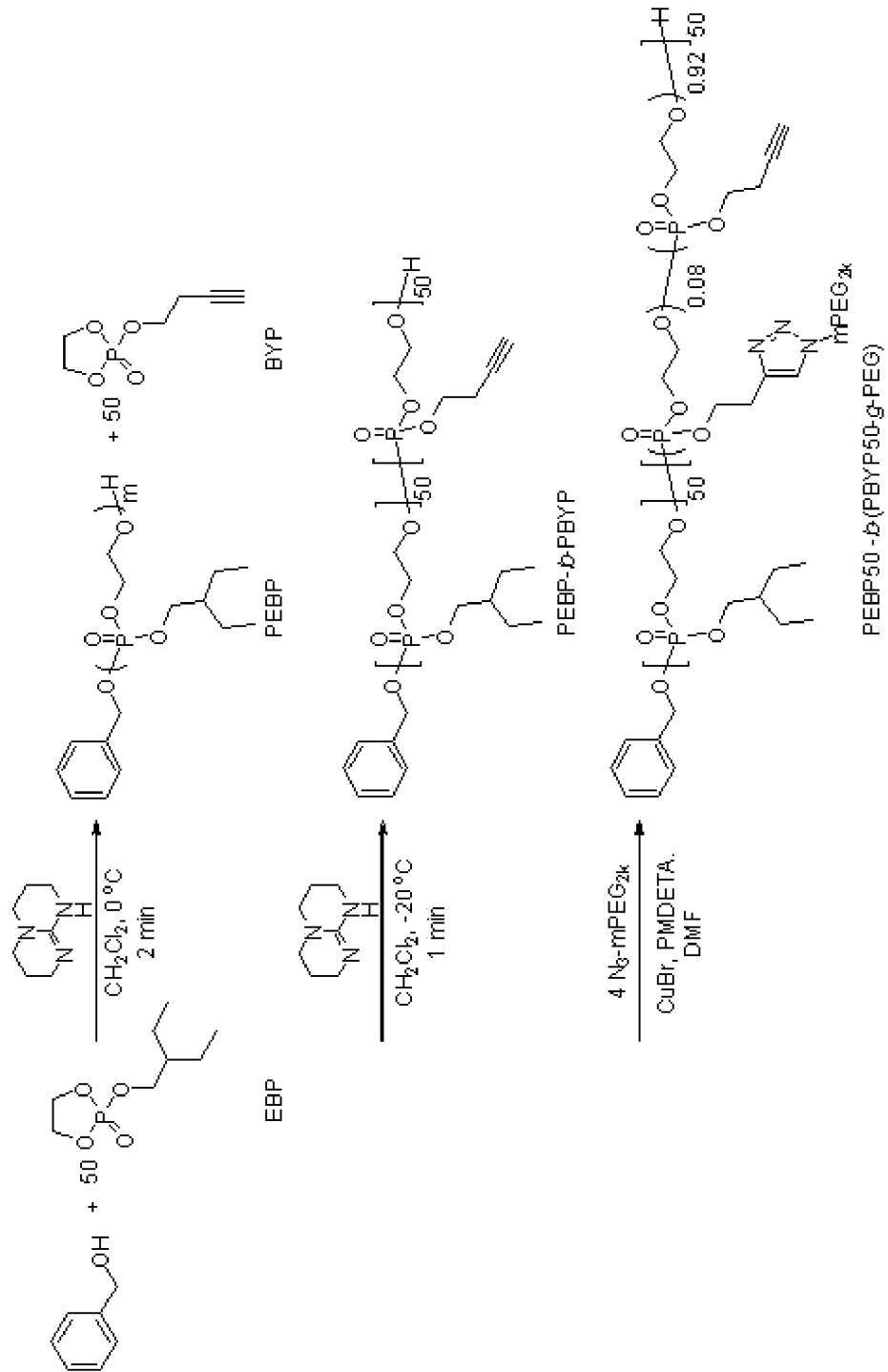

FIG. 15 depicts a synthesis scheme for a PEBP-b-(PBYP-g-PEG) block graft terpolymer.

Figure 16:
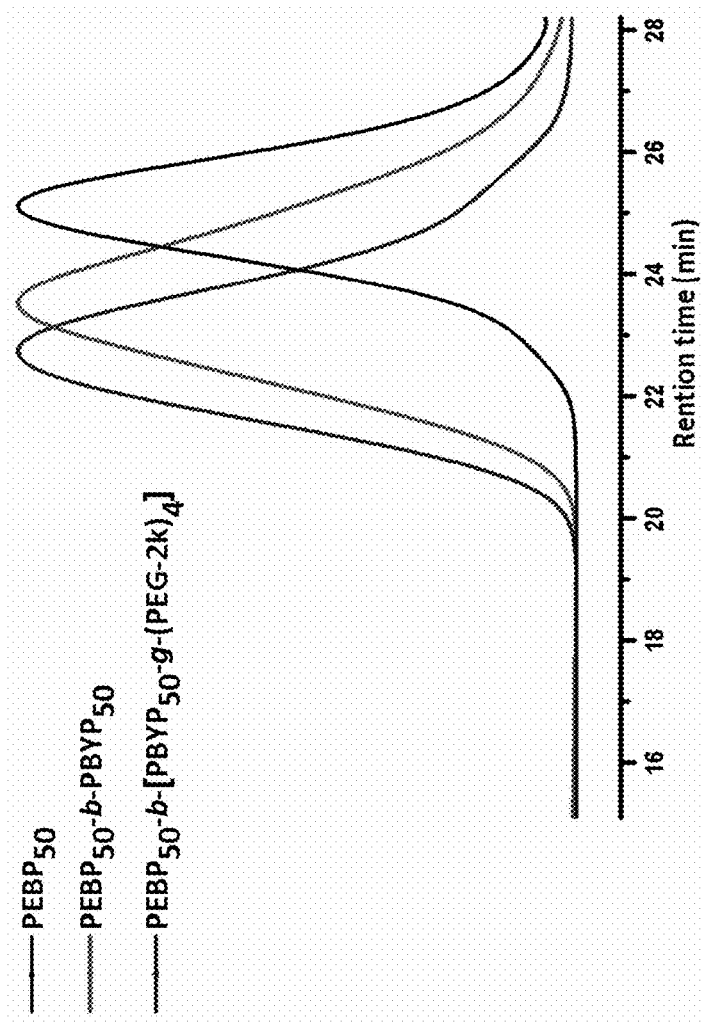

FIG. 16 depicts GPC analysis of the PEBP-b-(PBYP-g-PEG) block graft terpolymer.

Figure 17A:
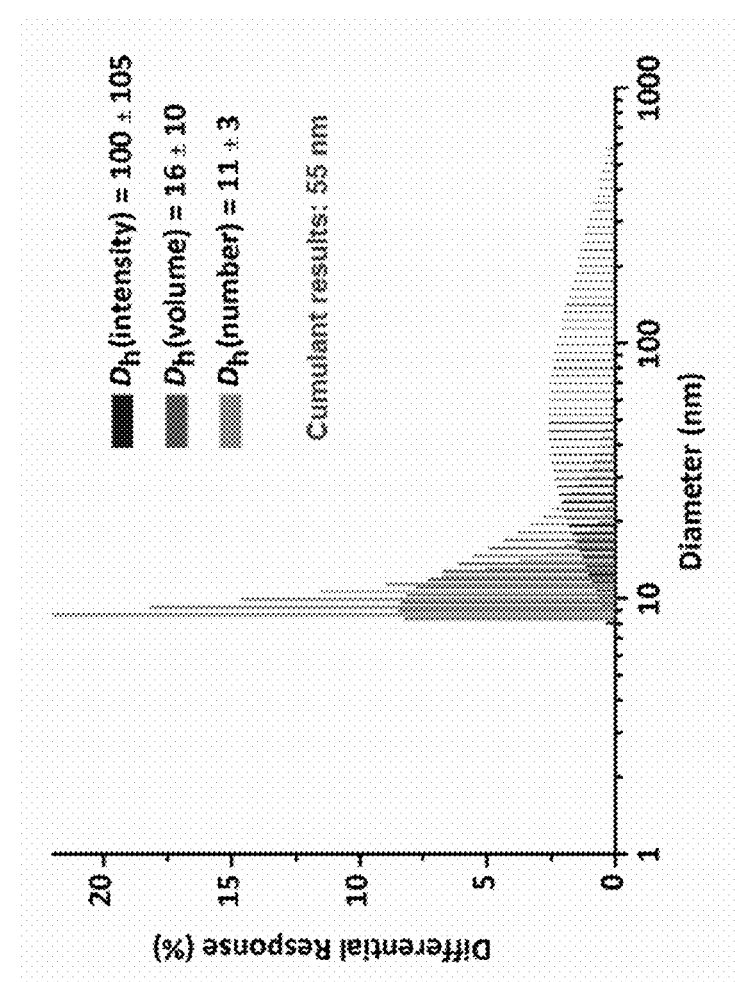

FIG. 17A depicts DLS characterization of micellar nanoparticles of PEBP-b-(PBYP-g-PEG) block graft terpolymer loaded with PTX.

Figure 17B:
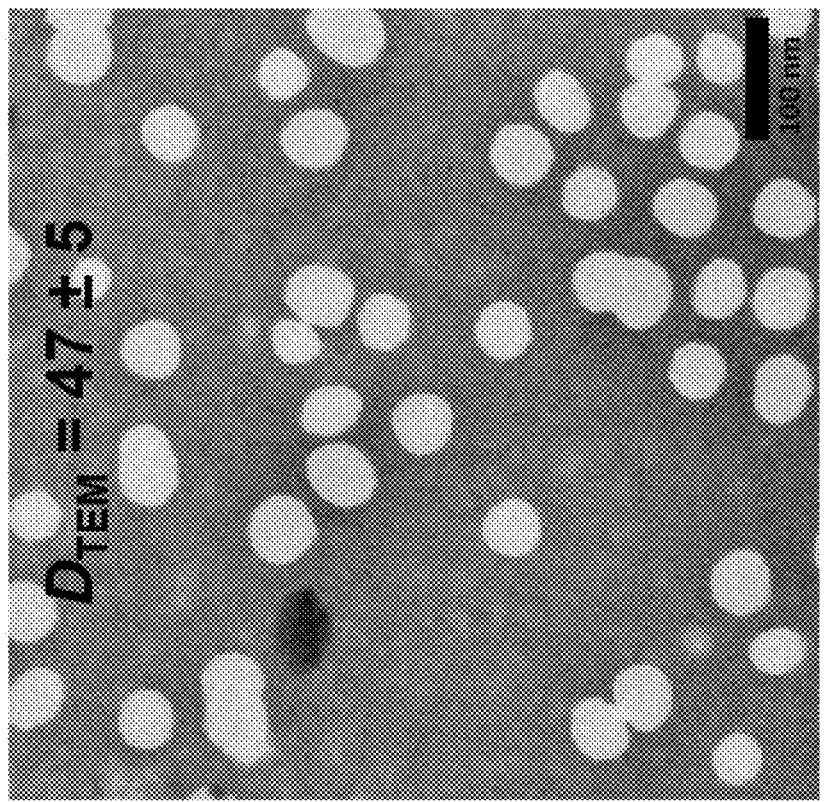

FIG. 17B depicts TEM images of micellar nanoparticles of PEBP-b-(PBYP-g-PEG) block graft terpolymer loaded with PTX. Micelles were stained with uranyl acetate.

Figure 18:
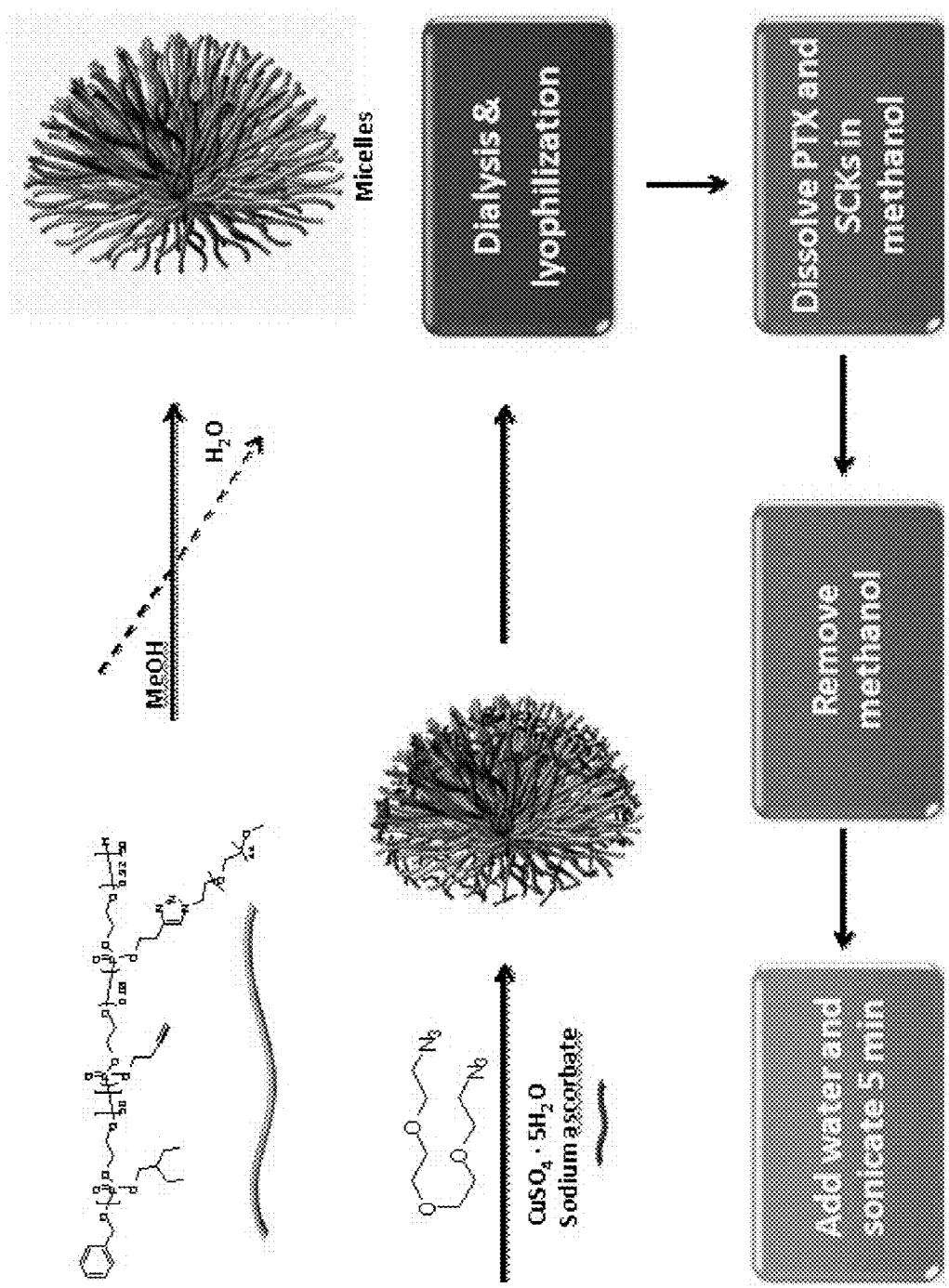

FIG. 18 depicts a scheme for preparing shell-cross-linked nanoparticles of PEBP-b-(PBYP-g-PEG) block graft terpolymer loaded with PTX.

Figure 19A:
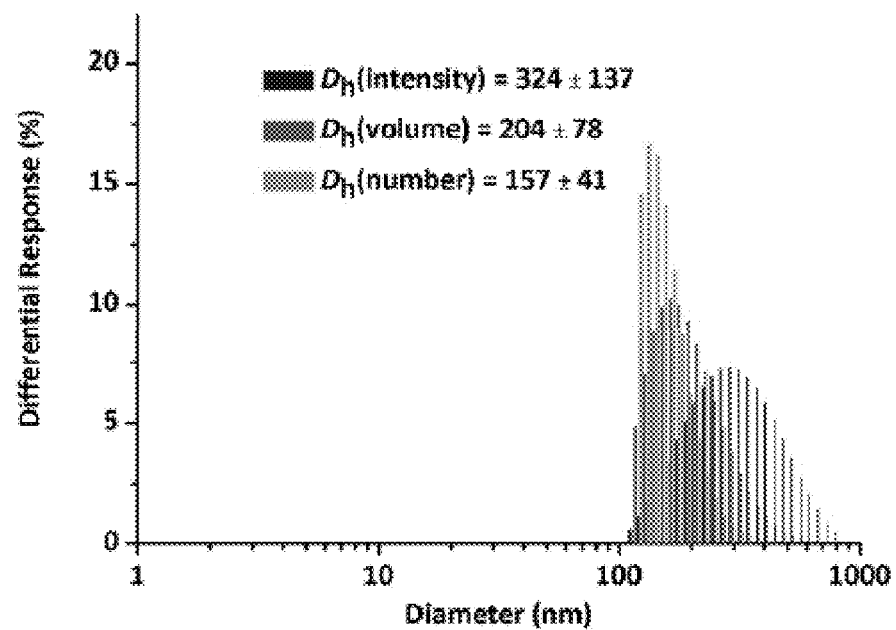
Figure 19A:
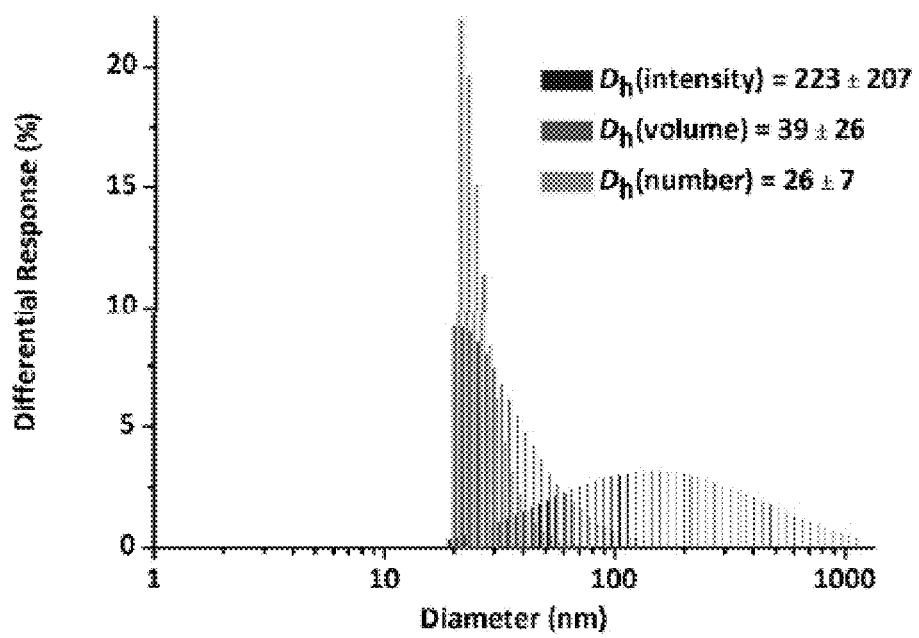
Figure 19A:
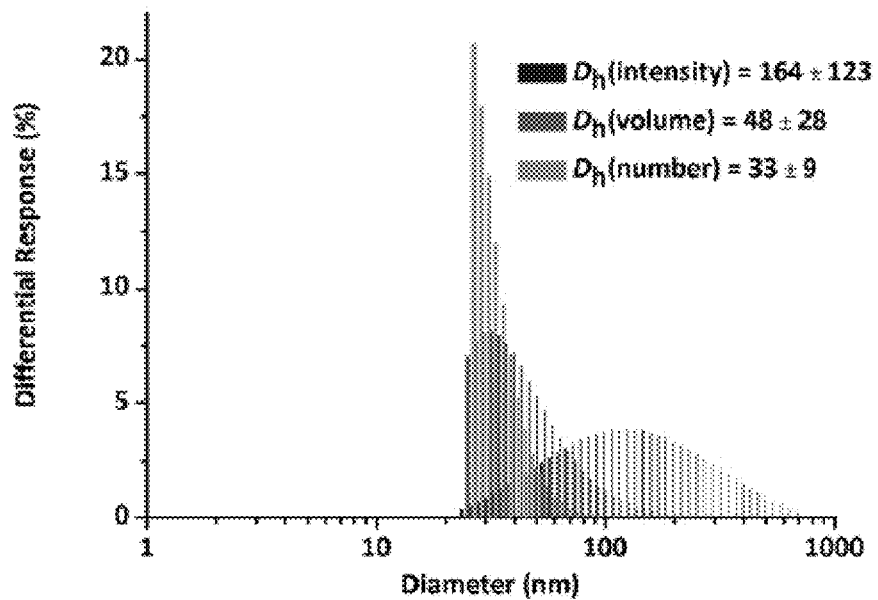

FIG. 19A depicts DLS analyses of representative samples of materials prepared according to FIG. 18.

Figure 19B:
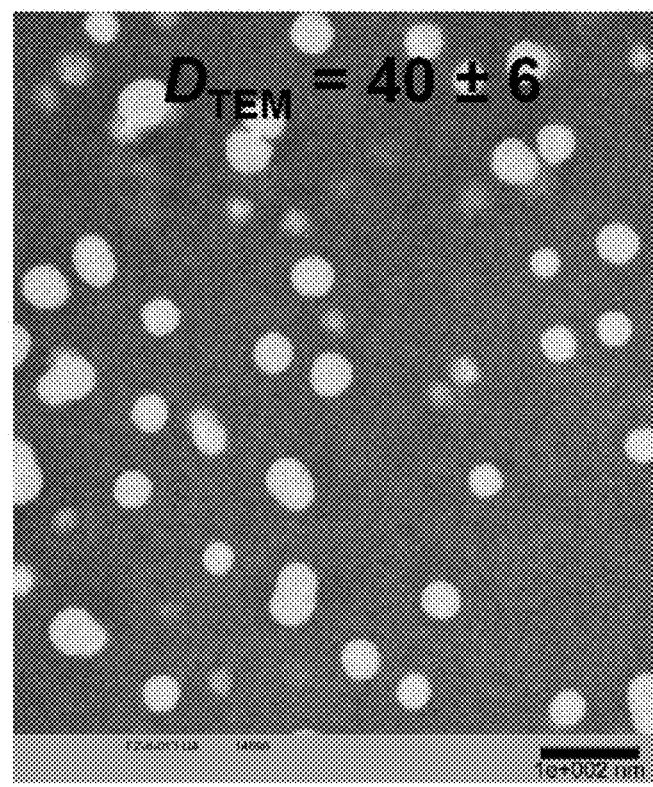
Figure 19B:
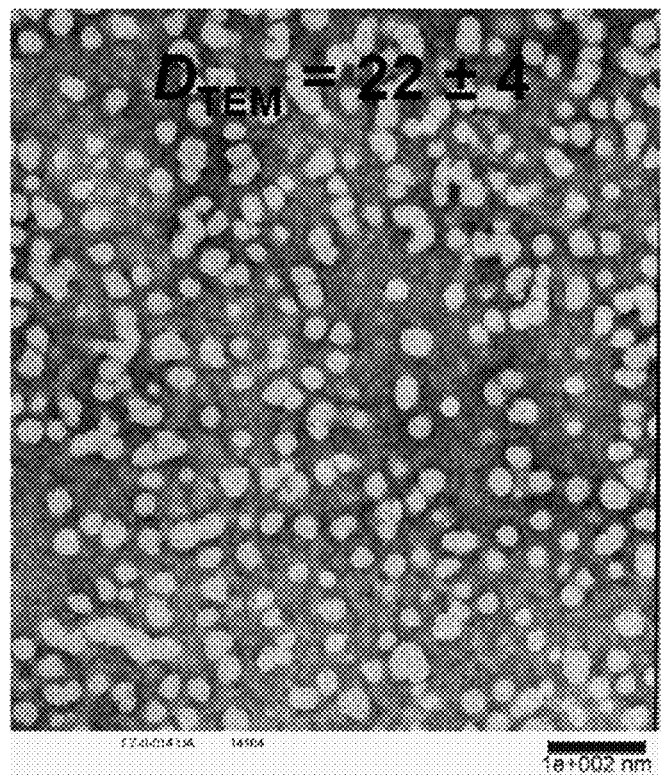
Figure 19B:
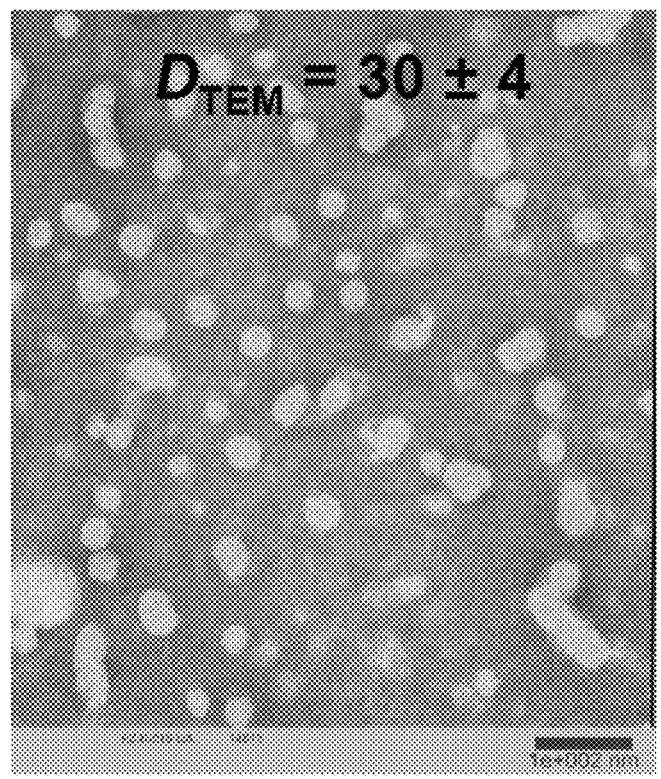

FIG. 19B depicts TEM images of representative samples of materials prepared according to FIG. 18.

Figure 20:
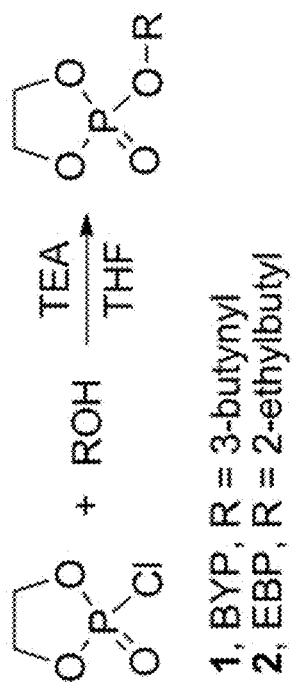

FIG. 20 depicts a scheme for synthesis of cyclic phospholane monomers from COP and primary alcohols.

Figure 21:
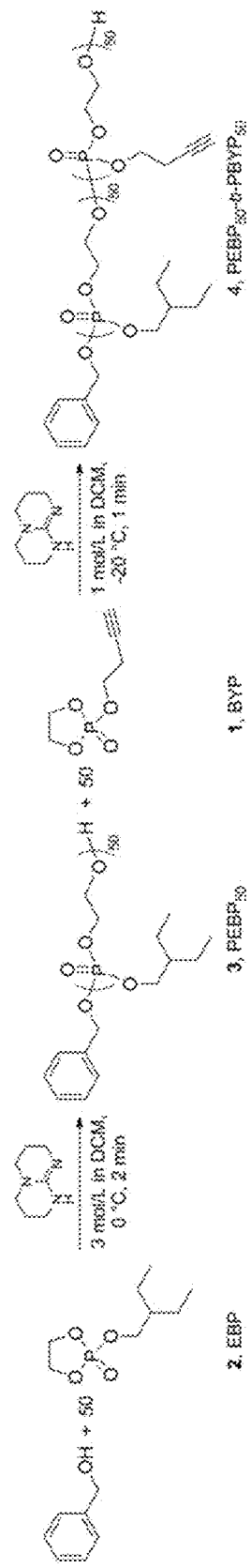

FIG. 21 depicts a scheme for synthesis of PEBP$_{50}$-b-PBYP$_{50}$, 4, diblock polyphosphoester bearing a hydrophobic block (PEBP) and a functional block (PBYP) via a one-pot sequential ROP.

Figure 22:
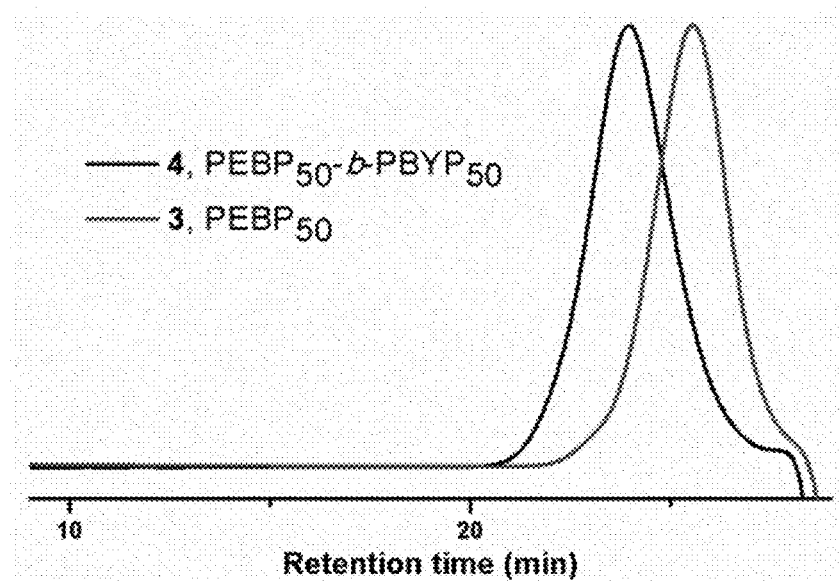

FIG. 22 depicts GPC traces of PEBP$_{50}$ at M$_n$=9800 g/mol and PDI=1.14 and PEBP$_{50}$-b-PBYP$_{50}$ diblock copolymer at M$_n$=16700 g/mol and PDI=1.17) produced by the one-pot sequential ROP.

Figure 23:
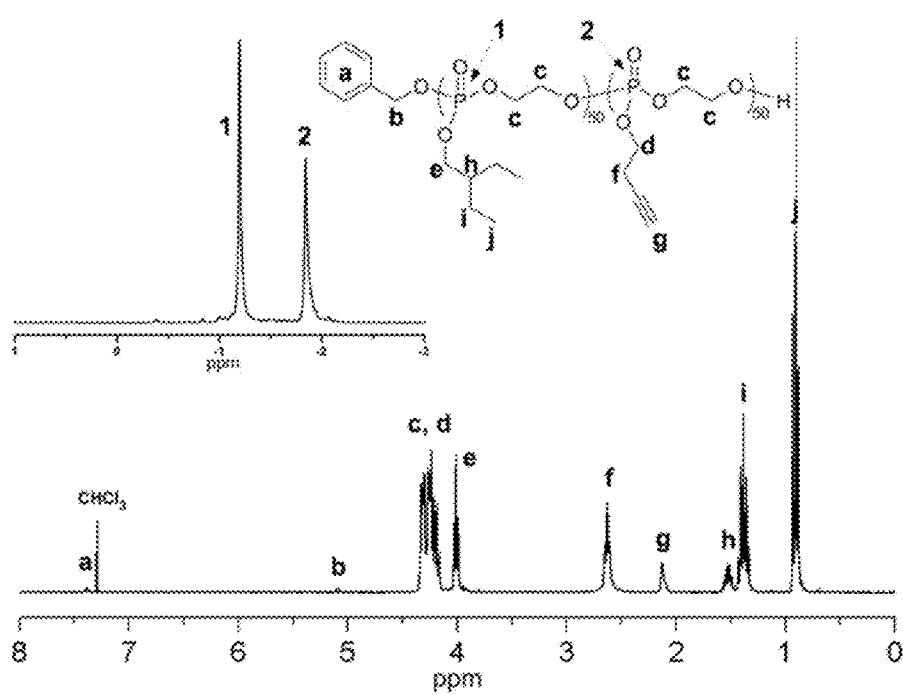

FIG. 23 depicts $^1$H NMR and $^{31}$P NMR (upper left inset) spectra (CDCl$_3$) of purified PEBP$_{50}$-b-PBYP$_{50}$ diblock copolymer.

Figure 24A:
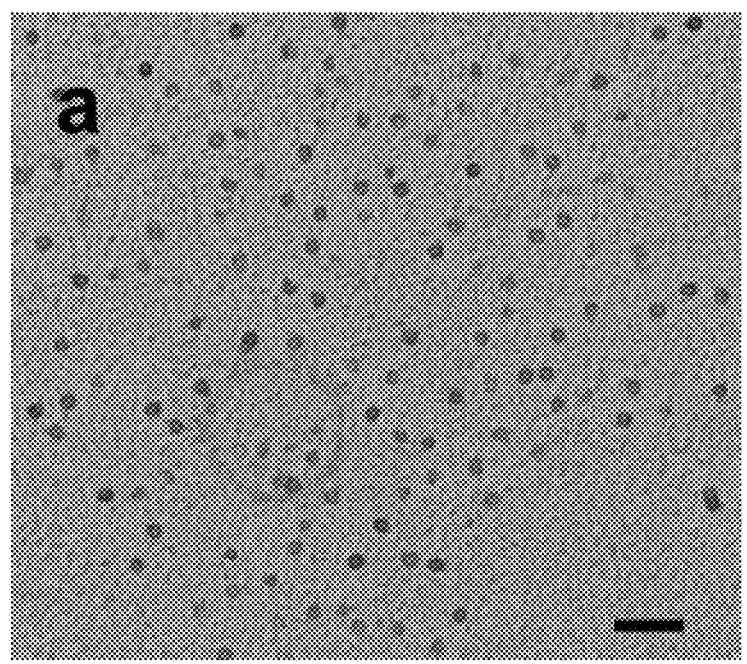
Figure 24B:
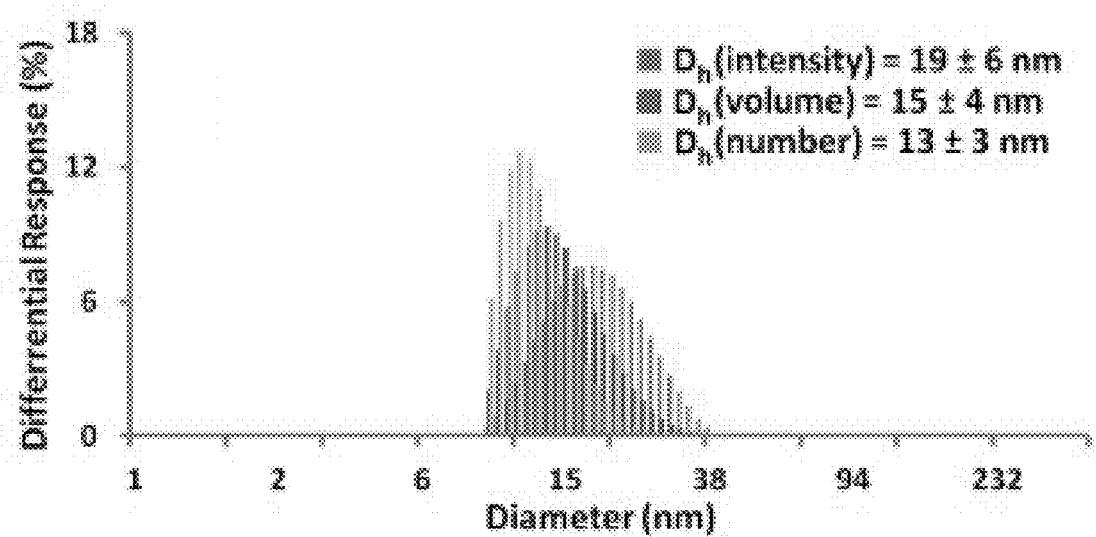
Figure 24C:
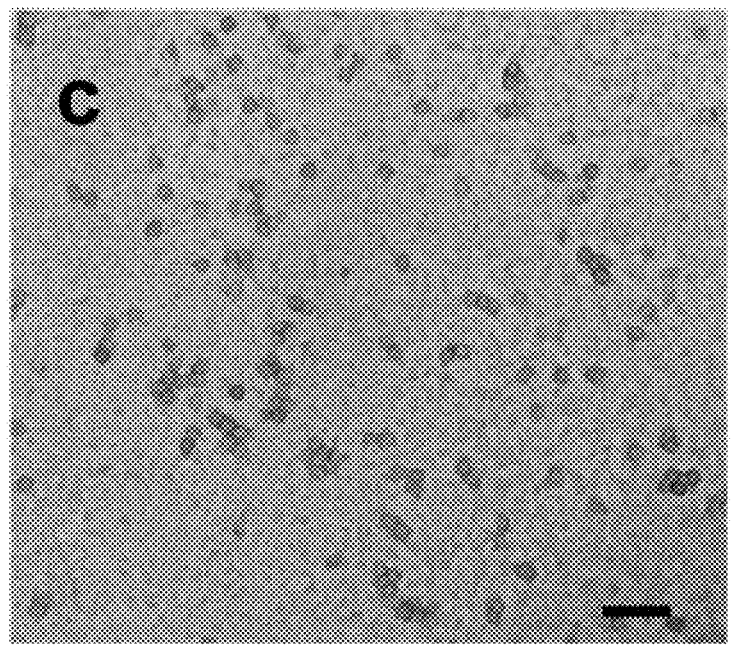
Figure 24D:
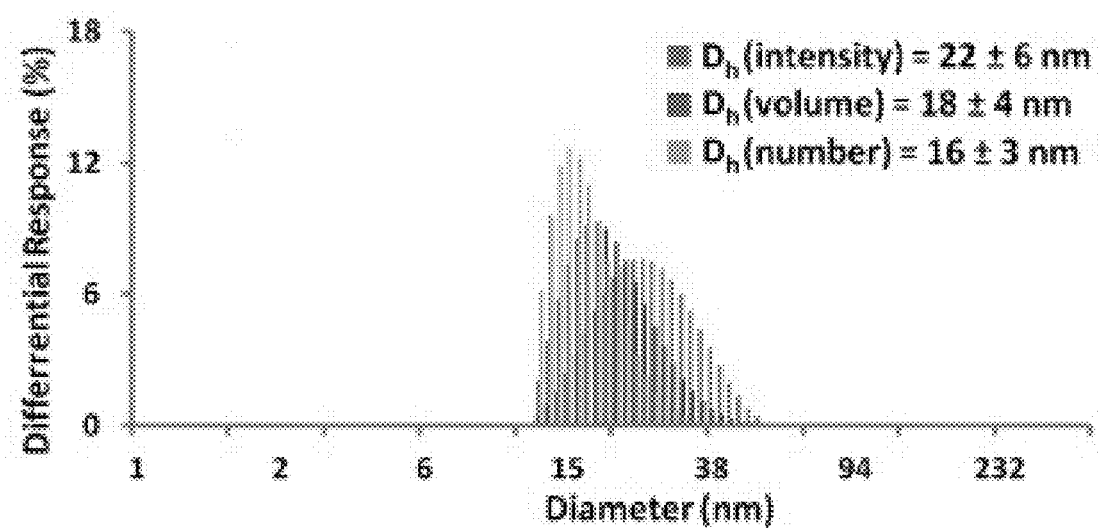
Figure 24E:
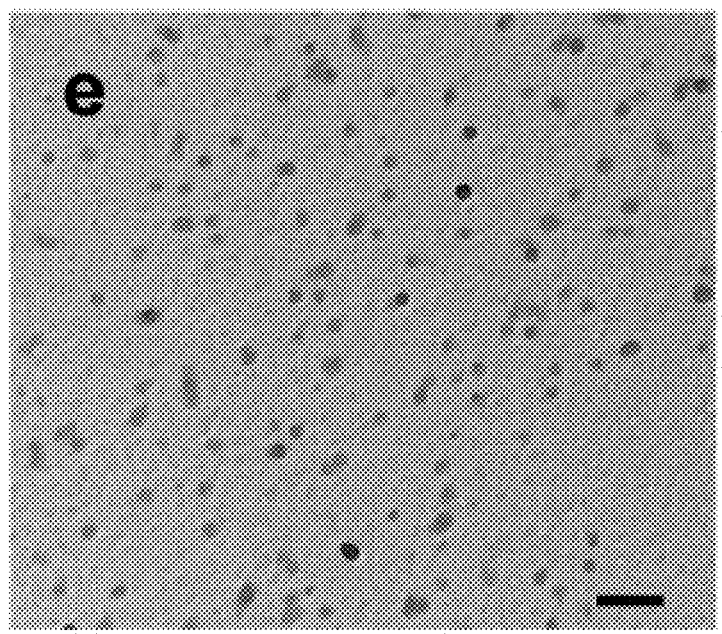
Figure 24F:
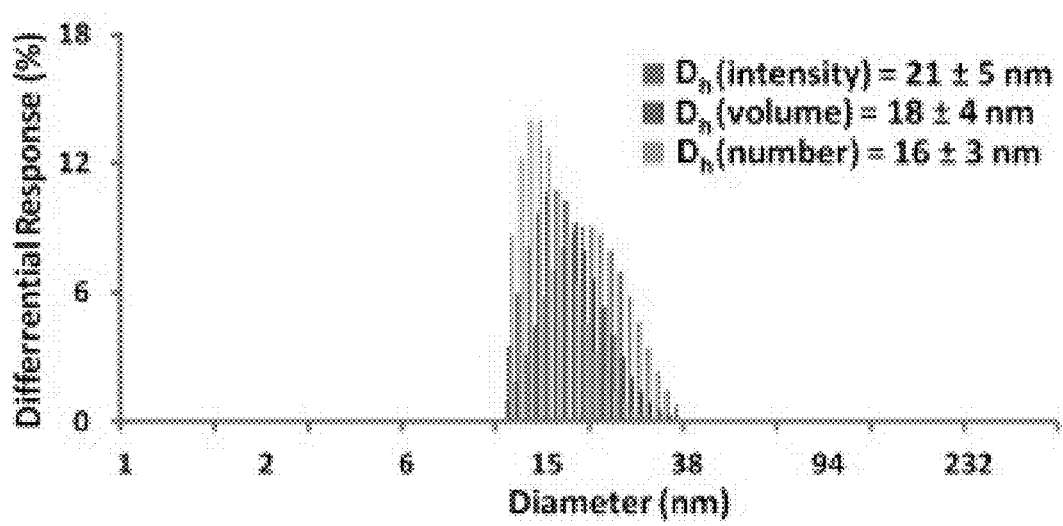
Figure 24G:
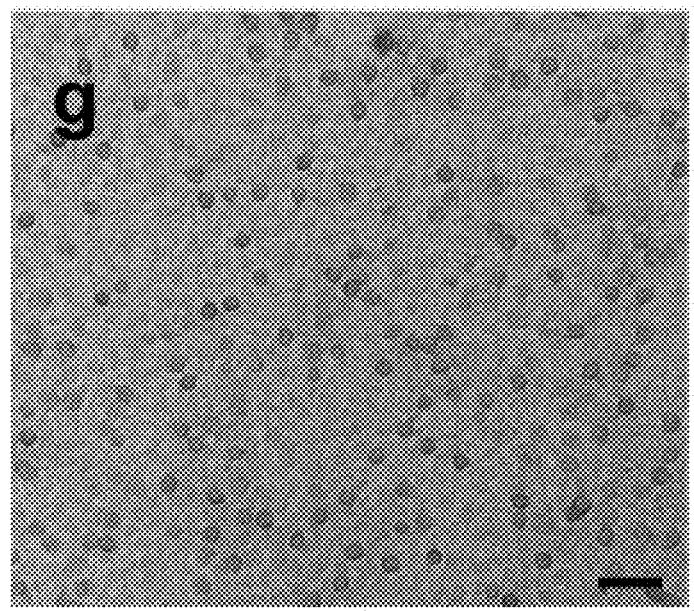
Figure 24H:
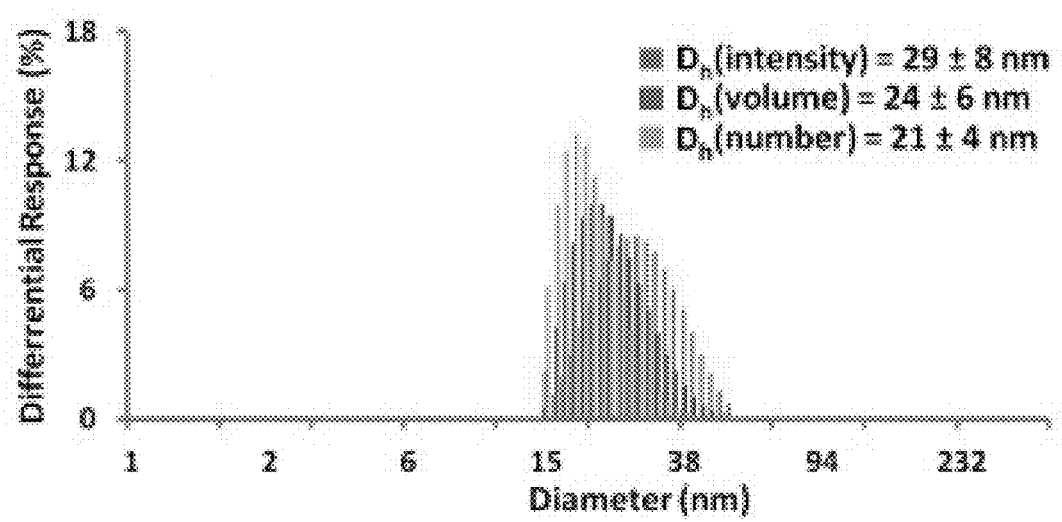

FIGS. 24A-24H depict self-assembly results of non-ionic micelle 9 (FIG. 24A and FIG. 24E), anionic micelle 10 (FIG. 24B and FIG. 24F), cationic micelle 11 (FIG. 24C and FIG. 24G), zwitterionic micelle 12 (FIG. 24D and FIG. 24H in nanopure water. In FIG. 24A, a TEM image of 9, average diameter is 15±3 nm, after counting more than 100 particles. In FIG. 24B, the DLS results of 9 are D$_h$(intensity)=19±6 nm, D$_h$(volume)=15±4 nm, D$_h$(number)=13±3 nm. In FIG. 24C, a TEM image of 10, average diameter is 18±4 nm, after counting more than 100 particles. In FIG. 24D, the DLS results of 10 are D$_h$(intensity)=22±6 nm, D$_h$(volume)=18±4 nm, D$_h$(number)=16±3 nm. In FIG. 24E, a TEM image of 11, average diameter is 18±5 nm, after counting more than 100 particles. In FIG. 24F, the DLS results of 11 are D$_h$(intensity)=21±5 nm, D$_h$(volume)=18±4 nm, D$_h$(number)=16±3 nm. In FIG. 24G, a TEM image of 12, average diameter is 23±3 nm, after counting more than 100 particles. In FIG. 24H, the DLS results of 12 are D$_h$(intensity)=29±8 nm, D$_h$(volume)=24±6 nm, D$_h$(number)=21±4 nm. All scale bars in TEM images are 100 nm.

Figure 25:
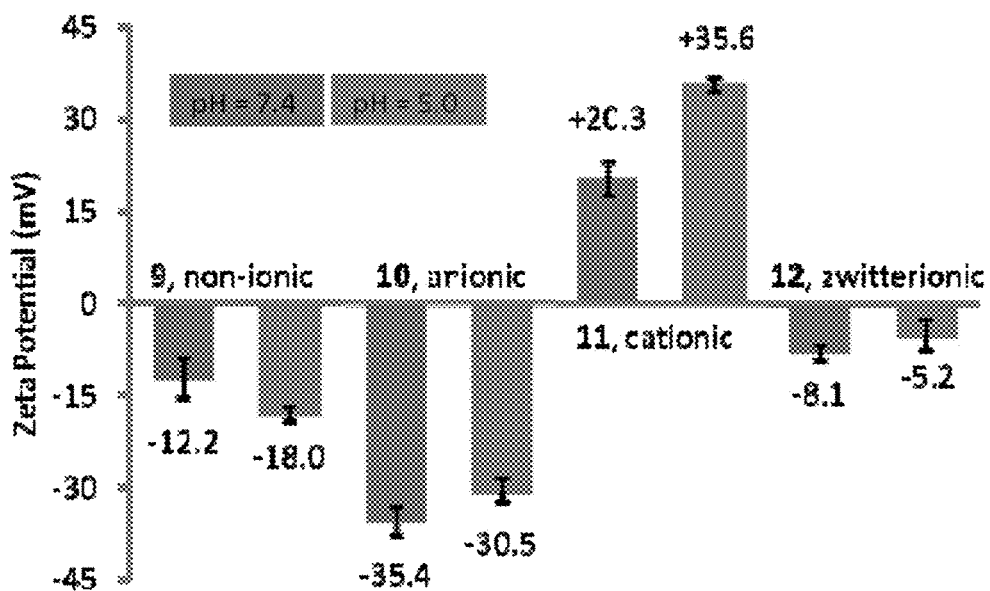

FIG. 25 depicts the zeta potential values of 9, 10, 11 and 12 in PBS buffer solutions at pH 7.4 and pH 5.0. The average values and their standard deviations, from six measurements, are shown.

Figure 26:
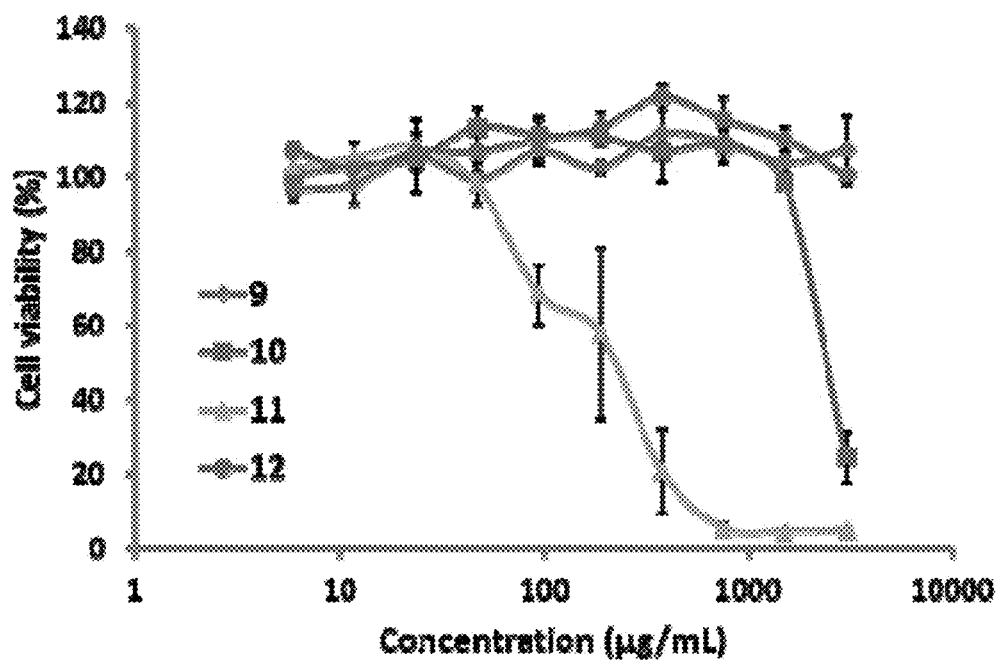

FIG. 26 depicts the cytotoxicity of the non-ionic micelle 9; anionic micelle 10; cationic micelle 11; and zwitterionic micelle 12 in RAW 264.7 mouse macrophages after treatment at a concentration range of 5-to-3000 µg/mL for 24 h.

Figure 27:
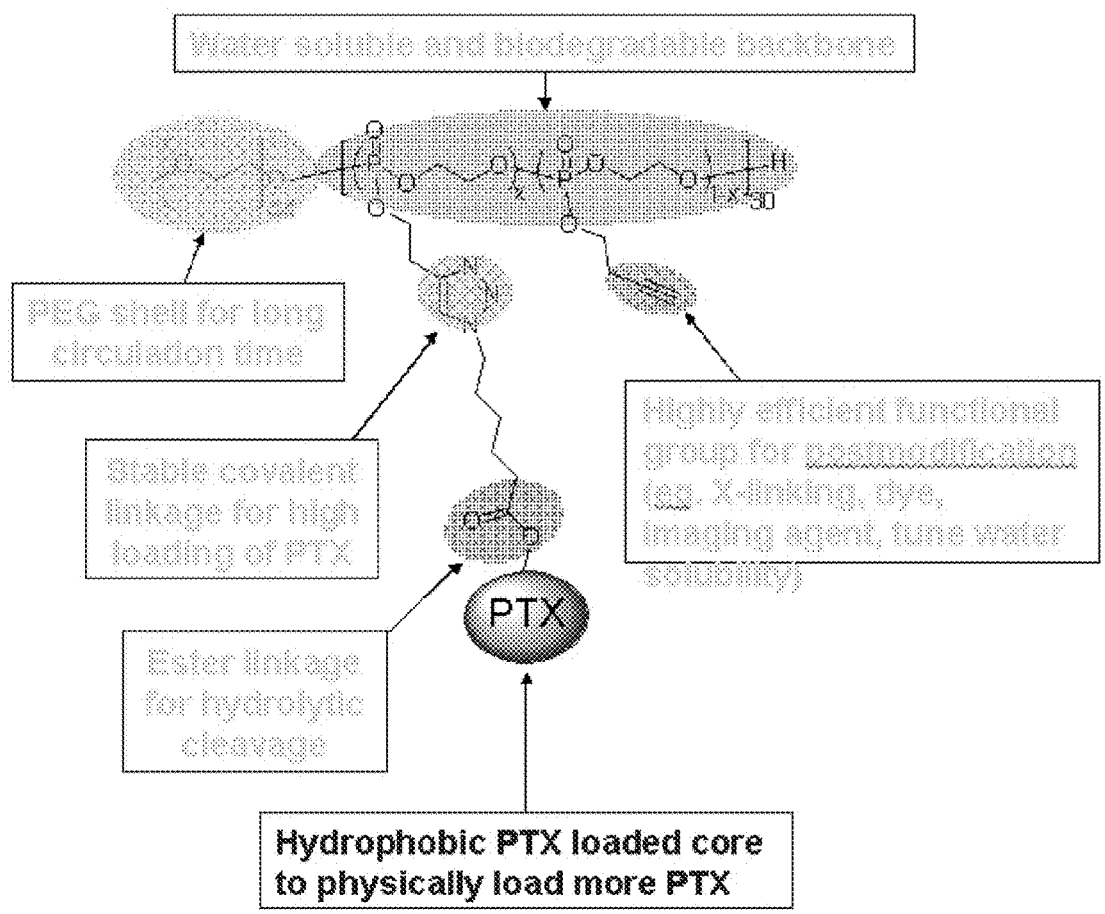

FIG. 27 depicts features of a drug-copolymer micelle for physical drug loading.

Figure 28:
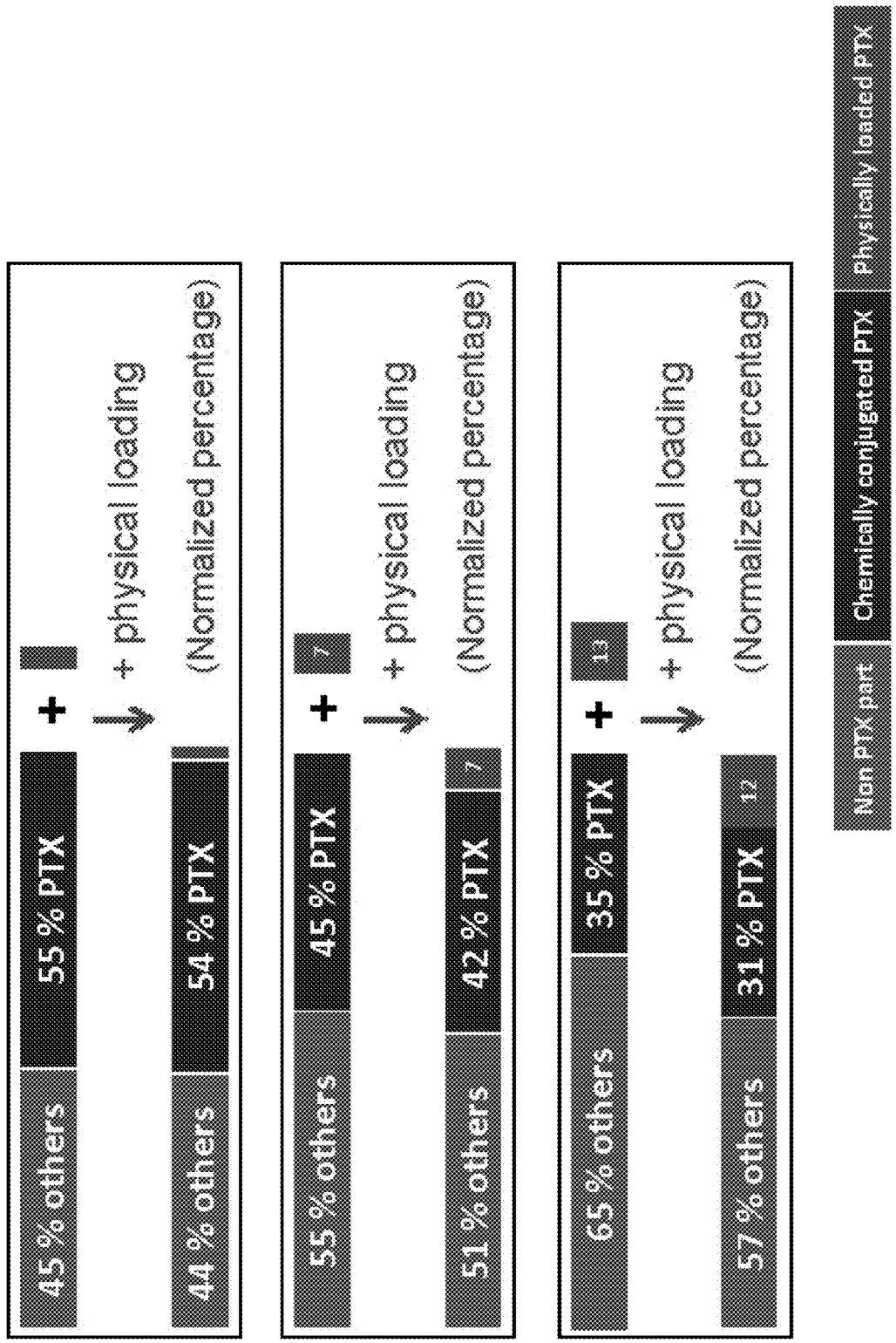

FIG. 28 depicts a method for physical loading of PTX with PTX-copolymer conjugates.

Figure 29:
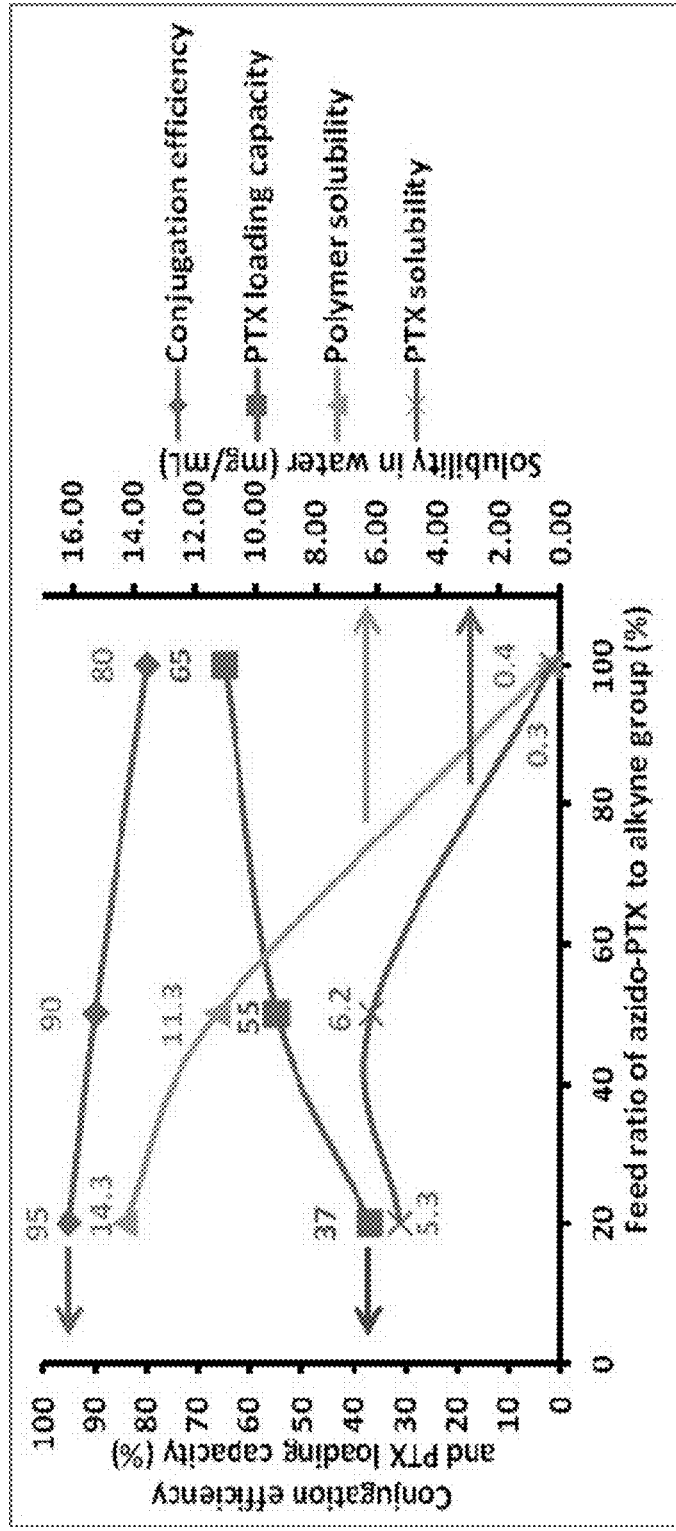

FIG. 29 depicts conjugation efficiency for physical loading of PTX.

Figure 30:
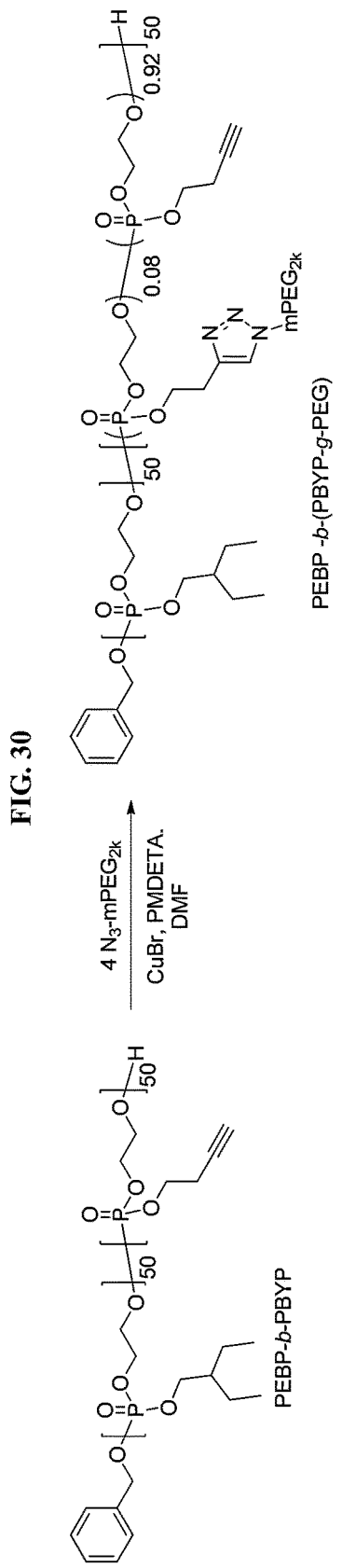

FIG. 30 depicts results of a click-type reaction with three different feed ratios of azido-PTX to alkyne group on PEO-b-PBYP. Three resulting polymers with feed ratios (20%, 50% and 100% respectively) are plotted as a function of conjugation efficiency (left), PTX loading capacity (left), polymer solubility in water (right) and PTX solubility in water (right).

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to polymer-drug systems, and more particularly to nanoscopic particles comprising amphiphilic block copolymers conjugated, physically encapsulated, or otherwise combined with drugs along a selective region or regions of the backbone of the copolymer, so as to package the chemotherapeutic agent in selective domains within each nanoscopic particle, as well as to methods for making such particles, and applications and methods for using such particles.

In general, the present disclosure provides polymer-drug systems having a core-shell morphology comprising an amphiphilic block copolymer and a hydrophobic drug core. In some embodiments, the drug is attached to the polymer backbone through a covalent linkage. The covalent linkage optionally may include a cleavable linkage. For example, an ester linkage for hydrolytic cleavage (e.g., to facilitate release of the drug). In one embodiment, the linkage may include an acid-sensitive β-thioproprionate linkage, which may be used to control drug release kinetics. In other embodiments, the drug is physically encapsulated within a micelle by the polymer. The encapsulating polymers may also include a functional group useful for postmodifications such as crosslinking, dyes, imaging agents, and tuning water solubility. Such functional groups may similarly be modified using, for example, alkyne-azide, thiol-ene, or thiol-yne reactions.

One advantage of the polymer micelle modularity is the ability to tune the core and shell components. This is particularly useful for drug delivery because the core of the assembly can serve as a reservoir for a variety of therapeutic agents while the hydrophilic shell imparts solubility and stability to the aqueous assemblies. From a pharmacokinetic viewpoint, the distribution of drug-loaded micelles is largely determined by the size, shape and surface chemistry of the micelle and not by the drug itself.

Polymer-drug systems of the present disclosure offer a number of benefits. They may demonstrate, for example, ultra-high drug loading capacities and drug concentrations in water, have nanoscopic dimensions for optimized biodistribution in vivo, a well-defined core-shell morphology for packaging of the drug with covalent conjugation or physical encapsulation to avoid pre-mature drug release (including controlling drug release kinetics), hydrolytic degradability for controlled drug release and biological clearance of the nanoscopic drug delivery system, and residual reactive functionalities for additional conjugation of imaging agents, targeting ligands, and the like, or for establishing crosslinks, and the like.

In one embodiment, the present disclosure provides compositions comprising the reaction product of an amphiphilic block copolymer and a chemotherapeutic agent (e.g., PTX).

In particular embodiments, the block copolymer may comprise a hydrophilic polymer component and a hydrophobic polymer component, making the block copolymer amphiphilic. In addition, in some embodiments, either or both components may be biodegradable. For example, a hydrophilic polymer component could comprise poly(ethylene oxide) (PEO) and a hydrophobic polymer component could comprise a polyphosphoester (PPE)). Using both examples given, but not by way of limitation, then, the block copolymer may be of the form PEO-b-PPE. Either or both of the PEO and the PPE may be biodegradable—that is, the second segment of the block copolymer may comprise a degradable polyphosphoester. In general, the block copolymer may be in whole or in part degradable. Degradability in such embodiments serves the purpose of releasing the drug and allowing for biological clearance of the polymer carrier system.

In some embodiments, the hydrophilic polymer component may comprise a PPE. In addition, in some embodiments, the block copolymer may comprise more than two polymer components.

Suitable hydrophilic polymer components can be of neutral, anionic, cationic or zwitterionic charge character, and include, for example, PEO, a.k.a. polyethylene glycol (PEG), and PEG derivatives (e.g., bisamino-propyl PEG), poly(N-vinylpyrolidinone), polyacrylamide, poly(acrylic acid), polyethyleneimine, polycarboxybetaine, polysulfobetaine, and derivatives thereof. Hydrophilic polymers have an affinity for water, as measured by a low water contact angle (<30°), and/or swellability or solubility in water. The amount of hydrophilic polymer component may vary. The hydrophilic polymer component may be linear or branched. The hydrophilic polymer component may function to increase hydrophilicity and/or circulation time) of a polymer-drug system.

The biodegradable polymer backbone, as in the previously-given example, may in some embodiments be a polyphosphoester (PPE). In particular embodiments, the polymer backbone may be degradable. Furthermore, it may comprise one or more functionalities. In particular, it may comprise one or more functionalities that are capable of undergoing high efficiency reactions (e.g., click-type reactions) with a functional group on the drug (or on a functionalized drug, as discussed below). For example, an alkynyl functionality has been shown to undergo highly efficient click-type Huisgen cycloaddition reactions with an azide functionality. As another example, an alkynyl functionality may undergo a highly efficient click-type thiol-yne reaction (a.k.a. hydrothiolation) with a thiol functionality. As yet another example, an alkene functionality may undergo a highly-efficient thiol-ene click-type reaction. Accordingly, the biodegradable polymer backbone may comprise an alkynyl functionality so as to enable it to undergo a highly efficient click-type reaction with an azide-functionalized drug, and/or with a thiol-functionalized drug. It will be appreciated that any suitable complementary functional groups (e.g., those capable of reacting with each other) may be used, respectively, in the polymer backbone and the drug (or functionalized drug). Preferably, the complementary functional groups would be capable of highly efficient reactions (e.g., click-type chemical reactions) so as to set up a click or click-type chemical reaction between the second polymer segment and the drug. For example, the second polymer component may comprise an alkenyl functional group, and the chemotherapeutic agent may be functionalized with thiopropionate. Further example embodiments of the drug, and features thereof, are set out following the present discussion of the block copolymer.

In some embodiments, the block copolymer may be the reaction product of PEO and a cyclic phosphoramidate. In other embodiments, the block copolymer may be the reaction product of PEO and a phospholane. More specifically, some embodiments may utilize organocatalyzed ring-opening polymerization of the cyclic phosphoramidate or phospholane to form the block copolymer. The cyclic phosphoramidate or phospholane may further comprise a highly-reactive functional group (e.g., an alkynyl functionality). Thus, expanding on the example of the phospholane, the phospholane may comprise butynyl phospholane (BYP), or any other alkynyl phospholane, or any other phospholane comprising a reactive functionality. Combining these specific examples, then, the copolymer of some embodiments may comprise the reaction product of organocatalyzed ring-opening polymerization of butynyl phospholane and PEO, e.g., PEO-b-PBYP.

It will be appreciated, however, that any block copolymer capable of conjugation, physical encapsulation, or other combination with a chemotherapeutic agent may be used in combination with the chemotherapeutic agent. Moreover, the block copolymer may be a diblock copolymer, or a multi-block copolymer.

The chemotherapeutic agent of some embodiments may be a chemotherapeutic agent capable of reacting with a functionality of the block copolymer. In some embodiments, the chemotherapeutic agent may be functionalized in order to promote reaction with a functionality of the copolymer. More particularly, the chemotherapeutic agent may be functionalized to result in a stable covalent linkage with the copolymer by reaction with one or more functional groups of the copolymer. For example, the chemotherapeutic agent paclitaxel (PTX) may be functionalized with an azide group by reaction with PTX's most reactive 2'-hydroxyl group, forming azide-functionalized PTX. As discussed previously, azide-functionalized PTX will undergo highly efficient "click"-type Huisgen cycloaddition reactions with an alkynyl group, and therefore may be particularly suited for conjugation with a copolymer including one or more alkynyl functionalities. As another example, a thiol-funtionalized PTX prodrug may be formed by functionalizing the 2'-hydroxyl group of PTX with a thiol group. Such a thiol-functionalized PTX may undergo a highly efficient thiol-ene click-type reaction with an alkene group. In other embodiments, azide-functionalized PTX may be reacted with an alkynyl group via copper-catalyzed azide-alkyne cycloaddition, or via ruthenium-catalyzed azide-alkyne cycloaddition. In other embodiments, thiol-functionalized PTX may be reacted with an alkynyl group via thiol-yne reaction. These are merely examples of click or click-type reactions and catalysts used therein; it will be appreciated by those skilled in the art that any variety of highly efficient click or click-type reactions may be used instead of or in addition to those mentioned herein.

In certain embodiments, the functionalized chemotherapeutic agent may further include a release or cleavable element for easy release of the chemotherapeutic agent from the block copolymer. Returning to the example of an azide-functionalized PTX, the 2'-hydroxyl group of PTX may be reacted with 6-azidohexanoic acid to form an ester linkage. The ester linkage is susceptible to degradation through hydrolytic cleavage, thus releasing the PTX. An example formula of a block copolymer containing an alkynyl conjugated with an azide-functionalized PTX containing an ester linkage is shown in FIG. 1.

Figure 1:
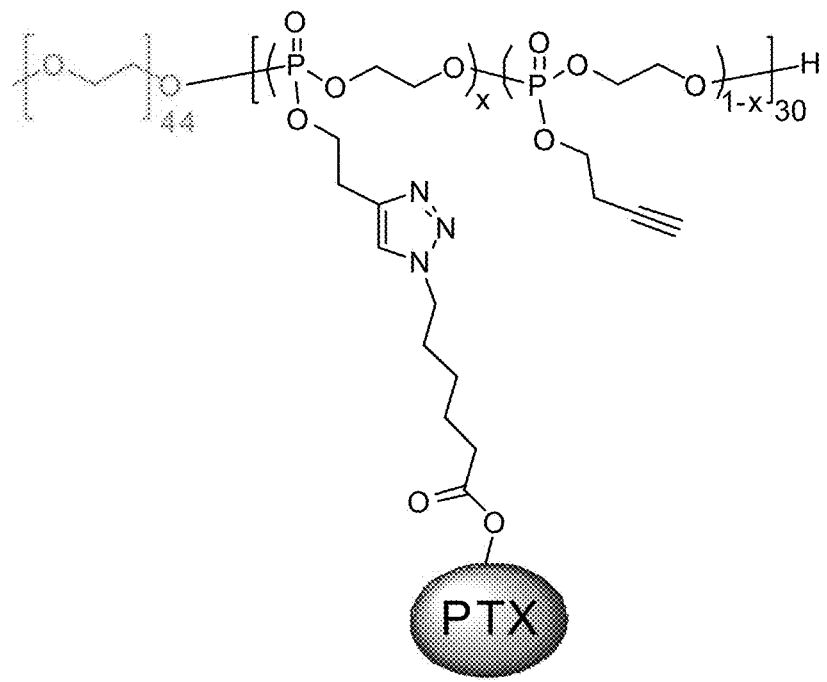
FIG. 1 depicts a block copolymer containing an alkynyl conjugated with an azide-functionalized PTX containing an ester linkage.

Note also in the example formula of FIG. 1 that the polyphosphoester to which the functionalized PTX is conjugated may also undergo degradation by hydrolysis, exhibiting the exemplar property of the polymer backbone of some embodiments discussed above. Other suitable release elements may be appended to the chemotherapeutic agent instead of or in addition to the ester linkage—for example, a redox-sensitive disulfide bond or a pH-sensitive β-thiopropionate, may be appended to the PTX. Use of pH-sensitive β-thiopropionate may allow control of drug release kinetics.

Figure 2A:
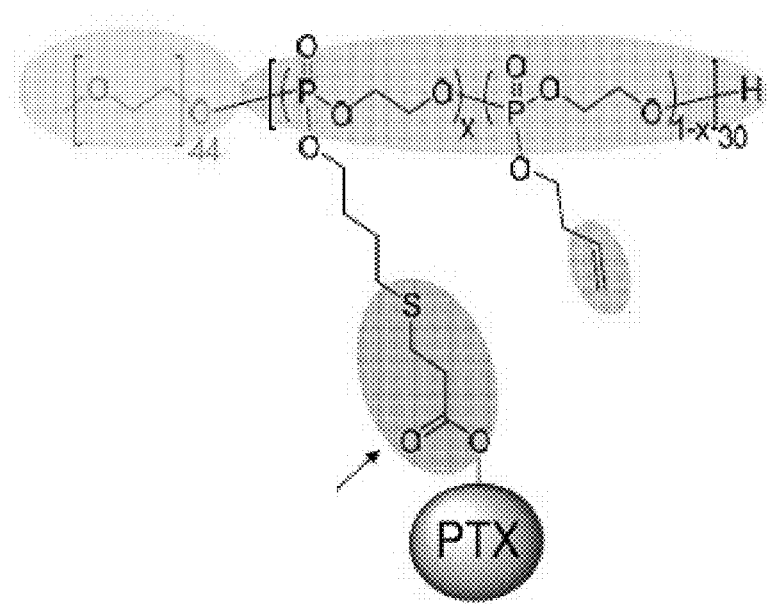
FIG. 2A depicts an embodiment in which PTX is joined to a polymer by an acid-labile thioproprionate linkage, indicated by an arrow.

Similarly, the chemotherapeutic agent may be functionalized with thiopropionic acid, as mentioned previously, which further provides for relatively easy release of the chemotherapeutic agent due to its degradability, as shown in the formula in FIG. 2A.

Figure 2B:
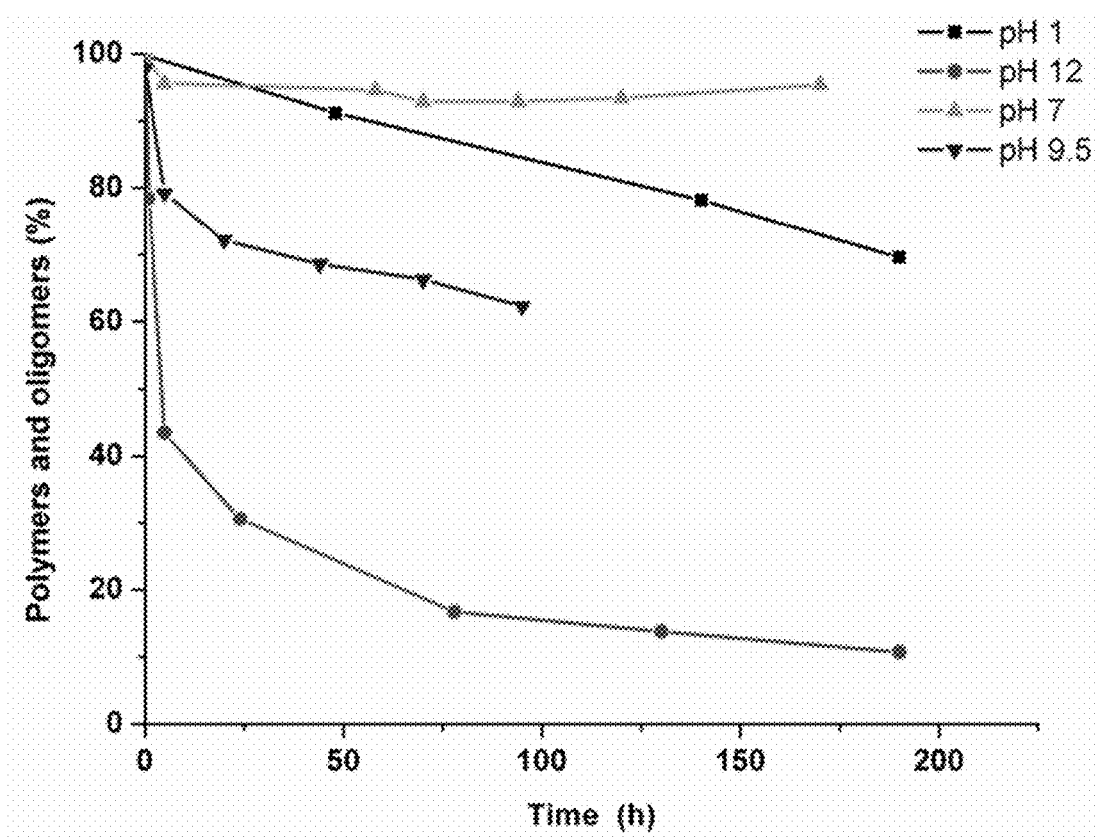
FIG. 2B depicts the percentage of polyphosphoester and oligo-phosphoester in degradation solutions of different percentages over time.

Inclusion of a release element in the functionality appended to the chemotherapeutic agent may be particularly advantageous for more efficient release of the chemotherapeutic agent from the copolymer. The release element may be tailored specifically to the particular application of the chemotherapeutic agent, e.g., by appending a degradable element that degrades specifically in the environment to which the chemotherapeutic agent is targeted. For example, the ester linkage discussed above is particularly susceptible to hydrolytic cleavage, so, a low-pH (acidic) environment would lead to more degradation as compared to a neutral pH, where degradation would be minimal or non-existent, as shown in FIG. 2B (depicting the percentage of polyphosphoester and oligo-phosphoester in degradation solutions of different percentages over time).

These properties may be particularly advantageous in some embodiments when paired with a copolymer that, as above, is similarly degradable (particularly one that degrades in like conditions, such as a low pH). In other embodiments, on the other hand, orthogonality of degradation mechanisms (e.g., with respect to the copolymer backbone and drug linkage) may be attractive. Although previously discussed in the context of a chemotherapeutic agent, the release element may, in other embodiments, be tailored specifically to the particular applications of other drugs in a similar manner.

It will be appreciated that the drug of some embodiments may be functionalized with any functional group capable of reacting with a functional group of the copolymer so as to conjugate with the copolymer along a selective region of the polymer backbone. Such functionalization of the drug may or may not include a degradable element.

The chemotherapeutic agent of other embodiments may be functionalized with any functional group compatible with encapsulation, or that enables another method of combination with the copolymer, or the agent may include no further functional group at all (e.g., if it is encapsulated by the copolymer).

In some embodiments, the copolymer-chemotherapeutic agent compound is the reaction product of the chemotherapeutic agent or functionalized chemotherapeutic agent and the block copolymer, where conjugation of the chemotherapeutic agent takes place along a selective region of the copolymer, as illustrated in the figures of Paragraphs 18, 19 and 20, above. Using the example copolymer embodiment of PEO-b-PPE, and the example embodiment of a chemotherapeutic agent comprising paclitaxel (PTX), the resulting copolymer-chemotherapeutic agent conjugate may generally be represented as PEO-b-PPE-g-PTX. Using the more specific examples of a polyphosphoester containing an alkynyl functionality, and PTX functionalized with an azide via an ester linkage, the resulting conjugate of some embodiments may be represented by the formula shown in Paragraph 18 above.

The properties of such conjugates (i.e., PEO-b-PPE-g-PTX) or other compounds formed by encapsulation or other combination may be tailored to suit a particular application by changing the polymer segment lengths and/or the ratio and reaction conditions of the various components. The properties of PEO-b-PPE-g-PTX compositions may also be varied by altering the stoichiometric ratio of the copolymer (e.g., PEO-b-PPE) to the chemotherapeutic agent (e.g., PTX). For example, such alterations may result in changes in the conjugation efficiency between the copolymer and the chemotherapeutic agent, and may also result in changes to the drug loading of the chemotherapeutic agent, or in the resulting water solubility of the entire compound.

Figure 2C:
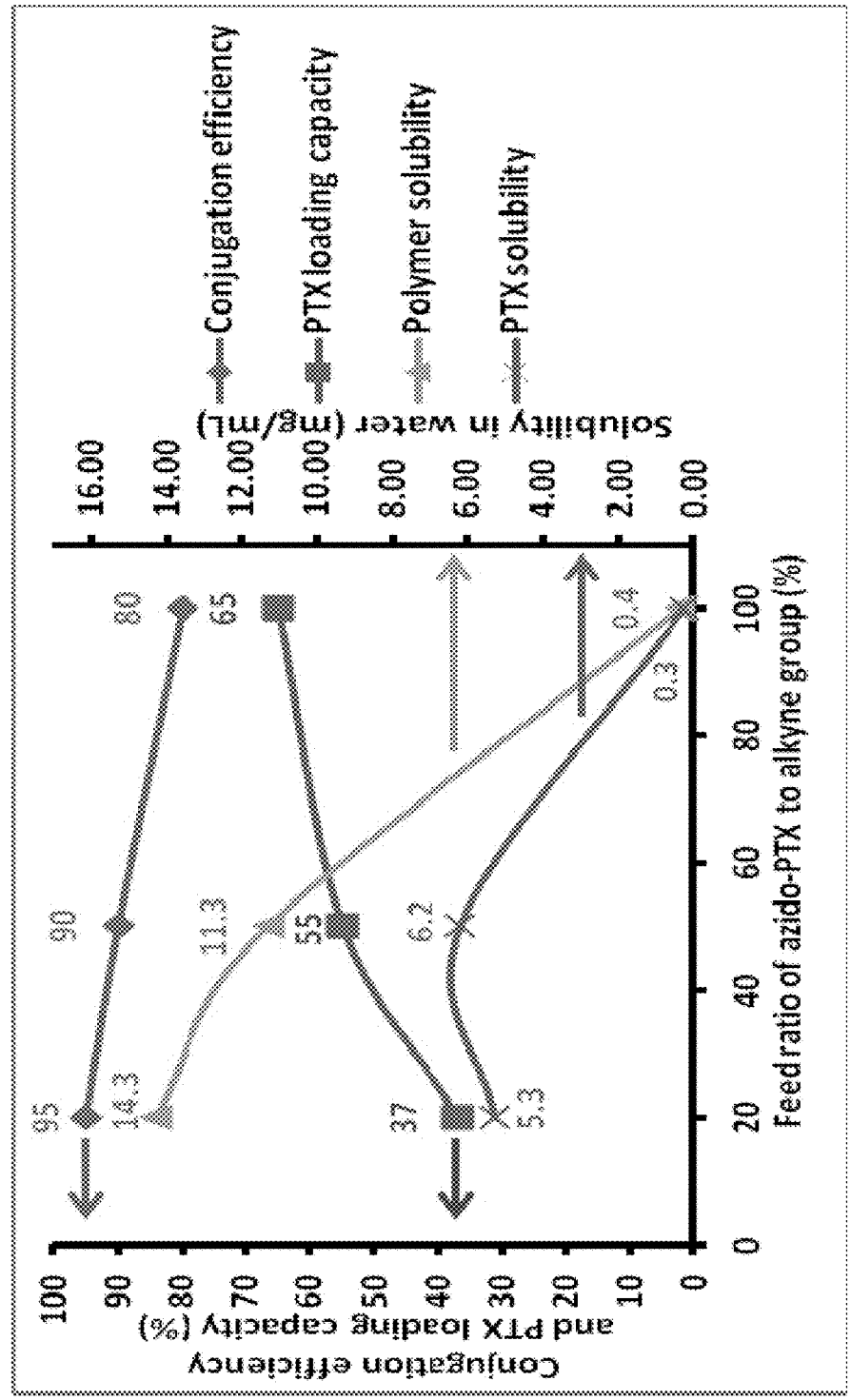
FIG. 2C depicts the effects of different feed ratios of 20%, 50%, and 100% of PTX in the reaction of azido-PTX with the block copolymer PEO-b-PBYP o PEO-b-PBYP on PTX loading capacities, solubilities, (of both the polymer and PTX), and conjugation efficiencies.
Figure 3:
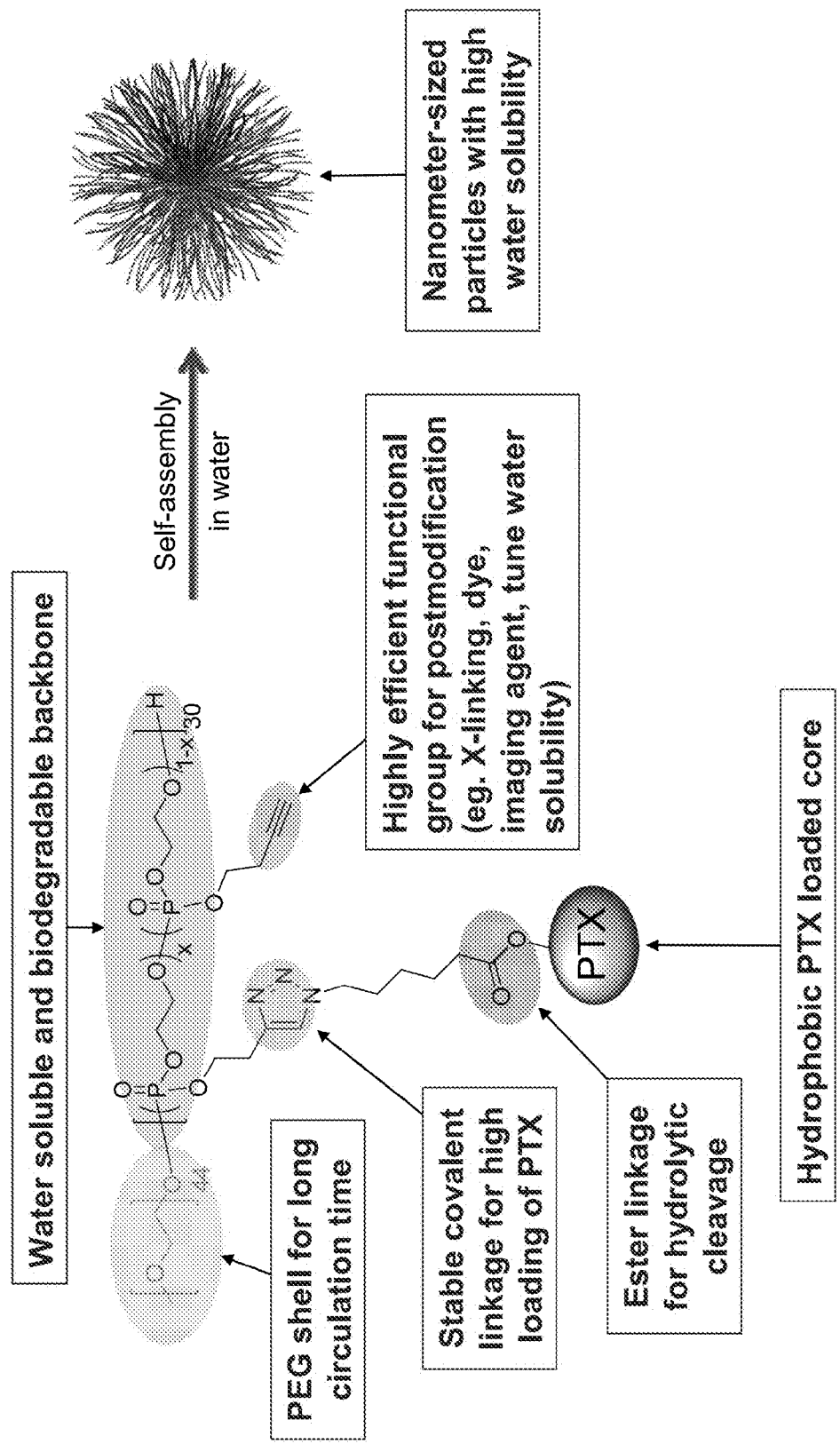
FIG. 3 depicts features of polymer and chemotherapeutic compositions of the present disclosure.

Thus, in certain embodiments, the chemotherapeutic agent loading capacity may be as high as 65 wt %, with the optimal PTX concentration being produced at 55 wt % loading in $PEO_{44}$-b-$PPE_{30}$-g-PTX, resulting in a concentration of, e.g., 6.2 mg/mL in water. For example, in the reaction of azido-PTX (a functionalized chemotherapeutic agent) with the block copolymer PEO-b-PBYP (further comprising one or more alkyne functional groups on the block copolymer backbone), different feed ratios of 20%, 50%, and 100% of PTX to PEO-b-PBYP produce different PTX loading capacities, solubilities (of both the polymer and PTX), and conjugation efficiencies, as shown in FIG. 2C. In addition, certain embodiments of the compounds of the present disclosure may be characterized by their amphiphilic core-shell nanoparticle morphology. Certain embodiments of the compounds of the present disclosure may form well-defined micelles in aqueous solution. In certain embodiments, the compounds may further include pendant reactive functional groups. These groups may be used, for example, to conjugate multiple drugs, targeting ligands, and/or imaging agents to achieve chemotherapy and bioimaging. These groups may also be used to achieve cross-linking; to attach a dye; to tune water solubility of the conjugate (e.g., by attaching PEG or PEO or other compounds, for instance neutral or charged hydrophilic small molecules or polymers); or to tune the particle size, shape, water solubility and release speed (e.g., by attaching 3-mercaptopropanoic acid). Such attachments may be made by click or click-type reactions. FIG. 3 depicts some of these features, returning to the example of PTX functionalized with an azide via a degradable ester linkage, and further conjugated with an alkynyl-containing PEO-b-PPE. Calculated PTX loading in FIG. 3 is PTX/(polymer+linkage+PTX). When X is 0.05, PTX loading is 57 wt %. When X is 1, PTX loading is 68 wt %.

Figure 4:
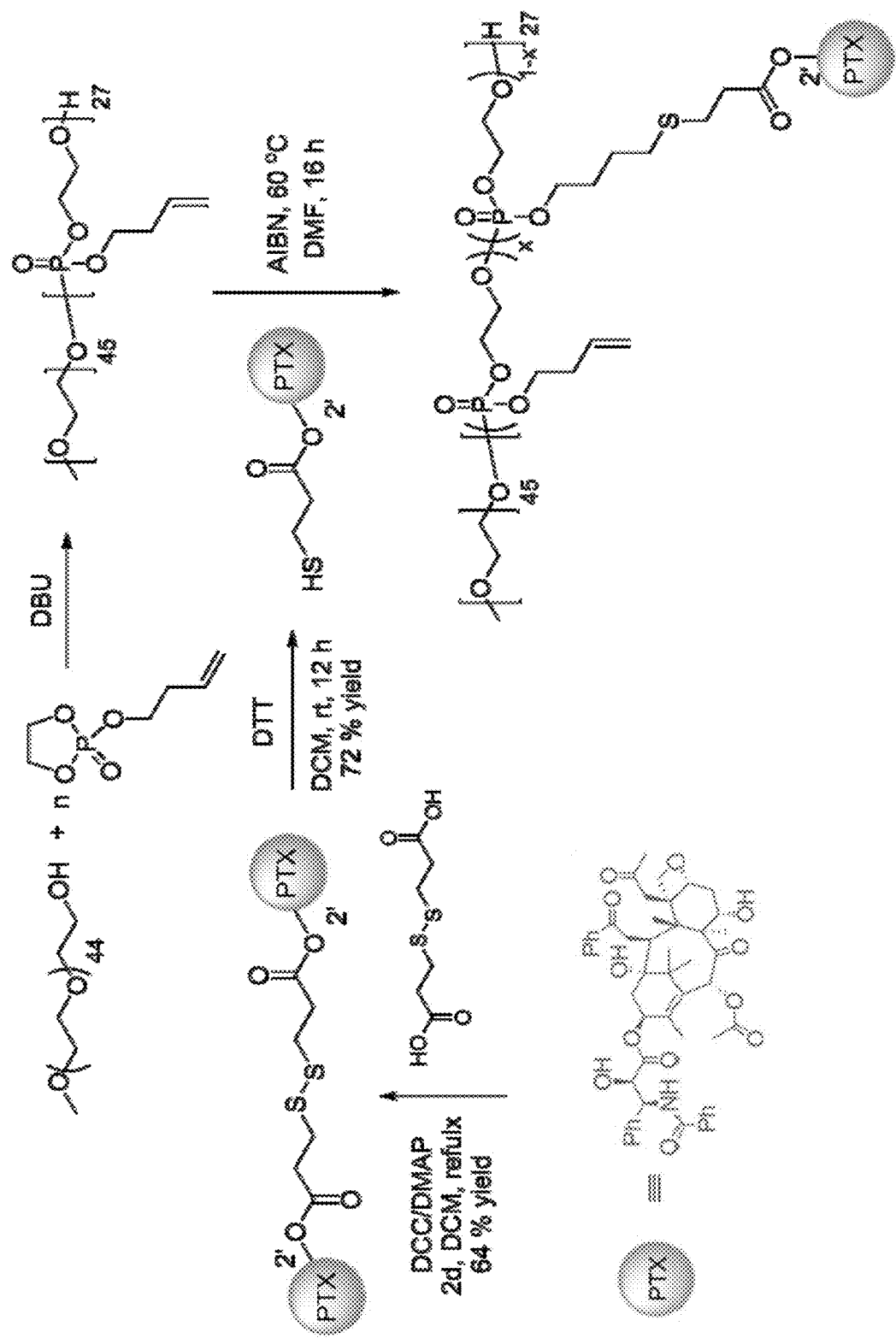
FIG. 4 depicts a synthesis scheme for PPE-PTX-G2 involving organocatalyzed ring-opening polymerization of an alkenyl-containing phospholane with PEO, followed by click-type reaction between the thiopropionate functionality of the PTX and the alkenyl functionality of the resulting copolymer.

In some embodiments, the present disclosure also provides for synthesis of copolymer-chemotherapeutic agent conjugates by a two-step process: (1) organocatalyst-promoted ring-opening-polymerization followed by (2) click-type reaction-based conjugation of a chemotherapeutic agent. Examples of organocatalyst-promoted ring-opening polymerization and of click-type reaction conjugation have previously been discussed. Returning to the example of thiopropionate-functionalized PTX, this functionalized chemotherapeutic agent can be conjugated with a copolymer by the process illustrated in FIG. 4—organocatalyzed ring-opening polymerization of an alkenyl-containing phospholane with PEO, followed by click-type reaction between the thiopropionate functionality of the PTX and the alkenyl functionality of the resulting copolymer. X is 0.063 and PTX loading is 53 wt %.

It will be appreciated that any means of forming a copolymer with a functional group useful in conjugation may be utilized in combination with a follow-up step of a conjugation reaction with a drug or a functionalized drug (e.g., a chemotherapeutic agent or functionalized chemotherapeutic agent).

In other embodiments, the present disclosure provides compositions comprising a drug (e.g., a chemotherapeutic agent) physically encapsulated by block copolymers in a core-shell morphology.

Figure 5A:
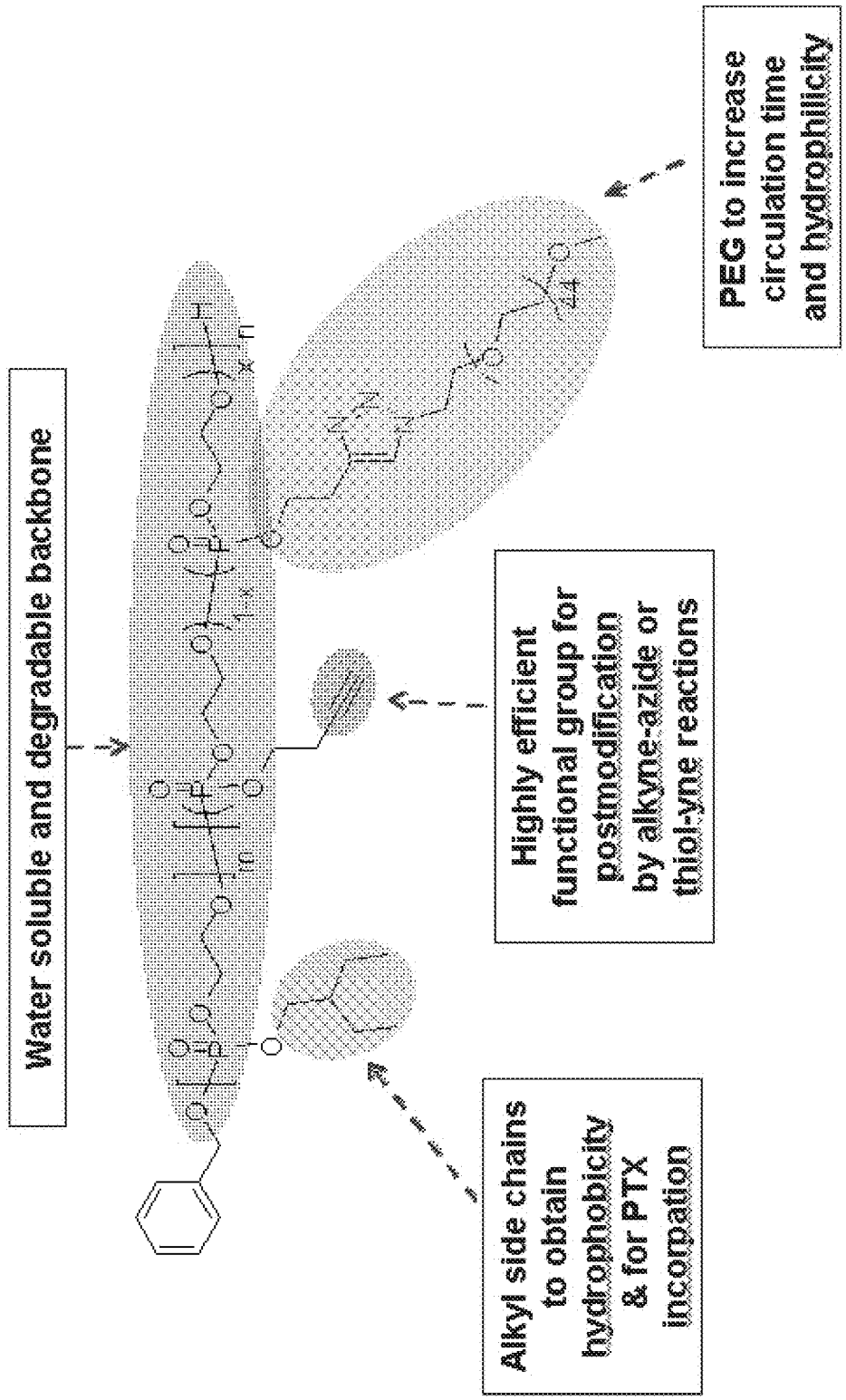
FIG. 5A depicts features of embodiments in which PEG or PEO is appended to the block copolymer via the block copolymer's functional group or groups in order to increase hydrophilicity.

The block copolymer may be any block copolymer consistent with those discussed previously. In some embodiments, the block copolymer may comprise alkyl side chains or other moieties, including conjugated drugs, dyes, or other functional units, to obtain hydrophobicity and to incorporate the chemotherapeutic agent (e.g., PTX). The block copolymer may also comprise highly efficient functional groups for postmodification (e.g., by alkyne-azide, thiol-yne, or other highly efficient reactions) Such functional groups may, for example, impart different functionalities and properties on the shell of nanoscopic micelles formed by the copolymer. In particular, in some embodiments PEG or PEO may be appended to the block copolymer via the block copolymer's functional group or groups in order to increase hydrophilicity. FIG. 5A illustrates these exemplary features of some embodiments.

Figure 5B:
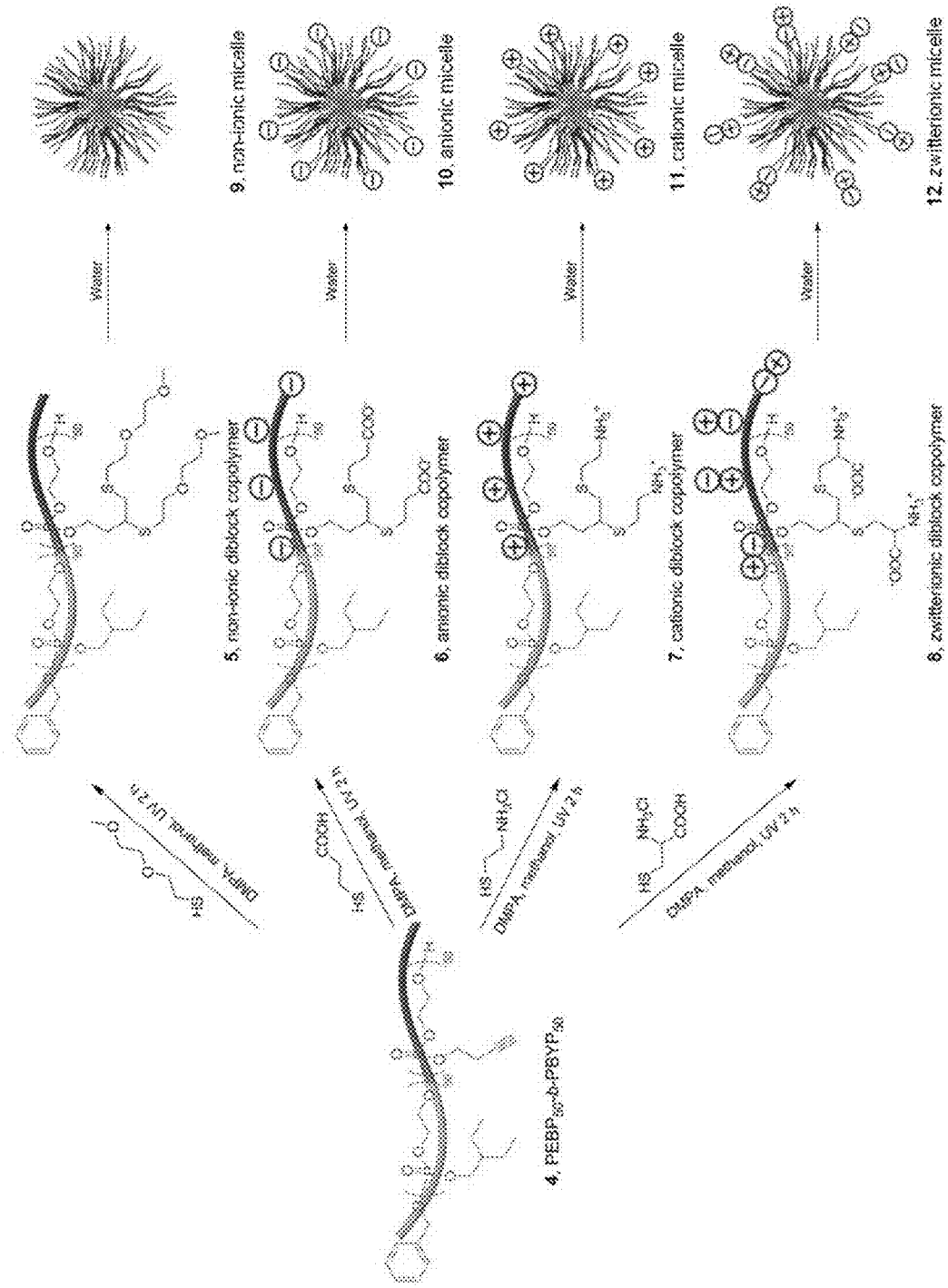
FIG. 5B depicts different charge characteristics resulting from appending different moieties to the copolymer via the copolymer's functional group or groups.

In other embodiments, different moieties may be appended to the copolymer via the copolymer's functional group or groups in order to impart different charge characteristics to the copolymer (and, in some embodiments, to the shell of the micelle formed by multiple such copolymers). As shown in FIG. 5B, such different charge characteristics may include non-ionic, anionic, cationic, and zwitterionic.

Again, a wide range of functionalities and characteristics may be imparted to the copolymer (and to micelles formed thereby) using the functional groups of the copolymer in these embodiments. Further examples include, but are not limited to, the aforementioned use of the functional groups for crosslinking, or for appending dyes, imaging agents, and moieties to tune water solubility.

Figure 5C:
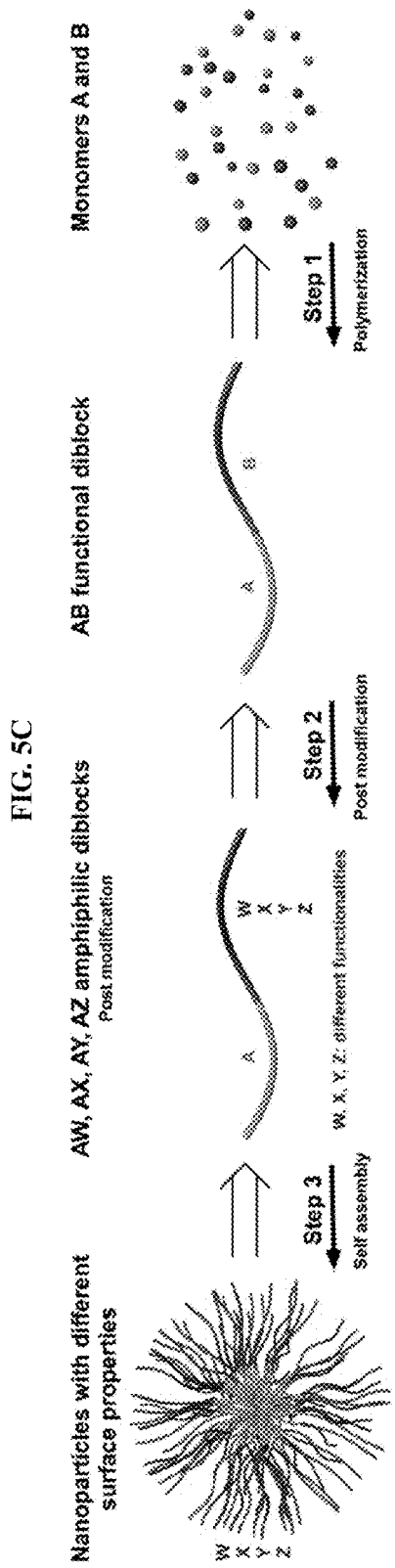
FIG. 5C depicts a reaction scheme in which a cyclic phospholane monomer carrying a functionality is synthesized and then polymerized into a functional hydrophilic block segment of the copolymer along with a hydrophobic monomer, such as 2-ethylbutyl phospholane.

Such embodiments may be formed by synthesizing monomers containing functional groups such as alkynes. The functional group-containing monomer may be synthesized as either the hydrophilic or hydrophobic component of the block copolymer. Taking the example of the hydrophilic monomer containing a functional group, a cyclic phospholane monomer carrying a functionality may be synthesized, and then polymerized into a functional hydrophilic block segment of the copolymer along with a hydrophobic monomer, such as 2-ethylbutyl phospholane. A generic depiction of this process is set forth in FIG. 5C.

In some embodiments, the block copolymer may comprise any block copolymer capable of physically encapsulating a drug, such as a chemotherapeutic agent, in a core-shell morphology (e.g., to form micelles). For example, the block copolymer may be a poly(ethylbutyl phospholane) (PEBP)-block-poly (butyryl phospholane) (PBYP), or PEBP-b-PBYP. The block copolymer, as previously stated, may further comprise additional functional groups for postmodification, e.g., for adding PEG to increase hydrophilicity.

The present disclosure also provides for methods for physical encapsulation of the drug by the block copolymer shell in a core-shell morphology (e.g., a micelle). In some embodiments, physical drug loading can be accomplished using a hydrophobic side chain to generate a hydrophobic segment of the block copolymer as discussed previously—for example, the block copolymer may comprise a hydrophobic PPE segment. In some embodiments, a drug such as a chemotherapeutic agent (e.g., PTX) may be loaded into the block copolymer micelle according to the following steps: drug and polymer are dissolved in a suitable solvent (e.g. ethanol or methanol); the solvent is removed; water is added and the mixture is sonicated. In other embodiments, the drug and polymer are dissolved in a suitable solvent (e.g. methanol or ethanol), and water is added dropwise to allow the formation of micelles, and then the organic solvent is removed by dialysis, evaporation, or other separation processes that will be apparent to one skilled in the art.

In other embodiments, a combination of drug conjugation and drug physical loading may be used to form drug-polymer micelles. For example, a hydrophobic drug (e.g., the chemotherapeutic agent PTX) may be covalently conjugated with a block copolymer according to the above disclosure. Then, additional drug may be physically loaded onto the resulting drug-polymer conjugates according to any of the physical loading methods previously discussed. See FIG. 27 for an example drug-copolymer conjugate that may be used for physical loading of additional drug into micelles formed by the drug-copolymer conjugate.

Thus, in some embodiments, physical loading of a drug (e.g., the chemotherapeutic agent PTX) may be accomplished with drug-polymer conjugates (e.g., a PTX-copolymer conjugate, such as PEO-b-PPE-g-PTX) according to the following exemplar procedure: dissolve PEO-b-PPE-g-PTX and PTX into organic solvent (e.g., acetone or DMF); perform dialysis to remove the organic solvent and trigger self-assembly of the drug-copolymers. Any other known separation mechanism can be used to remove the organic solvent, such as evaporation, distillation, etc. The resulting drug concentration may be measured, for example, by HPLC, and size measured by DLS. The resulting drug-copolymer system of these embodiments (consisting now of conjugated and physically loaded drug) may undergo lyophilization into powder and resuspension in water in a high concentration. Again, the resulting concentration may be measured, for example, by HPLC, and size measured by DLS.

In various embodiments, different concentrations of the drug may be used for physical loading with the drug-copolymer conjugate. In addition or in the alternative, the percentage of copolymer conjugated with the drug in the drug-copolymer may be altered to achieve different amounts of physical loading. Furthermore, adjusting the concentration of drug to be physically loaded and/or the percentage of conjugated drug on the copolymer may affect the properties of the resulting micelles, such as their ability to be suspended in water. Again using the example of the chemotherapeutic agent PTX, the drug-copolymer conjugate may in some embodiments be PEO-b-PPE-g-PTX, and in some embodiments may comprise 45% chemically conjugated PTX (that is, 45% of copolymers have a PTX covalently bonded to them). This 45% PTX PEO-b-PPE-g-PTXcopolymer may be physically loaded by combination with, e.g., 50% PTX, 25% PTX, or 13% PTX. Other concentrations of PTX to be physically loaded may be used. At some concentrations, the identity of the organic solvent may alter the resulting micelle size. For example, combining PEO-b-PPE-g-PTXwith 45% PTX conjugation and 50% PTX in DMF results in 80% loading efficiency and 100 nm diameter micelles. Using acetone instead of DMF may result in 45% efficiency, with size maintained at 30 nm. Reducing the concentration of PTX to be physically loaded to 13% may allow the resulting physically loaded micelles to be resuspended in water.

In other embodiments, lowering the percentage of copolymers conjugated with drugs may increase the amount of drug physically loaded onto the drug-copolymer conjugate. Returning to the PTX example just discussed, then, the amount of physically loaded PTX may be increased by decreasing the amount of PTX conjugated onto the copolymer: for example, 35% PTX conjugation results in more physical PTX loading than 45% PTX conjugation, which in turn results in more physical PTX loading than 55% PTX conjugation. See FIG. 28. It will be appreciated by one of ordinary skill in the art that, in some embodiments, the two variables discussed—amount of conjugated drug on the drug-copolymer conjugates and concentration of drug mixed with the drug-copolymer conjugates—may be adjusted to achieve various different properties of the resulting micelles (e.g., different concentrations, different sizes, different amounts of resuspension in water, etc.).

In other embodiments, a drug, such as a chemotherapeutic agent, may be loaded into shell-cross-linked nanoparticles (e.g., micelles with cross-linked shells). Cross-linking among the copolymer shell may be achieved, for example, by use of the previously mentioned highly efficient functionality on the copolymer of some embodiments. Such cross-linking may take place by thiol-yne reaction (e.g., using hexa(ethylene glycol) dithiol as a crosslinker), or by azide-alkyne reaction, or by amidation, or by any other means of cross-linking between shell copolymers. Loading a chemotherapeutic agent into a shell-cross-linked nanoparticle may take place by dissolving the agent and SCKs in a suitable solvent (e.g., methanol or ethanol), removal of the solvent, add water to the resulting SCKs and sonicate.

In certain embodiments, compositions of the present disclosure (or compositions formed by the methods of the present disclosure) may be used in chemotherapy and/or in bioimaging. In particular embodiments, these compositions may be used to treat cancerous cells, e.g., by passively or actively entering the cells and inducing cytotoxicity (e.g., by interfering with microtubules). These compositions may additionally or in the alternative be used to carry dyes or imaging agents, and may additionally latch onto target cells (e.g., cancerous cells of tumors).

In some embodiments, the compositions of the present disclosure (conjugates, physical encapsulations, and other combinations) may exist in solution form, and in particular embodiments, in aqueous solution. In other embodiments, the compositions of the present disclosure may be solids, such as a powder. The powder of some embodiments may be suspended in solution.

The present disclosure provides, in some embodiments, a new type of degradable, nanoscopic polymer assembly containing ultra-high levels of drug loading via covalent attachment and/or physical encapsulation within an amphiphilic core-shell nanoparticle morphology, which serves as an effective and safe anti-cancer agent. These compounds may be synthesized by the methods disclosed herein—in some embodiments, by a rapid, scalable and versatile approach involving only two steps: organocatalyst-promoted ring-opening polymerization followed by click-type reaction-based conjugation of a PTX prodrug or other chemotherapeutic agent. These embodiments and others of the present disclosure provide several advantages, including but not limited to: ultra-high drug loading capacities and drug concentrations in water, nanoscopic dimensions for optimized biodistribution in vivo, well-defined core-shell micelles for packaging of the drug with covalent conjugation to avoid pre-mature drug release, hydrolytic degradability for controlled drug release and biological clearance of the nanoscopic drug delivery device, and residual reactive functionalities for additional conjugation of imaging agents, targeting ligands, establishing cross-links, and other applications.

To facilitate a better understanding of the present invention, the following examples of certain aspects of some embodiments are given. In no way should the following examples be read to limit, or define, the entire scope of the invention.

EXAMPLES

Example 1

Experimental Section:
  Materials.
  N,N-dimethylformamide (DMF), ethyl acetate, acetone, diethyl ether, copper(I) bromide, acetone, diethyl ether, 1,8-diazabicyclo[5.4.0]undec-7-ene (DBU), acetic acid, 3-butyn-1-ol, triethylamine (TEA), N,N'dicyclohexylcarbodiimide (DCC), 6-bromohexanoic acid, 4-(dimethylamino) pyridine (DMAP), sodium azide, copper(II) acetate monohydrate, sodium ascorbate, N,N,N',N'',N''-pentamethyldiethylenetriamine (PMDETA), poly(ethylene glycol) methyl ether (average $M_n$~2,000 Da, PEO), methanol and 5-(iodoacetamido)fluorescein were used as received from Sigma-Aldrich Company (St. Louis, Mo.). 2-chloro-2-oxo-1,3,2-dioxaphospholane (95%) was used as received from Thermo Fisher Scientific Inc (Pittsburgh, Pa.). Paclitaxel (PTX) was used as received from Cedarburg Hauser Pharmaceuticals (Denver, Colo.). Chelex 100 Resin was used as received from Bio-Rad Laboratories (Hercules, Calif.). Tetrahydrofuran (THF) and dichloromethane (DCM) were dried through columns (J. C. Meyer Solvent Systems, Inc., Laguna Beach, Calif.). Nanopure water (18 MΩ·cm) was acquired by means of a Milli-Q water filtration system, Millipore Corp. (St. Charles, Mo.).

Instrumentation.

$^1$H NMR, $^{31}$P NMR and $^{13}$C NMR spectra were recorded on an Inova 300 MHz or Mercury 300 MHz spectrometer interfaced to a UNIX computer using VnmrJ software. Chemical shifts were referenced to the solvent resonance signals.

The DMF gel permeation chromatography (GPC) was conducted on a Waters Chromatography, Inc. (Milford, Mass.) system equipped with an isocratic pump model 1515, a differential refractometer model 2414, and a four-column set of 5 μm Guard (50×7.5 mm), Styragel HR 4 5 μm DMF (300×7.5 mm), Styragel HR 4E 5 μm DMF (300×7.5 mm), and Styragel HR 2 5 μm DMF (300×7.5 mm). The system was equilibrated at 70° C. in pre-filtered DMF containing 0.05 M LiBr, which served as polymer solvent and eluent (flow rate set to 1.00 mL/min). Polymer solutions were prepared at a concentration of ca. 3 mg/mL and an injection volume of 200 μL was used. Data collection and analysis were performed with Empower 2 v. 6.10.01.00 software (Waters, Inc.). The system was calibrated with polystyrene standards (Polymer Laboratories, Amherst, Mass.) ranging from 615 to 442,800 Da.

IR spectra were recorded on an IR Prestige 21 system (Shimadzu Corp.) and analyzed using IR solution v. 1.40 software.

Ultraviolet-visible spectroscopy (UV-vis) absorption measurements were made using a UV-2550 system (Shimadzu Corp.) equipped with a TMSPC-8 thermoelectric temperature controlling system using quartz cuvettes. Spectra were analyzed by using Tm analysis software module 1,2,1,0 and UV-Probe v. 2.33 software.

Glass transition temperatures ($T_g$) were measured by differential scanning calorimetry on a Mettler-Toledo DSC822® (Mettler-Toledo, Inc., Columbus, Ohio), with a heating rate of 10° C./min. Measurements were analyzed using Mettler-Toledo STARe v. 7.01 software. The $T_g$ was taken as the midpoint of the inflection tangent, upon the third heating scan. Thermogravimetric analysis was performed under $N_2$ atmosphere using a Mettler-Toledo model TGA/SDTA851$^e$, with a heating rate of 5° C./min. Measurements were analyzed by using Mettler-Toledo STARe v. 7.01 software.

Transmission electron microscopy (TEM) was conducted on a Hitachi H-7500 microscope, operating at 100 kV. Samples for TEM measurements were prepared as follows: 4 μL of the dilute solution (with a polymer concentration of 0.1 mg/mL) was deposited onto a carbon-coated copper grid, and after 2 min, the excess of the solution was quickly wicked away by a piece of filter paper. The samples were then negatively stained with 1 wt % phosphotungstic acid (PTA) aqueous solution. After 1 min, the excess staining solution was quickly wicked away by a piece of filter paper and the samples were left to dry under ambient conditions overnight. The average diameter of nanoparticles on TEM grid was obtained by measuring the core domain of 200 sphere particles at different area of TEM specimen and the standard deviation was presented as error.

Hydrodynamic diameters ($D_h$) and size distributions for the nanoparticles in aqueous solutions were determined by dynamic light scattering (DLS). The DLS instrumentation consisted of a Brookhaven Instruments Limited (Worcestershire, U.K.) system, including a model BI-200SM goniometer, a model BI-9000AT digital correlator, a model EMI-9865 photomultiplier, and a model 95-2 Ar ion laser (Lexel Corp.) operated at 514.5 nm. Measurements were made at 25±1° C. Scattered light was collected at a fixed angle of 90°. The digital correlator was operated with 522 ratio spaced channels, and initial delay of 5 μs, a final delay of 100 ms, and a duration of 2 min. A photomulitplier aperture of 100 μm was used, and the incident laser intensity was adjusted to obtain a photon counting of between, 200 and 300 kcps. Only measurements in which the measured and calculated baselines of the intensity autocorrelation function agreed to within 0.1% were used to calculate particle size. The calculations of the particle size distributions and distribution averages were performed with the ISDA software package (Brookhaven Instruments Company), which employed single-exponential fitting, cumulants analysis, and CONTIN particle size distribution analysis routines. Alternatively, DLS measurements were also conducted using a Delsa Nano C from Beckman Coulter, Inc. (Fullerton, Calif.) equipped with a laser diode operating at 658 nm. Size measurements were made in nanopure water. Scattered light was detected at 165° angle and analyzed using a log correlator over 70 accumulations for a 0.5 mL of sample in a glass size cell (0.9 mL capacity). The photomultiplier aperture and the attenuator were automatically adjusted to obtain a photon counting rate of ca. 10 kcps. The calculation of the particle size distribution and distribution averages was performed using CONTIN particle size distribution analysis routines using Delsa Nano 2.31 software. The peak average of histograms from intensity, volume and number distributions out of 70 accumulations were reported as the average diameter of the particles. All determinations were repeated 5 times. Hydrodynamic diameters ($D_h$) and size distributions for the nanoparticles in aqueous solutions were determined by dynamic light scattering (DLS). DLS measurements were conducted using a Delsa Nano C from Beckman Coulter, Inc. (Fullerton, Calif.) equipped with a laser diode operating at 658 nm. Size measurements were made in nanopure water. Scattered light was detected at 165° angle and analyzed using a log correlator over 70 accumulations for a 0.5 mL sample in a glass size cell (0.9 mL capacity). The photomultiplier aperture and the attenuator were automatically adjusted to obtain a photon counting rate of ca. 10 kcps. Calculation of the particle size distribution and distribution averages was performed using CONTIN particle size distribution analysis routines using Delsa Nano 2.31 software. The peak averages of histograms from intensity, volume and number distributions out of 70 accumulations were reported as the average diameter of the particles. All determinations were repeated 5 times.

The zeta potential values of the nanoparticles were determined by Delsa Nano C particle analyzer (Beckman Coulter. Fullerton, Calif.) equipped with a 30 mW dual laser diode (658 nm). The zeta potential of the particles in suspension was obtained by measuring the electrophoretic movement of charged particles under an applied electric field. Scattered light was detected at a 30° angle at 25° C. In each measurement, NaCl solution was added to adjust the sample to 10 mM. The zeta potential was measured at five regions in the flow cell and a weighted mean was calculated. These five measurements were used to correct for electroosmotic flow that was induced in the cell due to the surface charge of the cell wall. All determinations were repeated 5 times.

Synthesis of 6-azidohexanoic acid.

In a 100 mL round-bottom flask equipped with a magnetic stirring bar, 6-bromohexanoic acid (3.88 g, 20 mmol) and sodium azide (2.6 g, 40 mmol) were added and dissolved in DMF (20 mL). After being stirred under room temperature for 36 h, the reaction mixture was added 30 mL DCM and then extracted with water (30 mL), brine (30 mL) and saturated NaHCO$_3$ aqueous solution (30 mL) respectively. The combined organic layers were dried over MgSO$_4$ and filtered. The filtrate was concentrated in vacuo, and the resulting mixture was purified by column chromatography on silica gel using hexane/EtOAc gradient as eluent and gave 6-azidohexanoic acid as a pale yellow liquid (2.48 g, yield: 79%) $^1$H NMR (CDCl$_3$, ppm): δ 1.42 (m, 2H, N$_3$CH$_2$CH$_2$CH$_2$CH$_2$), 1.64 (m, 4H, N$_3$CH$_2$CH$_2$CH$_2$CH$_2$), 2.36 (t, 2H, J=7 Hz, CH$_2$CH$_2$COOH), 3.27 (t, 2H, J=7 Hz, N$_3$CH$_2$CH$_2$CH$_2$), 9.70 (br, 1H, COOH). $^{13}$C NMR (CDCl$_3$, ppm): δ 24.2, 26.1, 28.5, 33.8, 51.2, 178.9. FT-IR (cm$^{-1}$): 3600-3100, 2931, 2092, 1700, 1242, 941. HRMS: calculated [M−H]$^-$ for C$_6$H$_{10}$N$_3$O$_2$: 156.0773. found: 156.0777.

Synthesis of azido-PTX, 4.

In a 25-mL round flask equipped with a magnetic stirring bar, 6-azidohexanoic acid (204 mg; 1.3 mmol) and PTX (920 mg; 1.08 mmol) were added and dissolved in dichloromethane (10 mL). After stirring at r.t. for 1 h, DCC (268 mg; 1.30 mmol) and DMAP (27 mg; 0.23 mmol) were added. The mixture was heated to reflux for 3 days, filtrated, concentrated, and then separated by flash chromatography using silica gel with hexane and ethyl acetate as eluent in gradient (until hexane/ethyl acetate=50/50, v/v) and gave the targeted compound as a pale yellow solid (840 mg, Yield: 78.3%). $^1$H NMR (CDCl$_3$, ppm): δ 1.13 (s, 3H, (C-16)-CH$_3$), 1.25-1.40 (m, 5H, (C-17)-CH$_3$ and N$_3$CH$_2$CH$_2$CH$_2$CH$_2$), 1.50-1.70 (m, 7H, (C-19)-CH$_3$ and N$_3$CH$_2$CH$_2$CH$_2$CH$_2$), 1.82-1.95 (m, 5H, (C-6)-CH, 1-OH and (C-18)-CH$_3$), 2.15 (m, 1H, (C-14)-CH), 2.23 (s, 3H, 10-OAc), 2.34-2.62 (m, 8H, 4-OAc, (C-6)-CH, (C-14)-CH, 7-OH and CH$_2$CH$_2$COO(PTX)), 3.21 (t, 2H, J=7 Hz, N$_3$CH$_2$CH$_2$CH$_2$), 3.81 (d, 1H, J=7 Hz, (C-3)-CH), 4.20 (d, 1H, J=8 Hz, (C-20)-CH), 4.31 (d, 1H, J=8 Hz, (C-20)-CH), 4.46 (m, 1H, (C-7)-CH), 4.94 (dd, 1H, J=9 Hz, J=2 Hz, (C-5)-CH), 5.51 (d, 1H, J=3 Hz, (C-2')-CH), 5.68 (d, 1H, J=7 Hz, (C-2)-CH), 5.95 (dd, 1H, J=9 Hz, J=3 Hz, (C-3')-CH), 6.23-6.29 (m, 2H, (C-10)-CH and (C-13)-CH), 6.85 (d, 1H, J=9 Hz, 3'-NH), 7.34-7.64 (m, 11H, PhH), 7.73 (d, 2H, J=8 Hz, PhH), 8.14 (d, 2H, J=8 Hz, PhH). $^{13}$C NMR (CDCl$_3$, ppm): δ 9.6, 14.9, 20.9, 22.2, 22.7, 24.2, 26.0, 28.4, 33.5, 35.6, 43.2, 45.6, 51.1, 52.8, 58.5, 71.8, 72.2, 73.9, 75.1, 75.6, 76.5, 79.2, 81.1, 84.5, 126.5, 127.1, 128.5, 128.8, 129.1, 129.2, 130.3, 132.1, 132.8, 133.7, 137.0, 142.8, 167.1, 168.1, 169.8, 171.3, 172.5, 203.9. FT-IR (cm$^{-1}$): 2939, 2098, 1782, 1659, 1528, 1450, 1365, 1234, 1065, 980, 902, 794. HRMS: calculated [M+Li]$^+$ for C$_{53}$H$_{60}$N$_4$O$_{15}$Li: 999.4215. found: 999.4187.

Synthesis of butynyl pholane (BYP, 2) Monomer.

To a stirred solution of 3-butyn-1-ol (7.40 g, 106 mmol) and triethylamine (11.7 g, 116 mmol) in 200 mL of anhydrous THF at 0° C. were dropwisely added a solution of COP (15.1 g, 106 mmol) in 50 mL of anhydrous THF, and the reaction mixture was allowed to stir for 12 h. After complete conversion of COP, as confirmed by TLC, the reaction mixture was filtered and the filtrate was concentrated. The concentrated filtrate was distilled under reduced pressure to obtain a faint yellow and viscous liquid (121-124° C., 0.4 mmHg, 12.1 g, Yield: 65%). $^1$H NMR (CDCl$_3$, ppm): δ 2.05 (s, 2H, POCH$_2$CH$_2$C≡CH), 2.62 (t, J=6.0 Hz, 2H, POCH$_2$CH$_2$), 4.27-4.20 (m, 2H, POCH$_2$CH$_2$C), 4.49-4.37 (m, 4H, POCH$_2$CH$_2$OP). $^{13}$C NMR (CDCl$_3$, ppm): δ 20.7, 66.2, 70.6, 79.1. $^{31}$P NMR (CDCl$_3$, ppm): δ 17.32. HRMS: calculated [M+H]$^+$ for C$_6$H$_{10}$O$_4$P: 177.0317. found: 177.0308. IR (cm$^{-1}$): 3350-3175, 3050-2850, 1474, 1280, 1011, 926, 841, 748.

Synthesis of PEO-b-PBYP, 3.

A solution of BYP (0.528 g, 3.0 mmol) and PEO (0.200 g, 0.1 mmol) in anhydrous dichloromethane (0.7 mL) was transferred into a flame-dried 5-mL shell vial equipped with a rubber septum and a stir bar. At 25° C., a solution of DBU (0.023 g, 0.15 mmol) in anhydrous dichloromethane (0.1 mL) was injected into the vial via syringe, while being maintained under a nitrogen gas atmosphere. After being stirred for 4 min, the reaction vial was unstoppered and a solution of acetic acid (excess) in dichloromethane was added via pipet into the reaction mixture to quench the reaction. After the reaction was quenched, the conversion was monitored by $^{31}$P NMR and reached 99%. The PEO-b-PBYP, 3 was purified by precipitation from dichloromethane into diethyl ether (3×), and was then dried under vacuum, to give an average yield of 80%. $^1$H NMR (CDCl$_3$, ppm): δ 2.18-2.02 (br, POCH$_2$CH$_2$C≡CH), 2.66-2.54 (br, POCH$_2$CH$_2$C≡CH), 3.36 (s, CH$_2$CH$_2$OCH$_3$), 3.87-3.49 (br, CH$_2$OCH$_2$CH$_2$OCH$_2$), 4.43-3.87 (br, POCH$_2$CH$_2$OP, POCH$_2$CH$_2$C). $^{13}$C NMR (CDCl$_3$, ppm): δ 20.5, 65.8-66.3, 69.9, 70.8, 79.5. $^{31}$P NMR (CDCl$_3$, ppm): δ −1.73. GPC: M$_n$=12200 g/mol, PDI=1.17. DSC: T$_g$=−34.2° C., T$_m$=−37.1° C. TGA in N$_2$: 50-270° C., 37% mass loss; 270-340° C., 33% mass loss, 30% mass remaining above 600° C. IR (cm$^{-1}$): 3700-3100, 3100-2750, 1643, 1428, 1353, 966, 810.

Synthesis of PEO-b-(PTX-g-PBPY), 5.

In a 10-mL Schlenk flask equipped with a magnetic stirring bar, PEO$_{2k}$-b-PBYP$_{30}$, 3 (73 mg; 0.01 mmol), azido PTX, 4 (150 mg; 0.15 mmol), CuBr (21.6 mg; 0.15 mmol) and PMDETA (26.7 mg; 0.15 mmol) were added and dissolved in DMF (1 mL). The reaction mixture was deoxygenated by freeze-pump-thaw (4×) and then placed in a preheated reaction bath at 40° C. After 24 h, the resulting mixture was precipitated from acetone into ethyl ether (3×) to remove unreacted azide-functionalized PTX. The crude product was collected and dissolved in 10 mL acetone formed clear solution. The acetone solution was transferred to dialysis tubing (MWCO: 8 kDa) and dialyzed against nanopure water with the existence of Chelex 100 resin (100-200 mesh) for 2 days, to remove copper ion and trigger self-assembly. A bluish-colored micelle solution was obtained and then passed through a 450 nm polypropylene filter to get rid of dust and large aggregates. The micelle solution was lyophilized to give a faint yellow powder with a yield of 90%. $^1$H NMR (CDCl$_3$, ppm): δ 1.14-2.80 (broad multiple peaks, protons from PTX and CH$_2$C≡CH), 2.91 (br, CH$_2$C≡CH), 3.05 (br, N$_3$CH$_2$CH$_2$CH$_2$), 3.37 (s, 3H, PEO-OCH$_3$), 3.64 (br, CH$_2$ from PEO), 3.75 (br, CH from PTX(C-3)-CH), 3.82-4.60 (br, POCH$_2$CH$_2$ from PPE backbone and POCH$_2$CH$_2$CCH from side chain), 4.90 (br, CH from PTX(C-5)-CH), 5.50 (br, CH from PTX(C-2')-CH), 5.62 (br, CH from PTX(C-2)-CH), 5.92 (br, CH from PTX(C-3')-CH), 6.19 (br, CH from PTX(C-13)-CH), 6.32 (br, CH from PTX(C-10)-CH), 7.28-7.68 (br, PhH from PTX), 7.77 (br, PhH from PTX), 8.13 (br, PhH from PTX). $^{31}$P NMR (CDCl$_3$, ppm): δ −1.72. $^{13}$C NMR (75 MHz, CDCl$_3$, 25° C., ppm): δ 9.7, 14.8, 20.9, 22.8, 23.9, 25.7, 26.7, 29.8, 33.3, 35.3-35.9 (multiple overlapping br), 43.2, 45.8, 49.9, 53.4, 58.4, 66.3-67.1 (multiple overlapping br), 70.5, 71.9, 74.0, 75.0, 78.9, 81.0, 84.4, 126.5-129.3 (multiple overlapping br), 130.2, 132.3, 132.8, 133.7, 137.0, 142.3, 166.9, 167.3, 170.0, 171.0, 172.4, 203.7. GPC:

$M_n$=18900 g/mol, PDI=1.12. FT-IR (cm$^{-1}$): 3550-3100, 2940, 1728, 1643, 1450, 1366, 1242, 1072, 1026, 980, 802. TGA in $N_2$: 200-420° C., 60% mass loss; 40% mass remaining above 420° C.

Synthesis of 5-(azidoacetamido)-fluorescein, 6.

In a 10 mL round-bottom flask equipped with a magnetic stirring bar, 5-(iodoacetamido)fluorescein (100 mg, 0.19 mmol) and sodium azide (35.0 mg, 0.53 mmol) were added and suspended in DMF (5 mL). After being stirred under room temperature for 24 h, the DMF was removed by vacuum pump. The mixture was suspended into 30 mL 0.1 M HCl solution. The aqueous phase was extracted with 30 mL ethyl acetate for 4 times. The combined organic layers were dried over $MgSO_4$ and filtered. The filtrate was concentrated in vacuo and gave a yellow solid as the crude product (84 mg, yield: 98%). The product was dissolved in 8 mL DMF and stored at −20° C. $^1$H NMR (DMSO-d6, ppm): δ 4.28 (s, 2H, $CH_2N_3$), 6.70 (m, 4H, Ar—H), 6.82 (d, m, 2H, Ar—H), 7.33 (m, 2H, Ar—H), 8.05 (m, 1H, Ar—H), 8.52 (s, 1H, CONH), 10.67 (br, 1H, Ar—OH), 11.22 (s, 1H, COOH). HRMS: calculated [M+H]$^+$ for $C_{22}H_{15}N_4O_6$: 431.0991. found: 431.0620. UV-vis: ($H_2O$) $\lambda_{max}$=491.0 nm. Fluorescence: ($H_2O$, pH=8.4) $\lambda_{em}$=522.0 nm.

Synthesis of Fluorescein labeled PEO-b-(PTX-g-PBPY), 7.

Figure 5D:
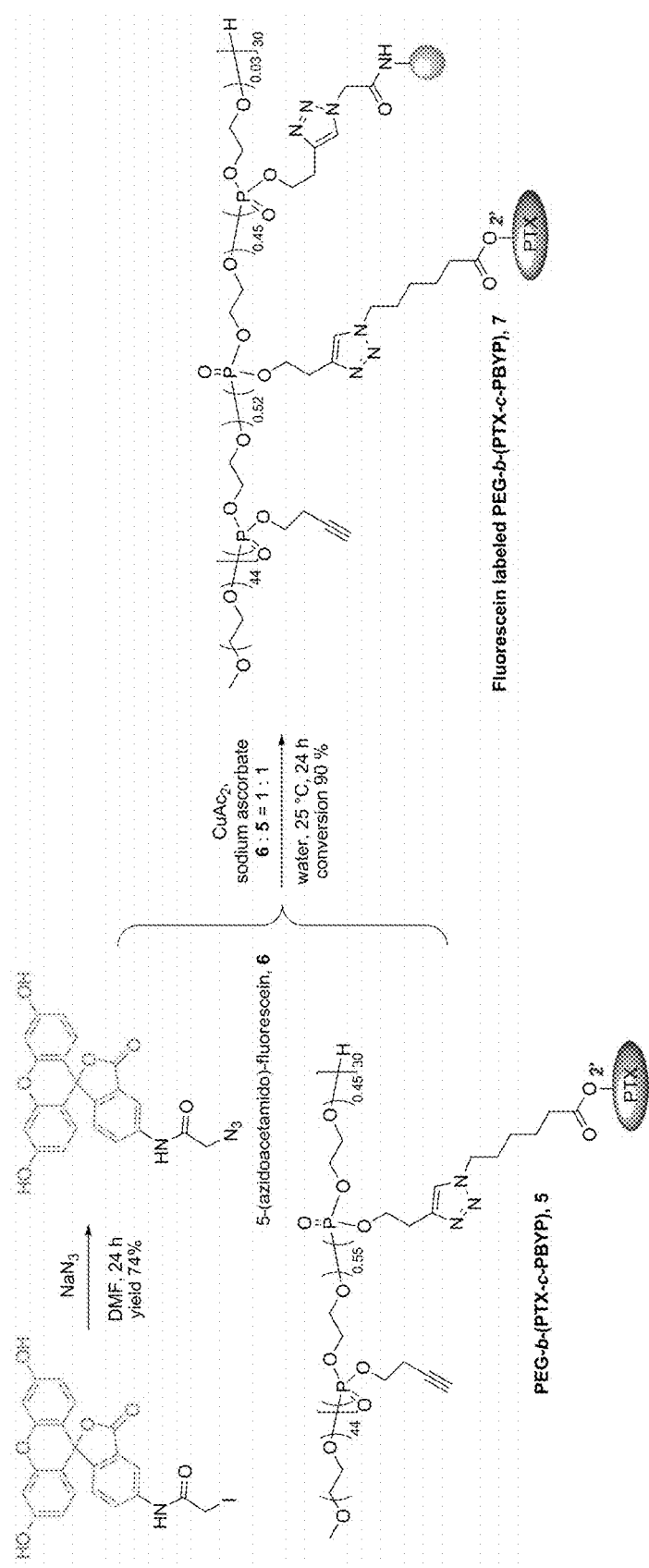
FIG. 5D depicts synthesis of fluorescein labeled PEO-b-(PTX-g-PBPY).

To an aqueous solution of the PEO-b-(PTX-g-PBPY) (1.1 mL, 4 mL) was added a solution of 5-(azidoacetamido)-fluorescein (10 mg/mL, 9 μL, 1 dye per polymer) in DMF, a solution of copper(II) acetate monohydrate (21 mM, 10 μL) and solution of sodium ascorbat (41 mM, 10 μL). See FIG. 5D. The reaction mixture was allowed to stir for 1 days and was then transferred to presoaked dialysis tubing (MWCO ca. 6000-8000 Da) and extensively dialyzed against nanopure water with the existence of Chelex 100 resin (100-200 mesh) for 3 days to remove excess dye and copper catalyst. $D_h$ (DLS, intensity)=128±93 nm; $D_h$ (DLS, volume)=40±23 nm; $D_h$ (DLS, number)=28±8 nm. UV-vis: ($H_2O$) $\lambda_{max}$=489.0 nm. Fluorescence: ($H_2O$, pH=8.4) $\lambda_{em}$=523.0 nm.

Synthesis of the Control Polymer, 8.

Figure 5E:
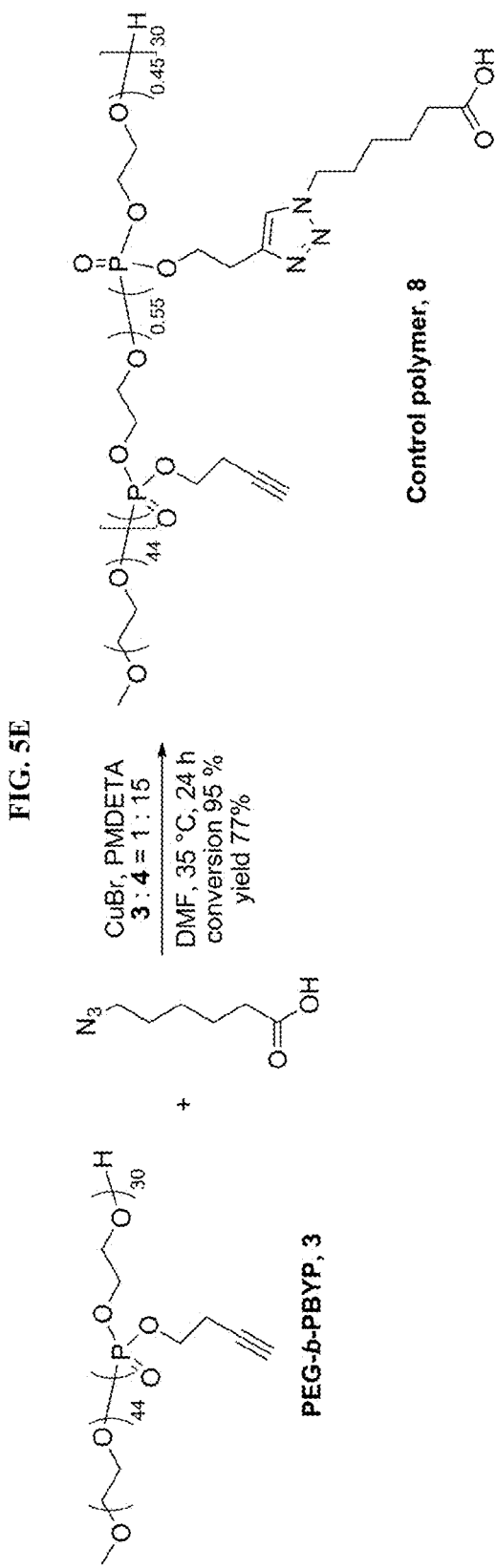
FIG. 5E depicts synthesis of a control polymer.

In a 10-mL Schlenk flask equipped with a magnetic stirring bar, $PEO_{2k}$-b-$PBYP_{30}$, 3 (100 mg; 0.013 mmol), 6-azidohexanoic acid (32.4 mg; 0.20 mmol), CuBr (28.4 mg; 0.20 mmol) and PMDETA (35.2 mg; 0.20 mmol) were added and dissolved in DMF (4 mL). See FIG. 5E. The reaction mixture was deoxygenated by freeze-pump-thaw (4×) and then placed in a preheated reaction bath at 35° C. After 24 h, the resulting mixture was transferred to dialysis tubing (MWCO: 3500 Da) and dialyzed against nanopure water with the existence of Chelex 100 resin (100-200 mesh) for 3 days, to remove copper ion and unreacted 6-azidohexanoic acid. The solution was lyophilized to give a faint yellow solid (102 mg, yield: 77%). $^1$H NMR (CDCl$_3$, ppm): δ 1.24-1.89 (br, $CH_2CH_2CH_2CH_2CH2COOH$), 2.24-2.02 (br, $POCH_2CH_2C\equiv CH$), 2.40-2.52 (br, $CH_2CH_2COOH$), 2.69-2.54 (br, $POCH_2CH_2C\equiv CH$), 3.09 (br, $N_3CH_2CH_2CH_2$), 3.38 (s, $CH_2CH_2OCH_3$), 3.85-3.52 (br, $CH_2OCH_2CH_2OCH_2$), 4.82-3.85 (br, $POCH_2CH_2OP$, $POCH_2CH_2C$), 7.76 (s, HC(=N)). $^{31}$P NMR (CDCl$_3$, ppm): δ −1.71. $^{13}$C NMR (CDCl$_3$, ppm): δ 20.6, 24.3, 26.4, 28.9, 34.1, 59.1, 66.5-65.8, 70.6, 79.5, 165.0. FT-IR (cm$^{-1}$): 3600-3200, 3150-2850, 1700, 1454, 1255, 842. DSC: $T_g$=−37.5° C., $T_m$=−43.7° C. TGA in $N_2$: 100-250° C., 9% mass loss; 250-420° C., 46% mass loss, 45% mass remaining above 420° C.

Cytotoxicity Assays:

OVCAR-3 and RAW 264.7 Cell Lines.

Human ovarian adenocarcinoma cells (OVCAR-3) (5×10$^3$ cells/well) and RAW 264.7 mouse macrophages (2×10$^4$ cells/well) were plated in 96-well plate in RPMI-1640 medium and Dulbecco's Modified Eagle's Medium (DMEM) (20% and 10% fetal bovine serum, for the OVCAR-3 and RAW 264.7, respectively and 1% penicillin/streptomycin). Cells were incubated at 37° C. in a humidified atmosphere containing 5% $CO_2$ for 24 h to adhere. Then, the medium was replaced with a fresh medium 1-h prior to the addition of the various formulations at concentrations ranged from 1×10$^{-4}$ to 60 μM of paclitaxel. The paclitaxel conjugate was prepared as described previously, and the Taxol®-mimicking formulation was prepared in similar composition to Taxol® (i.e. Cremophor-EL and ethanol, 1:1 v/v). For each well, 20 μL of every formulation was added to 100 μL of the medium. The cells were incubated with the formulations for 72 h and washed once with phosphate-buffered saline (PBS) and 100 μL of the complete medium was added to the cells. 20 μL of the MTS combined reagent was added to each well (Cell Titer 96® Aqueous Non-Radioactive Cell Proliferation Assay, Promega Co., Madison, Wis.). The cells were incubated with the reagent for 3 h at 37° C. in a humidified atmosphere containing 5% $CO_2$ protected from light. Absorbance was measured at 490 nm using SpectraMax M5 (Molecular Devices Co., Sunnyvale, Calif.). The cell viability was calculated based on the relative absorbance to the control untreated cells. The $IC_{50}$ values were calculated using GraphPad Prism four-parameter fit, considering the 0% and 100% viabilities correspond to the medium control (no cells) and cells-treated with PBS, respectively.

KB and A549 Cell Lines.

Polymer paclitaxel and free paclitaxel were tested in KB cells, a human nasal pharyngeal cancer cell line and A549 cells, a human lung carcinoma cell line. KB and A549 cells (ATCC, Manassas, Va.) were maintained in monolayer cultures in folate free RPMI (Life Technologies, Carlsbad, Calif.) and F-12K media (Mediatech, Manassas, Va.) respectively, supplemented with 10% fetal bovine serum and penicillin/streptomycin antibiotics. For screening purposes 2,500 cells in 100 μL of complete cell culture media were plated in a 96 well plate (Corning, Lowell, Mass.) in triplicates and were then incubated for 24 h in a humidified $CO_2$ cell culture incubator maintained at 37° C. Serial dilutions of polymer-paclitaxel conjugates and paclitaxel were prepared in PBS and added to cells in a volume of 10 μL. The cells were either incubated for a short period of 2 h or for longer continuous incubation of 72 h. After 2 h incubation, the media was replaced with 110 μL of fresh complete RPMI. Cell viability was assessed by using a colorimetric WST-1 cell proliferation kit (Roche, Indianapolis, Ind.) and following manufacturer's instructions. Cell viability was calculated as a percentage of the control cells treated with no drugs. The % cell viability assay values were then plotted in Graph Pad Prism (GraphPad Software Inc, La Jolla, Calif.) and the $IC_{50}$ values for each compound were obtained using non linear regression 4 parameter curve fit.

Laser Scanning Confocal Microscopy (LSCM):

RAW 264.7 and OVCAR-3 (1×10$^5$ cells/well) cells were plated in six-well glass-bottom plates (MatTek Co., Ashland, Mass.) in DMEM and RPMI-1640 medium, respectively. Cells were incubated at 37° C. in a humidified atmosphere containing 5% $CO_2$ for 24 h to adhere. Then, the medium was replaced with a fresh medium 1-h prior to the addition of the fluorescein-labeled nanoparticles (final paclitaxel concentrations of 0.5 µM for OVCAR-3 and 3 or 15 µM for RAW 264.7). The cells were incubated with the formulation for 5 h and washed extensively with PBS. Then, DRAQ-5 (Biostatus Ltd., Shepshed, Leicestershire, UK) was utilized to stain the nucleus (30-min incubation, followed by extensive washing with PBS). The cells were then fixed with 1% formaldehyde for 20 minutes, washed once with PBS. The cells were then stored in 1 mL PBS in the refrigerator. The cellular uptake of the nanoparticles was investigated by LSCM (LSM 510, Zeiss, Jena, Germany). The images were collected under the same conditions (e.g. laser power and detector gain) for consistency, and $\lambda_{excitation}$ and $\lambda_{emission}$ of 488 and 633 nm were utilized for the fluorescein and DRAQ-5, respectively.

Figure 6A:
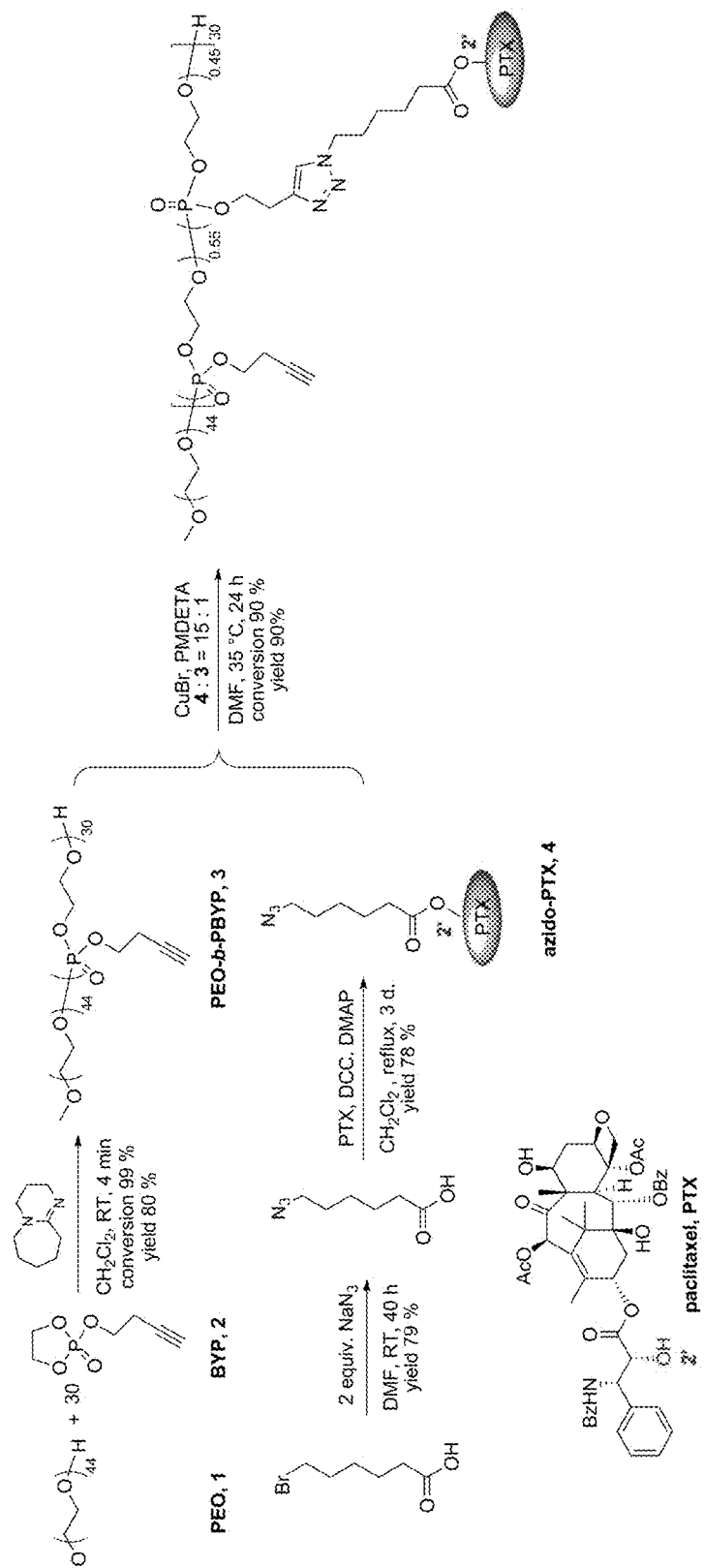
FIG. 6A depicts the synthesis of PEO-b-(PTX-g-PBYP).
Figure 6B:
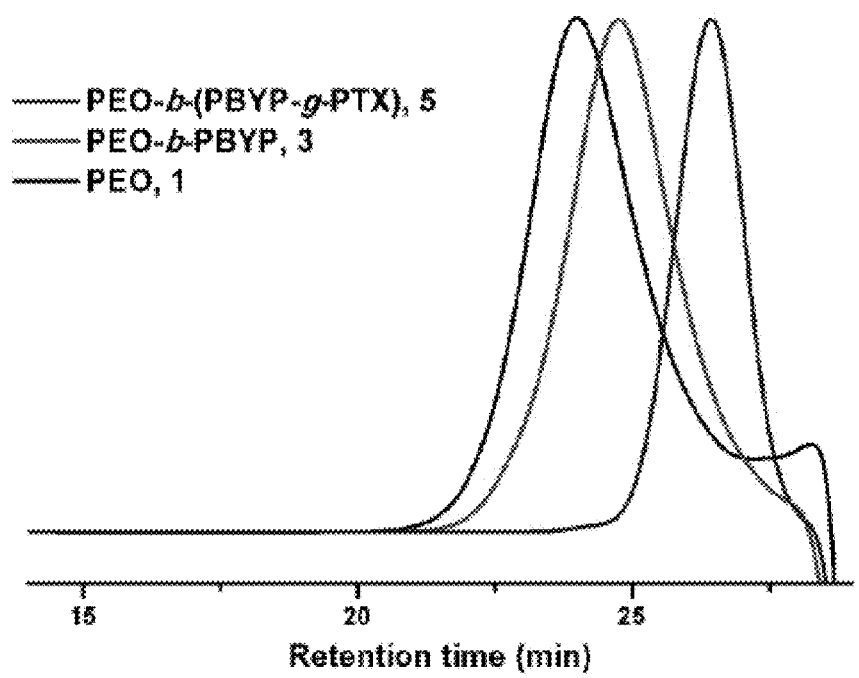
FIG. 6B depicts GPC traces of PEO, PEO-b-PBYP and PEO-b-(PTX-g-PBYP).

Discussion:

The PEO-b-PPE-g-PTX conjugates were synthesized as illustrated in FIG. 6.

PEO (average $M_n$~2,000 Da) 1 was used to initiate the ROP of butyryl phospholane (BYP) 2, which yielded the well-defined diblock copolymer, $PEO_{44}$-b-$PBYP_{30}$ 3. This controlled organocatalyzed ring-opening polymerization (ROP) of the cyclic phospholane monomer gave quantitative conversion in only 4 min, and was highly reproducible. With a 1:30 stoichiometry of PEO:BYP, 3 was produced having $M_n$=7200 Da in agreement with the theoretical degrees of polymerization, as determined by $^1$H NMR spectroscopy, and narrow molecular weight distribution, $M_w/M_n$=1.17, as determined by gel permeation chromatography (GPC). To equip PTX with a functionality for coupling to PEO-b-PPE, the C-2'-OH position of PTX in this Example was functionalized with an azido group through an ester linkage, by reaction with 6-azidohexanoic acid and employing a slight excess of PTX (1.2 eq), in the presence of N,N'-dicyclohexylcarbodiimide and 4-(dimethylamino)pyridine in $CH_2Cl_2$ heated at reflux for 3 d to afford PTX C2'-ester 4 as the predominant product. Automated high performance flash chromatography with prepacked fine spherical silica gel (20-40 µm) was used to isolate 4 in 78% yield. "Click" type azide-alkyne Huisgen cycloaddition (CuAAC) was employed to attach 4 onto the backbone of 3.

PEO-b-PPE-g-PTX conjugates were synthesized with a range of feed ratios of azido-PTX to PEO-b-PPE alkyne (20%, 50% and 100%). As shown in FIG. 29, even though the conjugation efficiency decreased as the feed ratio increased, the click-type reaction showed higher conjugation efficiency than that observed for esterification-based conjugation of sterically-bulky PTX onto polymers. See Zou, J.; Yu, Y.; Li, Y. K.; Chen, C. K.; Cheng, C. *J Polym. Sci. Pol. Chem.* 2012, 50, 142; Ernsting, M. J.; Tang, W. L.; MacCallum, N.; Li, S. D. *Bioconjugate Chem.* 2011, 22, 2474; Nakamura, J.; Nakajima, N.; Matsumura, K.; Hyon, S. H. *Anticancer Res* 2010, 30, 903. The highest PTX loading capacity, 65 wt %, was reached when the feed ratio was 100%, however, this polymer had a poor solubility in water (lower than 0.5 mg/mL). The optimal polymer in this Example had conjugation efficiency as high as 90%, PTX loading capacity of 55 wt %, and high water solubility (11.3 mg/mL) when the feeding ratio of 4 to 3 was removed by repeated precipitation from acetone into diethyl ether 3 times. Complete removal of the unreacted 4 was confirmed by $^1$H NMR and GPC analysis of the product.

Figure 7A:
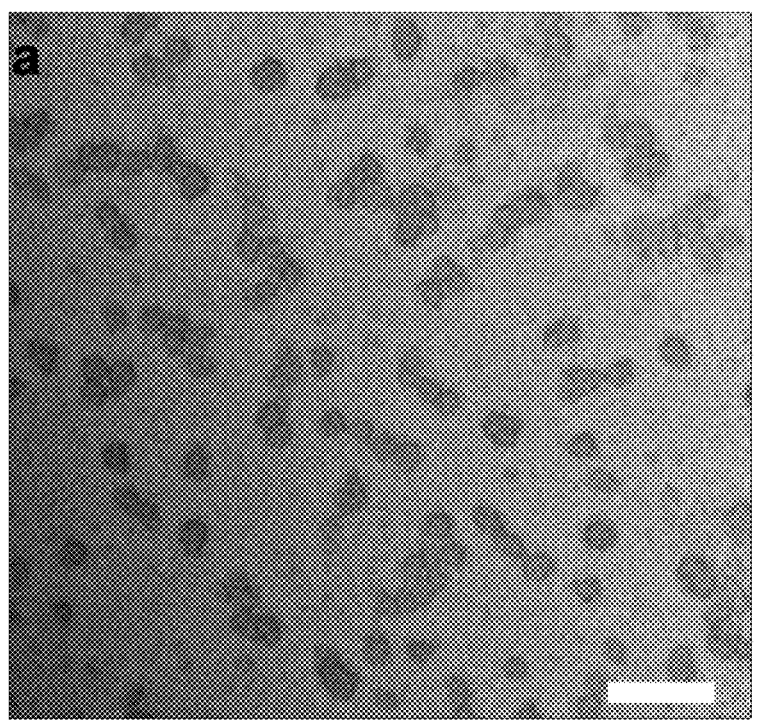
FIG. 7A depicts a TEM image of PEO-b-PPE-g-PTX nanoparticles, average diameter is 24±6 nm (scale bar: 100 nm).
Figure 7B:
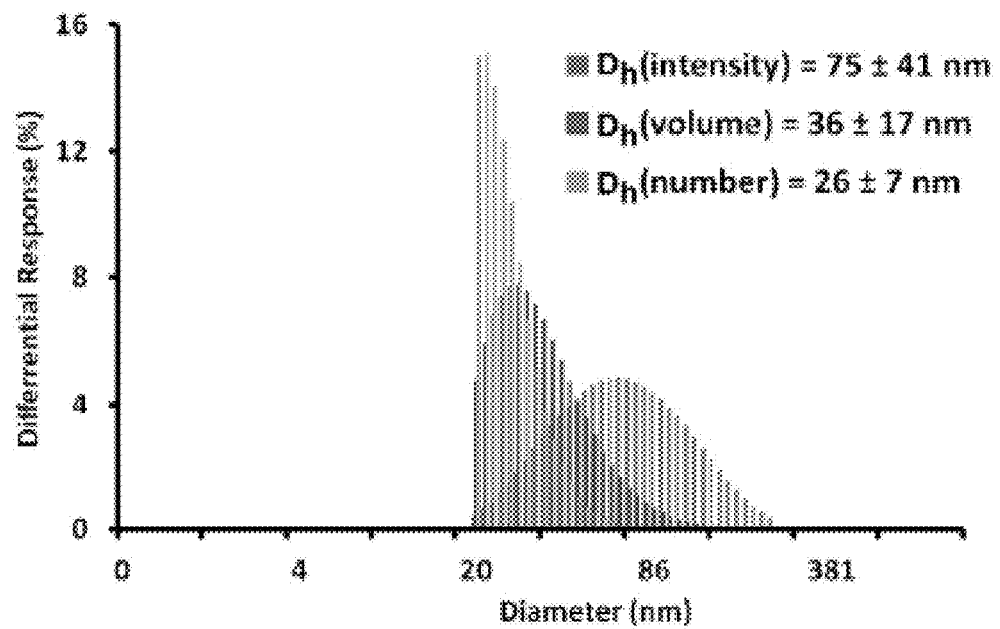
FIG. 7B depicts DLS results of PEO-b-PPE-g-PTX nanoparticles in water.
Figure 8A:
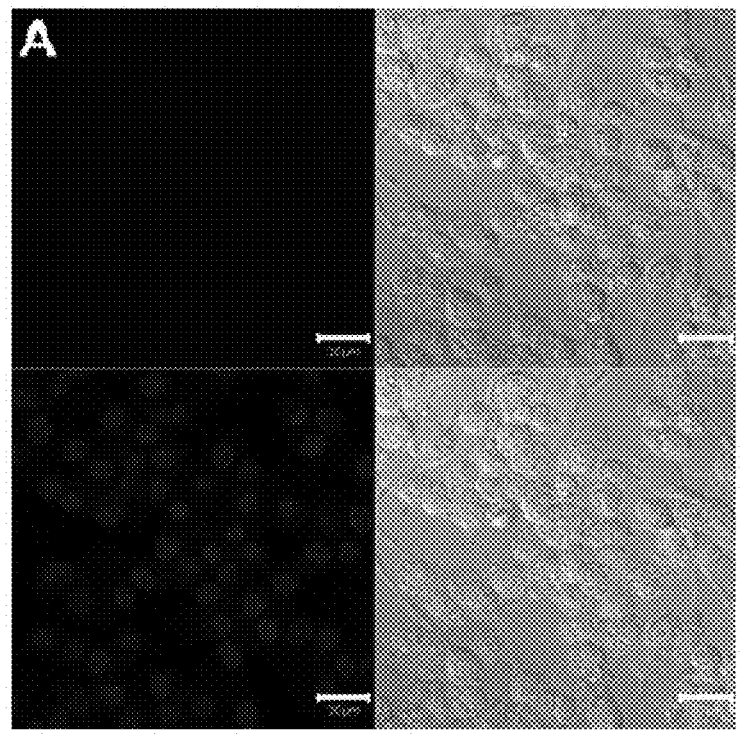
Figure 8B:
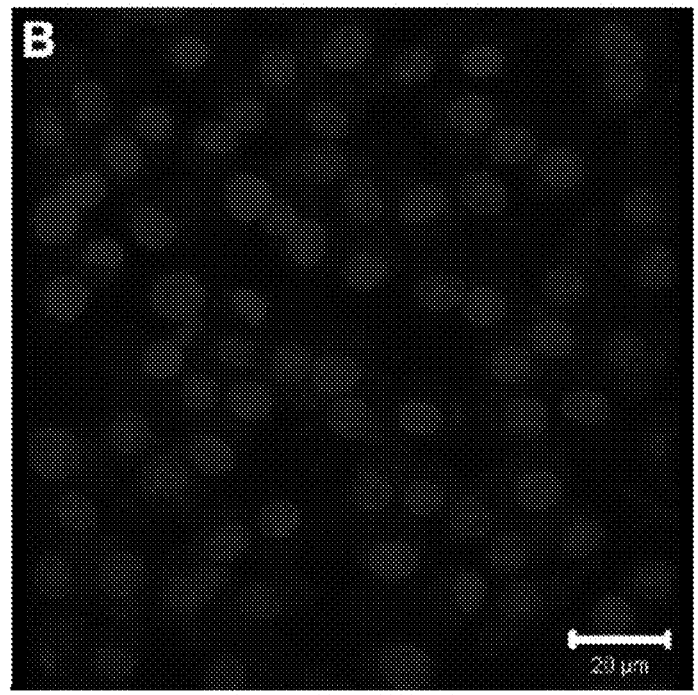
Figure 8C:
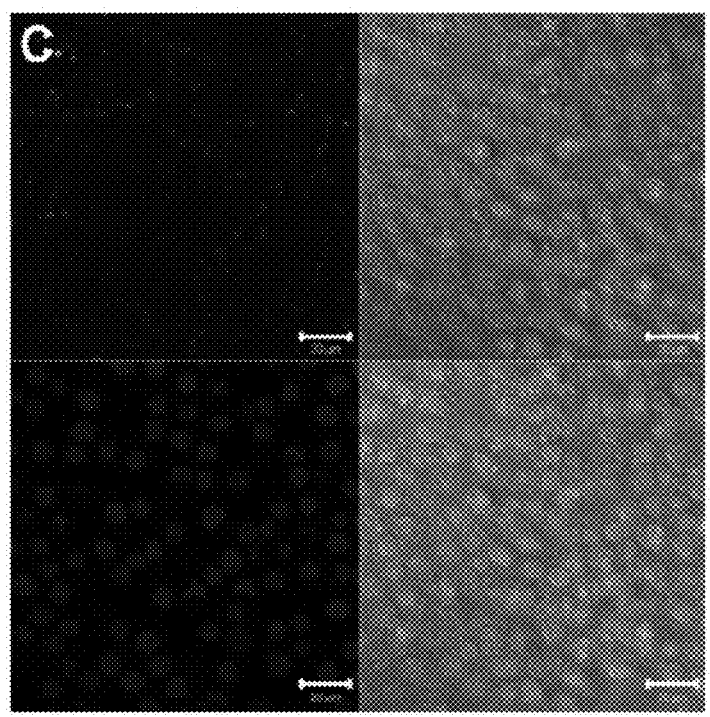
Figure 8D:
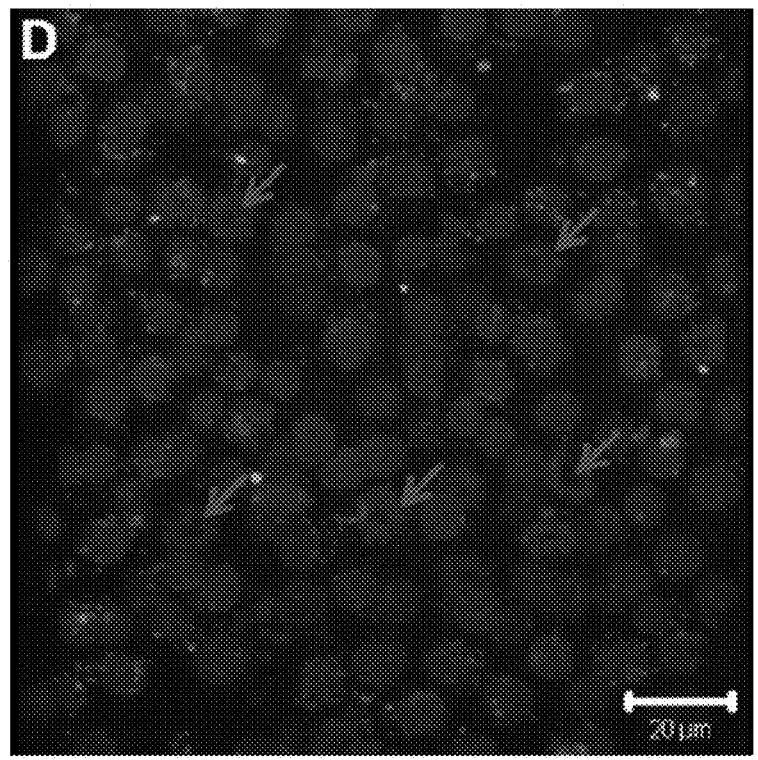

The PEO-b-PPE-g-PTX drug conjugates, 5, were further purified and supramolecularly assembled in water by being dissolved in acetone and dialzed against nanopure water containing Chelex 100 resin (100-200 mesh) for 2 days, to remove copper ion and also to trigger self-assembly. The resulting micelle solution was obtained and then passed through a 450 nm polypropylene filter to remove dust and large aggregates. The micelle solution was lyophilized to give a faint yellow powder with an overall yield above 90%. The lyophilized PEO-b-PPE-g-PTX conjugates could be easily dissolved into water at a concentration as high as 11.3 mg/mL (equivalent PTX concentration of 6.2 mg/mL) by applying sonication for 3 min. Dynamic light scattering (DLS) analysis indicated the number-average hydrodynamic diameter of the micelles was 26±7 nm, and transmission electron microscopy (TEM) images confirmed that the PEO-b-PPE-g-PTX nanoassemblies were well-dispersed in water in the form of micellar nanoparticles with a narrow size distribution $D_{av}$=24±6 nm (see FIG. 7).

Click-type reaction has been demonstrated to be highly efficient when coupling large-sized anticancer drugs. See, e.g., Johnson, J. A.; Lu, Y. Y.; Burts, A. O.; Lim, Y. H.; Finn, M. G.; Koberstein, J. T.; Turro, N. J.; Tirrell, D. A.; Grubbs, R. H. *J Am Chem Soc* 2011, 133, 559; Yu, Y.; Zou, J.; Yu, L.; Jo, W.; Li, Y. K.; Law, W. C.; Cheng, C. *Macromolecules* 2011, 44, 4793; Iha, R. K.; Wooley, K. L.; Nystrom, A. M.; Burke, D. J.; Kade, M. J.; Hawker, C. J. *Chem Rev* 2009, 109, 5620. In this Example, click chemistry provided a highly-efficient strategy to load PTX onto reactive polymer backbones in extremely high coupling conversion and PTX loading capacity. PEO-b-PPE-g-PTX drug conjugates 5 were dissolved in water at the equivalent PTX concentration of 6.2 mg/mL, exhibiting significantly enhanced solubility, more than 24,800-fold, as compared to the free drug, and 2.4-fold higher than that reported for PTX conjugates with PGA. See Van, S.; Das, S. K.; Wang, X. H.; Feng, Z. L.; Jin, Y.; Hou, Z.; Chen, F.; Pham, A.; Jiang, N.; Howell, S. B.; Yu, L. *Int J Nanomed* 2010, 5, 825.

The lyophilized, powder-like PEO-b-PPE-g-PTX conjugates of this Example show no evidence of degradation or properties over 3 months when stored under nitrogen at −20° C. The GPC profile and DLS analysis confirmed that the chemical compositions of the polymer-drug conjugates and the particle sizes of the micelles did not change after 3 months of storage. Hence, the powder form of the conjugates may be easily stored, transported and re-suspended prior to use.

One aspect of the PEO-b-PPE-g-PTX nanoparticle system is an ability to undergo hydrolytic degradation to release the PTX and allow it to perform its chemotherapeutic activity, while also eliminating the polymer nanoparticle structure. Aqueous solution-state hydrolysis studies were conducted by observing breakdown of the polyphosphoester backbone by $^{31}$P NMR spectroscopy as a function of time and pH, with the PEO-b-PPE block copolymer dissolved in $D_2O$ at different pH values. At neutral pH, the polyphosphoester was fully stable over the entire period of measurement, over 150 hours. The rate and extent of hydrolysis increased with increasing pH. As the pH was reduced to acidic values, complications occurred with aggregation and precipitation events preventing accurate determination of the extent of hydrolysis. However, there was a general trend of increased hydrolysis, relative to neutral pH. That accelerated hydrolytic degradation occurred for the polyphosphoester backbone of this Example at acidic pH has application for selective release in tumor cell environments, and also may be useful for enzymatic catalysis. The PEO-b-PPE-g-PTX system of this Example may be used as a platform for combinational therapy and bioimaging.

The PEO-b-PPE-g-PTX nanoparticle system of this Example was studied for its cytotoxic effect against several cancer cell lines. Both the Cremophor-EL/ethanol (1:1 v/v) and PEO-b-PPE polymers (the backbone of the nanoparticles) were not cytotoxic to the cells at the concentrations that were tested for the delivery of PTX. PTX conjugated onto the nanoparticles as in this Example showed 8-to-63-fold lower cytotoxicity than the commercial-mimicking formulation of PTX, depending on the sensitivity of the tested cell line to the drug Results comparing the $IC_{50}$ values of PTX (as a Taxol®-mimicking formulation; Cremophor-EL and ethanol, 1:1 v/v with OVCAR-3 and RAW 264.7 cells and free PTX with KB and A549 cell lines) and PTX conjugate incubated for 72 h in OVCAR-3, RAW 264.7, KB and A549 cell lines are provided in Table 1.

TABLE 1

| Formulation | $IC_{50}$ (µM) | | | |
| --- | --- | --- | --- | --- |
| | OVCAR-3 | RAW 264.7 | KB cells | A549 cells |
| PTX | 0.007 | 0.044 | 0.0044 | 0.2866 |
| PPE-PTX | 0.119 | 2.829 | 0.039 | 1.4706 |

The reduced cytotoxicity of the PTX of this Example over commercial PTX is explained by the time required for dissociation of the conjugated drug from the PEO-b-PPE backbone, followed by the physical release from the nanoparticles, in contrast to the drug that is physically loaded into the low molecular weight surfactant, Cremophor-EL. Lower cytotoxicities of PTX-polymeric drug conjugates, due to the slow in vitro release kinetics, have been previously reported in literature. For instance, PGA-PTX conjugates exhibits 6-to-180-fold lower cytotoxicity than PTX, depending on the cell line utilized. See Yang, D.; Van, S.; Liu, J.; Wang, J.; Jiang, X. G.; Wang, Y. T.; Yu, L. *Int J Nanomed* 2011, 6, 2557. A contributing explanation could be the low cellular entry of the nanoparticles versus the possibility of the instantaneous release of PTX from the Cremophor-EL low molecular weight surfactant in the cell culture media, which can then passively diffuse into the cells and induce cytotoxicity. Nonetheless, this lower cytotoxicity can be advantageous by providing, for example, increased safety for in vivo applications. For example, the PEO-b-PPE-g-PTX nanoparticle micelle system of this Example could provide stability during blood circulation and allow release primarily after high accumulation in tumor tissues via the enhanced permeability and retention effect.

To investigate the cell internalization of the PEO-b-PPE-g-PTX conjugates of this Example, a portion of the residual alkynyl groups were labelled with azido-functionalized fluorescein by click-type reaction. The cellular uptake of the fluorescein-labeled PEO-b-PPE-g-PTX nanoparticles into OVCAR-3 cells and RAW 264.7 mouse macrophages was tested at different concentrations. After 5-hour incubation and at PTX concentration of 15 µM, the nanoparticles could be visualized (green) in the cytoplasm of the RAW 264.7 cells surrounding the nucleus (blue) in FIG. 8. In addition, morphological changes in the nucleus are demonstrated, which might be due to the apoptosis induced by the released PTX (shown by red arrows on FIG. 3). See also Ang, E. S. M.; Pavlos, N. J.; Chim, S. M.; Feng, H. T.; Scaife, R. M.; Steer, J. H.; Zheng, M. H.; Xu, J. *Journal of Cellular Biochemistry* 2012, 113, 946.

Lower concentrations on the same cell line (3 µM) or on OVCAR-3 (lower concentration of 0.5 µM is used due to the high sensitivity of this cell line to PTX, per Table 1 above) could not observe the cellular uptake of the nanoparticles. See FIG. 8. Control-untreated cells or cells treated with PEO-b-PPE lacking PTX did not show any morphological changes in the nuclei.

In one example, we have developed a novel PEO-b-PPE-g-PTX drug conjugate system. Click chemistry was employed to attach bulky PTX molecules covalently and densely onto the amphiphilic block copolymer backbone, and to label the resulting PEO-b-PPE-g-PTX system with fluorescein. In addition, residual alkynes provide possibilities of further post-chemical modifications (e.g., crosslinking, radio-labeling, decoration with targeting ligands) as opposed to the lack of functionalizability of Taxol or Abraxane. Also in contrast to other promising PTX-based nanoparticle systems, the partitioning of separate PEO and PTX-functionalized PPE constituents within different regions along the block copolymer structure of this Example allows for placement of the components and their functions within different regions of the resulting nanoparticulate block copolymer micelle framework. Therefore, the PEO-b-PPE-g-PTX achieved a PTX loading capacity as high as 65 wt % and a water solubility at equivalent PTX concentration of 6.2 mg/mL. Visualization of fluorescein-labeled PEO-b-PPE-g-PTX in cells by confocal fluorescence microscopy demonstrated the successful cellular internalization.

Example 2

Another type of PEO-b-PPE-g-PTX drug conjugate system with acid-labile linkage was developed and named as PPE-PTX-G2. When acid-labile linkages were introduced between drug moieties and polymer backbone, the PTX release rate from PPE polymer backbone showed pH sensitive properties. At acidic condition, PTX release faster than at neutral pH. See FIG. 9.

See FIG. 10 for the synthesis of PPE-PTX-G2. X is 0.63 and PTX loading is 53 wt %.

$^1$H NMR and GPC were used to confirm formation of PPE-PTX-G2 as shown in FIG. 10.

The morphology and size distribution of PPE-PTX-G2 was examined using TEM and DLS as shown in FIG. 11. The solubility of PPE-PTX-G2 as greater than 1.3 mg/mL. PTX concentration was greater than 0.68 mg/mL.

The saturate concentration of PTX in PBS buffer is shown in FIG. 12. The saturate concentration is around 1.7 ug/mL. PTX concentrations as low as 6.25 ng/mL were detected.

The release of PTX from PPE-PTX-G2 also was investigated using HPLC. The results are shown in FIG. 13.

A comparison of $IC_{50}$ values of PTX (as a Taxol-mimicking formulation; Cremophor-EL and ethanol, 1:1 v/v) for PPE-PTX and PPE-PTX G2 in OVCAR-3 and RAW 264.7 cells incubated for 72 hours is provided in Table 2.

TABLE 2

| Formulation | $IC_{50}$ (µM) in OVCAR-3 | $IC_{50}$ (µM) in RAW 264.7 |
| --- | --- | --- |
| PTX | 0.007 | 0.04 |
| PPE-PTX | 0.119 | 2.83 |
| PPE-PTX-G2 | 0.022 | 0.38 |

Synthesis of PPE-PTX-G3. A redox-sensitive disulfide bond is appended to the PTX according to the reaction shown in FIG. 14.

A PEBP-b-(PBYP-g-PEG) block graft terpolymer may be prepared according to the reaction sequence shown in FIG. 15.

GPC analysis is shown in FIG. 16. GPC results are also provided in Table 3.

TABLE 3

| Polymer | $M_n$ (Da) | $M_w$ (Da) | PDI |
| --- | --- | --- | --- |
| PEBP$_{50}$ | 10400 | 11850 | 1.14 |
| PEBP$_{50}$-b-PBYP$_{50}$ | 16200 | 21000 | 1.27 |
| PEBP$_{50}$-(b-PBYP$_{50}$-g-PEG) | 21800 | 27000 | 1.24 |

Characterization of micellar nanoparticles of PEBP-b-(PBYP-g-PEG) block graft terpolymer loaded with PTX is shown in FIG. 17.

Shell-cross-linked nanoparticles of PEBP-b-(PBYP-g-PEG) block graft terpolymer loaded with PTX. SCKs were formed by adding a crosslinking agent followed by loading the SCKs with PTX according to the diagram of FIG. 18.

The resultant SCKs were analyzed using DLS and TEM, shown in FIG. 19.

Example 3

Experimental Section:

Materials.

N,N-dimethylformamide (DMF), ethyl acetate, acetone, diethyl ether, methanol, acetone, diethyl ether, 1,8-diazabicyclo[5.4.0]undec-7-ene (DBU), 1,5,7-triazabicyclo[4.4.0]dec-5-ene (TBD), acetic acid, 3-butyn-1-ol, cysteamine hydrochloride, 2-ethyl-1-butanol, 2-(2-methoxyethoxy)ethanethiol, 3-mercaptopropanoic acid, L-cysteine hydrochloride monohydrate, benzyl alcohol, acetic acid, triethylamine (TEA), and 2,2-dimethoxy-2-phenylacetophenone (DMPA) were used as received from Sigma-Aldrich Company (St. Louis, Mo.). 2-chloro-2-oxo-1,3,2-dioxaphospholane (COP, 95%) was used as received from Thermo Fisher Scientific Inc (Pittsburgh, Pa.). Tetrahydrofuran (THF) and dichloromethane (DCM) were dried through columns (J. C. Meyer Solvent Systems, Inc., Laguna Beach, Calif.). Nanopure water (18 MΩ·cm) was acquired by means of a Milli-Q water filtration system, Millipore Corp. (St. Charles, Mo.).

Characterization Techniques.

$^1$H NMR, $^{31}$P NMR and $^{13}$C NMR spectra were recorded on an Inova 300 MHz or Mercury 300 MHz spectrometer interfaced to a UNIX computer using VnmrJ software. Chemical shifts were referenced to the solvent resonance signals. The DMF gel permeation chromatography (GPC) was conducted on a Waters Chromatography, Inc. (Milford, Mass.) system equipped with an isocratic pump model 1515, a differential refractometer model 2414, and a four-column set of 5 μm Guard (50×7.5 mm), Styragel HR 4 5 μm DMF (300×7.5 mm), Styragel HR 4E 5 μm DMF (300×7.5 mm), and Styragel HR 2 5 μm DMF (300×7.5 mm). The system was equilibrated at 70° C. in pre-filtered DMF containing 0.05 M LiBr, which served as polymer solvent and eluent (flow rate set to 1.00 mL/min). Polymer solutions were prepared at a concentration of ca. 3 mg/mL and an injection volume of 200 μL was used. Data collection and analysis were performed with Empower 2 v. 6.10.01.00 software (Waters, Inc.). The system was calibrated with polystyrene standards (Polymer Laboratories, Amherst, Mass.) ranging from 615 to 442,800 Da. IR spectra were recorded on an IR Prestige 21 system (Shimadzu Corp.) and analyzed using IRsolution v. 1.40 software. Glass transition temperatures ($T_g$) were measured by differential scanning calorimetry on a Mettler-Toledo DSC822® (Mettler-Toledo, Inc., Columbus, Ohio), with a heating rate of 10° C./min. Measurements were analyzed using Mettler-Toledo STARe v. 7.01 software. The $T_g$ was taken as the midpoint of the inflection tangent, upon the third heating scan. Thermogravimetric analysis was performed under $N_2$ atmosphere using a Mettler-Toledo model TGA/SDTA851$^e$, with a heating rate of 5° C./min. Measurements were analyzed by using Mettler-Toledo STARe v. 7.01 software. Transmission electron microscopy (TEM) was conducted on a Hitachi H-7500 microscope, operating at 100 kV. Samples for TEM measurements were prepared as follows: 4 μL of the dilute solution (with a polymer concentration of 0.1 mg/mL) was deposited onto a carbon-coated copper grid, and after 2 min, the excess of the solution was quickly wicked away with a piece of filter paper. The samples were then negatively stained with 1 wt % phosphotungstic acid (PTA) aqueous solution. After 1 min, the excess staining solution was quickly wicked away with a piece of filter paper and the samples were left to dry under ambient conditions overnight. The average diameter of nanoparticles on the TEM grid was obtained by measuring the core domain of 200 sphere particles at different areas of the TEM specimen and the standard deviation was presented as error. Dynamic light scattering (DLS) measurements were conducted using a Delsa Nano C from Beckman Coulter, Inc. (Fullerton, Calif.) equipped with a laser diode operating at 658 nm. Scattered light was detected at 165° angle and analyzed using a log correlator over 70 accumulations for a 0.5 mL of sample in a glass size cell (0.9 mL capacity). The photomultiplier aperture and the attenuator were automatically adjusted to obtain a photon counting rate of ca. 10 kcps. The calculation of the particle size distribution and distribution averages was performed using CONTIN particle size distribution analysis routines using Delsa Nano 2.31 software. The peak averages of histograms from intensity, volume and number distributions out of 70 accumulations were reported as the average diameter of the particles. All determinations were repeated 10 times. The zeta potential values of the nanoparticles were determined by Delsa Nano C particle analyzer (Beckman Coulter. Fullerton, Calif.) equipped with a 30 mW dual laser diode (658 nm). The zeta potential of the particles in suspension was obtained by measuring the electrophoretic movement of charged particles under an applied electric field. Scattered light was detected at a 30° angle at 25° C. The zeta potential was measured at five regions in the flow cell and a weighted mean was calculated. These five measurements were used to correct for electroosmotic flow that was induced in the cell due to the surface charge of the cell wall. All determinations were repeated 6 times.

Synthesis of hydrophobic monomer, 2-ethylbutyl phospholane (EBP).

To a stirred solution of 2-ethyl-1-butanol (7.87 g, 78 mmol) and triethylamine (7.80 g, 78 mmol) in 250 mL of anhydrous THF at 0° C. was added a solution of COP (10.0 g, 70 mmol) in 50 mL of anhydrous THF dropwise, and the reaction mixture was allowed to stir for 12 h in an ice bath. After complete conversion of COP, as confirmed by TLC, the reaction mixture was filtered and the filtrate was concentrated. The concentrated filtrate was distilled under reduced pressure to obtain a colorless viscous liquid (118-121° C., 0.4 mmHg, 10.6 g, Yield: 73%). $^1$H NMR (CDCl$_3$, ppm): δ 0.86 (t, J=7.5 Hz, 6H, POCH$_2$CH(CH$_2$CH$_3$)$_2$), 1.34 (m, 4H, POCH$_2$CH(CH$_2$CH$_3$)$_2$), 1.46 (m, 1H, POCH$_2$CH), 4.03 (m, 2H, POCH$_2$CH), 4.36 (m, 4H, POCH$_2$CH$_2$OP). $^{13}$C NMR (CDCl$_3$, ppm): δ 10.85, 22.64, 41.55, 66.01, 70.75. $^{31}$P NMR (CDCl$_3$, ppm): δ 17.70. HRMS: calculated [M+H]$^+$ for C$_8$H$_{18}$O$_4$P: 209.0943. found: 209.1013. IR (cm$^{-1}$): 3010-2850, 1462, 1286, 1016, 927, 836, 772 cm$^{-1}$.

General Procedure for Polymerization of EBP.

A solution of EBP (0.50 g, 2.4 mmol) and a given amount of benzyl alcohol (0.023 mmol to 0.093 mmol) in anhydrous dichloromethane (0.40 mL) was transferred into a flame-dried 5-mL shell vial equipped with a rubber septum and a stir bar. In the cases of using DBU as the catalyst, at 25° C., a solution of a given amount of DBU (0.035 mmol to 0.140 mmol) in anhydrous dichloromethane (0.1 mL) was injected into the vial via syringe, while being maintained under a nitrogen gas atmosphere. In the cases of using TBD as the catalyst, at 0° C., a solution of a given amount of TBD (0.035 mmol to 0.140 mmol) in anhydrous dichloromethane (0.1 mL) was injected into the vial via syringe, while being maintained under a nitrogen gas atmosphere. After being stirred for a certain period of time, the reaction vial was unstoppered and a solution of acetic acid (excess) in dichloromethane was added via pipet into the reaction mixture to quench the reaction. The poly(EBP) (PEBP) was purified by precipitation from dichloromethane into pentane (3×), and was then dried under vacuum. A series of polymers was prepared, with the characterization data for a particular sample reported here: $^1$H NMR (CDCl$_3$, ppm): δ 0.93 (t, J=7.4 Hz, POCH$_2$CH(CH$_2$CH$_3$)$_2$), 1.40 (m, POCH$_2$CH (CH$_2$CH$_3$)$_2$), 1.55 (m, 1H, POCH$_2$CH), 4.07 (m, POCH$_2$CH), 4.23-4.31 (br m, POCH$_2$CH$_2$OP). $^{13}$C NMR (CDCl$_3$, ppm): δ 10.90, 22.67, 41.49, 66.04-66.21, 70.07. $^{31}$P NMR (CDCl$_3$, ppm): δ −1.19. DSC: T$_g$=−55.4° C. TGA in N$_2$: 180-260° C., 60% mass loss, 260-600° C., 17% mass loss, 23% mass remaining above 600° C. IR (cm$^{-1}$): 3010-2850, 1644, 1459, 1381, 1273, 1016, 964, 869, 808 cm$^{-1}$.

Synthesis of PEBP$_{50}$-b-PBYP$_{50}$ Diblock Copolymer.

A solution of EBP (1.500 g, 7.2 mmol) and benzyl alcohol (15.6 mg, 0.14 mmol) in anhydrous dichloromethane (2.0 mL) was transferred into a flame-dried 25-mL round flask equipped with a rubber septum and a stir bar in an ice bath. At 0° C., a solution of TBD (40.2 mg, 0.28 mmol) in anhydrous dichloromethane (0.4 mL) was injected quickly into the flask via syringe, while being maintained under a nitrogen gas atmosphere. After being stirred for 2 min, another 2.4 mL of anhydrous dichloromethane was injected into the flask to dilute the reaction mixture and sodium chloride was mixed with the surrounding ice bath (at a wt ratio of 1:3) to provide a cooling system for −20° C. Less than 0.1 mL of the reaction mixture was withdrawn to determine the conversion of EBP by $^{31}$P NMR and the molecular weight and polydispersity by DMF GPC. After the reaction mixture had been stirred at −20° C. and the lower concentration for 3 min, a solution of BYP (1.27 g, 7.2 mmol) in anhydrous dichloromethane (2.4 mL) was injected quickly into the flask via syringe. After being stirred for 1 min at −20° C., the reaction vial was unstoppered and a solution of acetic acid (excess) in dichloromethane was added via pipet into the reaction mixture to quench the reaction. After the reaction was quenched, the conversion of BYP was determined by $^{31}$P NMR. The conversions of EBP and BYP were each above 99%. The PEBP-b-PBYP, 3 was purified by precipitation from 20 mL of dichloromethane into 240 mL pentane and diethyl ether mixture (3:1 vol ratio) three times, and was then dried under vacuum, to give the product polymer as a colorless viscous liquid in a yield of 84%. $^1$H NMR (CDCl$_3$, ppm): δ 0.93 (t, J=7.4 Hz, POCH$_2$CH(CH$_2$CH$_3$)$_2$), 1.40 (m, POCH$_2$CH(CH$_2$CH$_3$)$_2$), 1.55 (m, 1H, POCH$_2$CH), 2.18-2.04 (br s, POCH$_2$CH$_2$C≡CH), 2.65-2.57 (br m, POCH$_2$CH$_2$C≡CH), 4.19-3.99 (br m, POCH$_2$CH, POCH$_2$CH$_2$), 4.31-4.21 (br, POCH$_2$CH$_2$OP), 5.13 (d, J=6.0 Hz, OCH$_2$Ar), 7.40 (m, Ar—H). $^{13}$C NMR (CDCl$_3$, ppm): δ 10.79, 20.48, 22.56, 41.37, 66.46-65.66, 69.92, 70.76, 79.47, 127.84, 128.51. $^{31}$P NMR (CDCl$_3$, ppm): δ −1.19, −1.83. GPC: M$_n$=16700 g/mol, PDI=1.17. DSC: T$_g$=−37.2° C. TGA in N$_2$: 185-260° C., 52% mass loss; 260-300° C., 10% mass loss, 300-600° C., 11% mass loss, 27% mass remaining above 600° C. IR (cm$^{-1}$): 3700-3100, 3020-2840, 1644, 1459, 1383, 1270, 1012, 972, 869, 805 cm$^{-1}$.

General Procedure of Thiol-yne Reactions of PEBP$_{50}$-b-PBYP$_{50}$ with Functional Thiols.

A solution of PEBP$_{50}$-b-PBYP$_{50}$ (0.30 g, M$_n$=19000, 0.79 mmol alkynes), functional thiol (7.8 mmol), and DMPA (31.0 mg, 0.12 mmol) in 10.0 mL of methanol was bubbled with nitrogen for 5 min and then irradiated under UV irradiation (365 nm) for 2 h. For non-ionic thiol (2-(2-methoxyethoxy)ethanethiol) functionalized and anionic thiol (3-mercaptopropionoic acid) functionalized diblock copolymers, the reaction mixtures were precipitated from methanol or acetone into pentane and diethyl ether mixture (3:1 ratio) three times to remove excess functional thiols and photoinitiator by-products to give the product polymers. For cationic thiol (cysteamine hydrochloride) functionalized and zwitterionic thiol (L-cysteine hydrochloride monohydrate) functionalized diblock copolymers, the methanol solutions were transferred to dialysis tubing (MWCO: 6-8 kDa) and dialyzed against nanopure water with hydrochloride (pH=3.0) in the cold room (4-8° C.) for 36 h, to remove excess functional thiols and DMPA and photoinitiator by-products. The micelle solution was lyophilized to give the product polymers.

The non-ionic diblock product was obtained in the form of a colorless viscous liquid in a yield of 50%. $^1$H NMR (CD$_3$OD, ppm): δ 0.97 (t, J=7.4 Hz, POCH$_2$CH(CH$_2$CH$_3$)$_2$), 1.43 (m, POCH$_2$CH(CH$_2$CH$_3$)$_2$), 1.58 (m, 1H, POCH$_2$CH), 1.76-1.92, 2.31-2.47 (br, POCH$_2$CH$_2$), 2.77-3.14 (br, CH$_2$SCH$_2$CHSCH$_2$), 3.40 (br, CH$_2$OCH$_2$CH$_2$OCH$_3$), 3.54-3.75 (br, CH$_2$OCH$_2$CH$_2$OCH$_3$), 3.96-4.47 (br, POCH$_2$CH, POCH$_2$CH$_2$, POCH$_2$CH$_2$OP), 5.13 (d, J=6.0 Hz, OCH$_2$Ar), 7.40 (m, Ar—H). $^{13}$C NMR (CD$_3$OD, ppm): δ 10.80, 22.58, 30.23, 32.24, 34.00, 41.39, 42.43, 59.10, 66.48-65.68, 70.07, 71.89, 127.86, 128.54. $^{31}$P NMR (CD$_3$OD, ppm): δ −1.19, −1.27. DSC: T$_g$=−49.6° C. TGA in N$_2$: 185-260° C., 57% mass loss; 260-600° C., 14% mass loss, 29% mass remaining above 600° C. IR: 3020-2800, 1646, 1457, 1356, 1273, 1091, 1020, 972, 808 cm$^{-1}$.

The anionic diblock product was obtained in the form of a colorless solid in a yield of 96%. $^1$H NMR (CD$_3$OD, ppm): δ 0.97 (t, J=7.4 Hz, POCH$_2$CH(CH$_2$CH$_3$)$_2$), 1.45 (m, POCH$_2$CH(CH$_2$CH$_3$)$_2$), 1.58 (m, 1H, POCH$_2$CH), 1.76-1.93, 2.31-2.46 (b, POCH$_2$CH$_2$), 2.63-2.73 (b, CH$_2$COOH), 2.75-3.09 (br, CH$_2$SCH$_2$CHSCH$_2$), 3.89-4.42 (br, POCH$_2$CH, POCH$_2$CH$_2$, POCH$_2$CH$_2$OP), 5.13 (d, J=6.0 Hz, OCH$_2$Ar), 7.40 (m, Ar—H). $^{13}$C NMR (CD$_3$OD, ppm): δ 10.90, 22.67, 30.23, 32.24, 34.01, 38.96, 41.49, 42.44, 59.06, 66.04-66.23, 70.15, 71.13, 71.89, 164.99. $^{31}$P NMR (CD$_3$OD, ppm): δ −1.19, −1.43. DSC: T$_g$=−57.1° C. TGA in N$_2$: 100-200° C., 14% mass loss; 200-260° C., 39% mass loss, 260-600° C., 15% mass loss, 32% mass remaining above 600° C. IR: 3200-2800, 2800-2190, 1997-1823, 1791, 1459, 1409, 1020, 920, 805 cm$^{-1}$.

The cationic diblock polymer was obtained as a faint yellow product with a yield of 63%. Due to the hygroscopic nature, the product polymer was kept under vacuum in the desiccators. $^1$H NMR (d$_6$-DMSO, ppm): δ 0.86 (t, J=7.4 Hz, POCH$_2$CH(CH$_2$CH$_3$)$_2$), 1.32 (m, POCH$_2$CH(CH$_2$CH$_3$)$_2$), 1.48 (m, 1H, POCH$_2$CH), 1.65-1.84, 2.17-2.36 (b, POCH$_2$CH$_2$), 2.76-3.14 (br, CH$_2$SCH$_2$CHSCH$_2$, CH$_2$NH$_3$), 3.90-4.39 (br, POCH$_2$CH, POCH$_2$CH$_2$, POCH$_2$CH$_2$OP), 5.05 (d, OCH$_2$Ar), 7.40 (m, Ar—H). $^{13}$C NMR (d$_6$-DMSO, ppm): δ 11.07, 22.61, 27.72, 29.00, 33.76, 37.45, 41.29, 41.75, 43.89, 66.31-67.01, 69.25, 69.33, 128.19, 128.88. $^{31}$P NMR (d$_6$-DMSO, ppm): δ –1.19, –1.47. DSC: T$_g$=–51.4° C. TGA in N$_2$: 170-330° C., 55% mass loss; 330-600° C., 17% mass loss, 28% mass remaining above 600° C. IR: 3600-3300, 3300-2400, 1608, 1462, 1255, 1017, 964, 801 cm$^{-1}$.

The zwitterionic diblock polymer was obtained as a faint yellow powder with a yield of 68%. Due to the hygroscopic nature, the product polymer was kept under vacuum in a desiccator. $^1$H NMR (d$_6$-DMSO, ppm): δ 0.83 (m, POCH$_2$CH(CH$_2$CH$_3$)$_2$), 1.30 (m, POCH$_2$CH(CH$_2$CH$_3$)$_2$), 1.43 (m, 1H, POCH$_2$CH), 1.72-1.87, 2.07-2.23 (b, POCH$_2$CH$_2$), 2.80-3.18 (br, CH$_2$SCH$_2$CHSCH$_2$, CH$_2$CH (NH$_3$)COOH), 3.92-4.35 (br, POCH$_2$CH, POCH$_2$CH$_2$, POCH$_2$CH$_2$OP), 5.02 (d, J=8.2 Hz, OCH$_2$Ar), 7.40 (m, Ar—H). $^{13}$C NMR (d$_6$-DMSO, ppm): δ 11.06, 22.62, 27.72, 29.02, 33.76, 37.45, 41.29, 41.75, 59.48, 66.31-67.00, 69.26, 69.34, 168.04. $^{31}$P NMR (d$_6$-DMSO, ppm): δ –1.19, –1.43. DSC: T$_g$=–54.7° C. TGA in N$_2$: 115-180° C., 11% mass loss; 180-270° C., 38% mass loss, 270-600° C., 21% mass loss, 30% mass remaining above 600° C. IR: 3300-2480, 2390-2280, 1739, 1629, 1462, 1381, 1253, 1017, 967, 801 cm$^{-1}$.

Self-Assembly of Functional Diblock Copolymers.

The functional diblock copolymers (5.0 mg) were suspended into nanopure water (1.0 mL) and sonicated for 10 min.

Cytotoxicity Assays.

RAW 264.7 mouse macrophages (2×10$^4$ cells/well) were plated in a 96-well plate in Dulbecco's Modified Eagle Medium (DMEM) (10% fetal bovine serum and 1% penicillin/streptomycin). Cells were incubated at 37° C. in a humidified atmosphere containing 5% CO$_2$ for 24 h to adhere. Then, the medium was replaced with a fresh medium 1-h prior to the addition of 20 µL of the various micellar formulations to 100 µL of the medium (final concentrations ranged from 5-to-3000 µg/mL). The cytotoxicity of Lipofectamine® 2000 (Invitrogen, Grand Island, N.Y.) was also tested at final concentrations ranging from 1-to-160 µg/mL using the same procedures. The cells were incubated with the formulations for 24 h and washed once with phosphate-buffered saline (PBS) and 100 µL of the complete media was added to the cells. The MTS combined reagent (20 µL) was added to each well (Cell Titer 96® Aqueous Non-Radioactive Cell Proliferation Assay, Promega Co., Madison, Wis.). The cells were incubated with the reagent for 2 h at 37° C. in a humidified atmosphere containing 5% CO$_2$ protected from light. Absorbance was measured at 490 nm using SpectraMax M5 (Molecular Devices Co., Sunnyvale, Calif.). The cell viability was calculated based on the relative absorbance to the control-untreated cells. The 0% and 100% cell viabilities were considered as the control medium (no cells) and cells with no treatment, respectively. The calculations of the IC$_{50}$ values were performed using GraphPad Prism four-parameter fit (GraphPad Software, Inc., La Jolla, Calif.).

Results and Discussion:

Rapid and facile construction of diverse nanostructures is demonstrated starting from the simple syntheses of functional cyclic phospholane monomers and continuing at each stage through polymerization, chemical modification and supramolecular assembly steps. Ultrafast (<5 min) one-pot sequential polymerization of two different cyclic phospholane monomers produced a single hydrophobic-functional AB diblock polyphosphoester, having reactive alkynyl side-chain chemical functionalities within only the B block segment. After its rapid (<1 h) purification by precipitation and centrifugation, a series of thiol-yne chemical transformations produced four different functionalized diblock copolymers, which were then assembled by direct dissolution into water to afford four different polymeric micelles with tunable surface properties.

Monomer Design and Synthesis.

Polyphosphoesters can be prepared by ring-opening polymerization (ROP),[18] polycondensation,[19] transesterification,[20] and enzymatic polymerization.[21] Among all of these methods, the ROP of cyclic phospholane monomers by using metal compounds as initiators or polymerization catalysts, is a well-established process to provide linear or hyperbranched polyphosphoesters[22] with predictable molecular weight, narrow molecular weight distribution, and well-defined chain ends.[23] Recently, Iwasaki et al. first reported using 1,8-diazabicyclo[5.4.0]undec-7-ene (DBU) or 1,5,7-triazabicyclo[4.4.0]dec-5-ene (TBD) as organocatalysts to promote ROP of cyclic phospholanes.[24] To eliminate using environmentally-sensitive metal compounds, and better fulfill the requirements of biomedical applications, many groups have adopted the organocatalyzed ROP of phospholanes to prepare polyphosphoesters for biomaterials. See, e.g., Zhang, S.; Li, A.; Zou, J.; Lin, L. Y.; Wooley, K. L. ACS. Macro. Lett. 2012, 1, 328; Liu, J.; Pang, Y.; Huang, W.; Zhai, X.; Zhu, X.; Zhou, Y.; Yan, D. Macromolecules 2010, 43, 8416; Zhai, X.; Huang, W.; Liu, J.; Pang, Y.; Zhu, X.; Zhou, Y.; Yan, D. Macromol. Biosci. 2011, 11, 1603; Yuan, Y.; Du, J.; Wang, J. Chem. Commun. 2012, 48, 570; Clement, B.; Grignard, B.; Koole, L.; Jerome, C.; Lecomte, P. Macromolecules 2012, 45, 4476; Du, J.; Du, X.; Mao, C.; Wang, J. J. Am. Chem. Soc. 2011, 133, 17560.

Two phospholane monomers were required for our design: one having a reactive chemical functionality that would be stable during polymerization and then readily available for chemical modification, and the second providing hydrophobicity, ultimately to lead to amphiphilic block copolymers for assembly of nanostructures. Cyclic phospholane monomers are usually prepared from the condensation of 2-chloro-2-oxo-1,3,2-dioxaphospholane (COP) and an alcohol.

A variety of functional cyclic phospholane monomers have been reported, including methyl, ethyl, isopropyl, PEGylated, hydroxyl-functionalized, protected hydroxyl-functionalized, protected amino-functionalized, protected thiol-functionalized, acrylate-functionalized, methacrylate-functionalized, alkyne-functionalized and alkene-functionalized. See, e.g., Wang, Y.; Li, Y.; Yang, X.; Yuan, Y.; Yan, L.; Wang, J. Macromolecules 2009, 42, 3026; Iwasaki, Y.; Wachiralarpphaithoon, C.; Akiyoshi, K. Macromolecules 2007, 40, 8136; Iwasaki, Y.; Nakagawa, C.; Ohtomi, M.; Ishihara, K.; Akiyoshi, K. Biomacromolecules 2004, 5, 1110; Du, J.; Chen, D.; Wang, Y.; Xiao, C.; Lu, Y.; Wang, J.; Zhang, G. Biomacromolecules 2006, 7, 1898; Zhu, W.; Sun, S.; Xu, N.; Gou, P.; Shen, Z. J. Appl. Polym. Sci. 2012, 123, 365; Liu, J.; Huang, W.; Pang, Y.; Zhu, X.; Zhou, Y.; Yan, D. Biomaterials 2010, 31, 5643; Song, W.; Du, J.; Liu, N.; Dou, S.; Cheng, J.; Wang, J. Macromolecules 2008, 41, 6935; Sun, T.; Du, J.; Yan, L.; Mao, H.; Wang, J. Biomaterials 2008, 29, 4348; Sun, T.; Du, J.; Yao, Y.; Mao, C.; Dou, S.; Huang, S.; Zhang, P.; Leong, K. W.; Song, E. W.; Wang, J. ACS Nano 2011, 5, 1483; Wang, Y.; Li, Y.; Sun, T.; Xiong, M.; Wu, J.; Yang, Y.; Wang, J. Macromol. Rapid. Comm. 2010, 31, 1201; Shao, H.; Zhang, M.; He, J.; Ni, P. Polymer 2012, 53, 2854; Wachiralarpphaithoon, C.; Iwasaki, Y.; Akiyoshi, K. Biomaterials 2007, 28, 984; Zhang, S.; Li, A.; Zou, J.; Lin, L. Y.; Wooley, K. L. ACS. Macro. Lett. 2012, 1, 328; Clement, B.; Grignard, B.; Koole, L.; Jerome, C.; Lecomte, P. Macromolecules 2012, 45, 4476; Du, J.; Du, X.; Mao, C.; Wang, J. J. Am. Chem. Soc. 2011, 133, 17560.

The ring opening polymerization (ROP) of those functional monomers produced corresponding high molecular weight functional polyphosphoesters. Our group recently developed a stable alkyne-functionalized cyclic phospholane monomer and studied its polymerization kinetics under an organocatalyst, in addition to the chemical functionalization of this alkyne-functionalized polyphosphoester by "click" type azide-alkyne Huisgen cycloaddition and thiol-yne reaction.[17] This butyryl phospholane (BYP, 1) monomer was, therefore, used to incorporate side-chain chemical functionality along the backbone of one segment of the AB block copolymer of this study, to allow for the versatile platform development.

A challenge associated with identification of the second phospholane monomer, for production of a hydrophobic polyphosphoester chain segment that could be utilized to drive supramolecular assembly into nanostructures in water, is related to the high water solubility of the polyphosphoester backbone. The hydrophobicity of the polyphosphoester system can be tuned by changing the alkyl side chains of the monomer or by copolymerizing monomers with different alkyl side chains, but the water solubility of alkyl-substituted polyphosphoesters has been typically observed to be temperature dependent. See Wang, Y.; Li, Y.; Yang, X.; Yuan, Y.; Yan, L.; Wang, J. Macromolecules 2009, 42, 3026; Iwasaki, Y.; Wachiralarpphaithoon, C.; Akiyoshi, K. Macromolecules 2007, 40, 8136. For instance, a hydrophobic monomer, 2-isopropoxy-2-oxo-1,3,2-dioxaphospholane, produced an isopropyl-functionalized polyphosphoester that exhibited a lower critical solution temperature (LCST), and when incorporated into a diblock copolymer, poly(ethylene glycol)-block-poly(2-isopropoxy-2-oxo-1,3,2-dioxaphospholane), served as a hydrophobic domain of an amphiphilic core-shell morphological nanoparticle only at temperatures above its LCST. See Zhai, X.; Huang, W.; Liu, J.; Pang, Y.; Zhu, X.; Zhou, Y.; Yan, D. Macromol. Biosci. 2011, 11, 1603; Wang, Y.; Tang, L.; Li, Y.; Wang, J. Biomacromolecules 2009, 10, 66. To achieve a polyphosphoester with high hydrophobicity over a wide temperature range, we attempted to couple COP with several alcohols with long or bulky alkyl groups. A tertiary alcohol, tert-butanol, was employed to react with COP, but the product monomer decomposed in the reaction mixture. The cyclic phospholane monomer from the coupling of a secondary alcohol, 3-pentanol, and COP also decomposed upon heating during vacuum distillation. The boiling point of 1-decanol and that of the resulting monomer were too similar to allow for good purification. To avoid the poor purification abilities, 2-ethyl-1-butanol was chosen to functionalize COP because of its relatively bulky hydrophobic alkyl group. Finally, the monomer, 2-ethylbutyl phospholane (EBP, 2), was obtained through the one-step esterification of two commercially-available compounds, 2-ethyl-1-butanol and COP followed by simple filtration and vacuum distillation (see FIG. 20).

Polymerization results of 2 with DBU and TBD under different conditions are provided in Table 4. Concentrations for all entries were 1 g monomer (M) per 1 mL dichloromethane. Initiator (I) was benzyl alcohol for all entries. $M_n$ (GPC) and $M_w/M_n$ (GPC) were measured by DMF GPC calibrated using polystyrene standards. $M_n$ (Theor) was calculated from the monomer to initiator ratio and corrected for conversion. $M_n$ ($^1$H NMR) was calculated from the monomer to initiator ratio based on $^1$H NMR of final polymer product.

TABLE 4

| entry | Catalyst | M:I:Catalyst (molar ratios) | Temp | Time (min) | Conversion ($^{31}$P NMR) | $M_n$, Da (GPC) | $M_w/M_n$ (GPC) | $M_n$, Da (Theor) | $M_n$, Da ($^1$H NMR) |
|---|---|---|---|---|---|---|---|---|---|
| 1 | DBU | 25:1:1.5 | RT | 15 | 51% | 5600 | 1.31 | 2700 | 3000 |
| 2 | DBU | 50:1:1.5 | RT | 30 | 43% | 6700 | 1.34 | 5600 | 5200 |
| 3 | DBU | 100:1:1.5 | RT | 60 | 32% | 8300 | 1.42 | 6800 | 7100 |
| 4 | TBD | 25:1:1.5 | 0° C. | 1 | 99% | 7100 | 1.14 | 5300 | 5600 |
| 5 | TBD | 50:1:1.5 | 0° C. | 2 | 100% | 10300 | 1.14 | 10400 | 11000 |
| 6 | TBD | 100:1:1.5 | 0° C. | 4 | 99% | 17200 | 1.16 | 21000 | 20500 |

Homopolymerization of EBP by Organocatalysts.

The polymerization behavior of 2 with organocatalysts DBU or TBD was studied (Table 4). The polymerizations of 2 upon addition of DBU (entries 1-3 in Table 4) were conducted at room temperature to allow the direct comparison to our published polymerization results of BYP. See Zhang, S.; Li, A.; Zou, J.; Lin, L. Y.; Wooley, K. L. ACS. Macro. Lett. 2012, 1, 328. In our previous report, the conversion of 1 reached 99% in 10 min with different ratios of monomer-to-initiator. In contrast, the conversion of 2 did not reach 60% even over a period of 1 h under the same conditions, which suggested that the reactivity of 2 is much lower than that of 1, potentially because of the sterically-bulky side chain. Also, DBU gave poor control over the molecular weight distribution (PDI>1.30) for the polymerization of 2. When TBD was used as a catalyst instead of DBU, the polymerization of 2 proceeded to 99% conversion in less than 5 min at 0° C. (entries 4-6 in Table 4). The dual activation of TBD, simultaneously serving as a hydrogen-bond donor to the monomer via the N—H site and also as a hydrogen-bond acceptor to the hydroxyl proton of the propagating alcohol, explains the significant increase in the polymerization rate.[27] When the polymerization of 2 with TBD was quenched by acetic acid upon the completion of the reaction, good control over the molecular weight distribution (PDI<1.20) could be achieved. Therefore, well-defined poly(2-ethylbutyl phospholane) (PEBP, 3) with predictable molecular weight could be synthesized by using TBD as a catalyst.

One-Pot Sequential ROP.

To prepare diblock polyphospohoester, we first attempted to polymerize 1 and then 2 by using TBD or DBU as a catalyst and benzyl alcohol as an initiator. After the complete conversion of the first monomer 1, the second monomer 2 was added into the reaction mixture. However, there was no conversion of 2 (monitored by $^{31}$P NMR) and no chain extension (characterized by DMF GPC). We speculated that TBD or DBU associated with poly(butynyl phospholane) (PBYP) or residual 1, predominately, over 2, due to the bulky side chain of 2. Therefore, when 1, PBYB, and catalyst (TBD or DBU) were all present in the reaction mixture neither catalyst was able to successfully promote the ROP of 2 to achieve chain extension.

Successful chain extension was achieved and poly(2-ethylbutyl phospholane)$_{50}$-b-poly(butynyl phospholane)$_{50}$ (PEBP$_{50}$-b-PBYP$_{50}$, 4) was synthesized after the addition order of the two monomers in the sequential polymerization was reversed (See FIG. 21). The less reactive monomer, 2, was first polymerized at relatively high concentration in dichloromethane with TBD as a catalyst and benzyl alcohol as an initiator at 0° C. After complete conversion of 2 (monitored by $^{31}$P NMR) in 2 min, the more reactive monomer, 1, was transferred into the reaction mixture for the chain extension. Over 99% conversion of 1 was reached quickly (in 1 min), however GPC analysis of the diblock polymer showed poor control over the molecular weight distribution and the possibility of transesterification. To decrease the polymerization rate as well as the possibility of transesterification, the second step of sequential polymerizations was conducted at lower monomer concentration and −20° C. by diluting and cooling the reaction mixture before the second monomer was added. A two minute polymerization of 2 at 0° C. and 3 mol/L monomer concentration and the sequential one minute polymerization of 1 at −20° C. and 1 mol/L monomer concentration provided over 99% conversion of each monomer in the individual steps and retained a narrow molecular weight distribution with a PDI of 1.17 for the diblock polyphospohoester (FIG. 22). The diblock copolymer 4 was easily purified by precipitation from dichloromethane or acetone into a pentane and diethyl ether mixture (3:1 vol ratio) followed by centrifugation.

This facile polymerization provided a strategy to prepare diblock polyphosphoester with precise structural control in an atom-efficient synthesis manner. See Ober, C. K.; Cheng, S. Z. D.; Hammond, P. T.; Muthukumar, M.; Reichmanis, E.; Wooley, K. L.; Lodge, T. P. Macromolecules 2009, 42, 465. Confirmation of the diblock composition was made by $^{31}$P NMR spectroscopy of the purified polymer, which displayed two signals at −1.19 and −1.83 ppm that were assigned to the two $^{31}$P environments in the PEBP and PBYP blocks, respectively (FIG. 23). $^1$H NMR also showed full retention of the alkyne group of the functional PBYP block and alkyl group in hydrophobic PEBP block. The sequential polymerization of two monomers in a one-pot method at multigram scale was completed in less than 5 min, and the 3 precipitations and centrifugations could be accomplished in less than 1 hour. The ultrafast one-pot sequential synthesis of a well-defined diblock polyphosphoester, is more advantageous than the chain extension from purified macro-initiator, which requires the complete removal of acetic acid used for quenching the first polymerization step. See Clément, B.; Grignard, B.; Koole, L.; Jérôme, C.; Lecomte, P. Macromolecules 2012, 45, 4476.

Functionalization by Thiol-yne Reactions.

The hydrophobic-functional AB diblock polyphosphoester, 4, was then functionalized into four amphiphilic diblock polyphosphoesters by "click" type thiol-yne reaction with thiol-containing molecules including 2-(2'-methoxyethoxy)ethanethiol, 3-mercaptopropionoic acid, cysteamine hydrochloride and 1-cysteine hydrochloride monohydrate (FIG. 5A). Radical-mediated thiol-yne chemistry, a "click" type reaction, is a robust and versatile method that tolerates a variety of functional groups, such as carboxylic acids and amines, to densely functionalize alkynyl groups. See Hoyle, C. E.; Lowe, A. B.; Bowman, C. N. Chem. Soc. Rev. 2010, 39, 1355. In our previous report, we demonstrated that the radical-mediated thiol-yne reaction was compatible with the polyphosphoester backbone without causing any coupling or crosslinking See Zhang, S.; Li, A.; Zou, J.; Lin, L. Y.; Wooley, K. L. ACS. Macro. Lett. 2012, 1, 328. Ten equivalents of thiols to alkyne groups were used in the radical reaction to avoid chain-chain coupling, while two hours exposure to UV irradiation with DMPA as the photo-initiator ensured complete conversion.

Each functionalized diblock copolymer was readily purified and its structure was confirmed. Given the use of ten-fold excess amounts of the thiols, the conditions employed for purification were defined by and their physical characteristics. The non-ionic diblock, 5, and anionic diblock, 6, could be purified by direct precipitation from methanol or acetone into a pentane and diethyl ether (3:1 vol ratio) three times and dried under vacuum. However, the salt-based thiols required that the cationic diblock, 7, and zwitterionic diblock, 8, were purified by dialysis against a pH 3.0 HCl solution, an acidic condition to ensure the amine group was protonated, in the cold room (4-8° C.) for 2 days and then lyophilized. The disappearance of terminal acetylene protons (2.18-2.04 ppm) in the $^1$H NMR spectra of the four product polymers confirmed the full consumption of the alkyne groups. The diastereotopic splitting of the methylene protons (1.76-1.92, 2.31-2.47 ppm), corresponding to the 1,2-regioselectivity of thiol-yne chemistry, and the presence of other functional groups also verified the successful installation of the four different thiols onto 4. The thiol-yne reaction was demonstrated to efficiently transform the hydrophobic-functional AB diblock polyphosphoester into four different kinds of amphiphilic polyphosphoesters.

Self-Assembly of Amphiphilic Polyphosphoesters.

All four amphiphilic polyphosphoesters were dissolved in nanopure water by sonication for 5 min at room temperature and spontaneously formed spherical nanoparticles, 9, 10, 11 and 12, with narrow size distributions (FIG. 24). The glass transition temperatures ($T_g$) were far below room temperature (−50° C.) so that all polymer chain segments, whether hydrophilic or hydrophobic, had sufficient mobility and were able to undergo rapid relaxation or extension in response to the varied electrostatic interactions to self-organize into micellar structures with core-shell morphology easily. In the nanoparticle assemblies, it is expected that the hydrophobic PEBP block aggregated in the particle core, and was shielded from the aqueous medium by the shell region consisting of functionalized PBYP blocks, due to the highly hydrophilic nature of the oligo(ethylene glycol), carboxyl, and amino group.

The morphological influence of varying PBYP block functionalities on the aqueous self-assembled nanoparticles was characterized by both transmission electron microscopy (TEM) and dynamic light scattering (DLS). Bright-field TEM images of 9, 10, 11 and 12 prepared in nanopure water showed uniform particles with average sizes of approximately 15, 18, 18 and 23 nm, respectively (FIG. 25a, 25b, 25c, 25d). Due to the collapsing of swelled hydrophilic block chains during dry TEM sample preparation, the core-shell architecture was not directly observed. DLS results showed mono-modal size distribution of particles in all four aqueous assembly samples. The number-average hydrodynamic diameter values ($D_h$(number)) of 9, 10, 11 and 12 were 13±3 nm, 16±3 nm, 16±3 nm and 21±4 nm, respectively (FIG. 3e, 3f, 3g, 3h). Due to differences in the hydrophilic-hydrophobic balance and potential repulsive effects within and between hydrophilic chains with the same micellar assemblies, those constructed from the anionic- (6) or cationic- (7) functionalized PBYP chains were of slightly increased particle sizes than the non-ionic (5) functionalized PBYP chains, as measured by both TEM and DLS results. Zwitterionic functionalized polymer 8 assembled into particles with the largest particle size, however, all of the particle sizes were similar. It is remarkable that such uniform particle size distributions were produced by a simple, rapid, direct dissolution of the bulk block copolymer samples into nanopure water or buffer solutions.

Surface Charges of the Micelle Systems.

The surface charge densities, measured as zeta potential values, were characterized for the resulting micelles in pH 5.0 and pH 7.4 buffer solutions by Delsa Nano C particle analyzer (FIG. 25). Non-ionic micelles, 9, were slightly negatively-charged with zeta potentials of −12.2 mV at pH 7.4 and −18.0 at pH 5.0, which is common for neutral polymer nanoparticles, including those based on polyphosphoesters. See, e.g., Xiong, M.; Bao, Y.; Yang, X.; Wang, Y.; Sun, B.; Wang, J. J. Am. Chem. Soc. 2012, 134, 4355; Song, W.; Du, J.; Liu, N.; Dou, S.; Cheng, J.; Wang, J. Macromolecules 2008, 41, 6935. The anionic and cationic characteristics of micelles formed from 10 and 11 were confirmed through zeta potential measurements. The anionic micelles were more negatively charged at pH 7.4 than at pH 5.0 due to the higher degree of deprotonation of carboxylic groups at pH 7.4 than at pH 5.0. Similarly, because of a higher extent of protonation of amino groups at pH 5.0 than at pH 7.4, the cationic micelles were more positively charged at pH 5.0 than at pH 7.4. In the case of the zwitterionic micelles, the positive charge of amino groups and the negative charge of carboxylic groups counteracted each other, which resulted in almost neutral micelles at both pH 5.0 and 7.4, with zeta potentials of −5.2 and −8.1 mV, respectively.

Cytotoxicity of Micellar Systems.

To understand the surface charge-dependent cytotoxicity of the polymeric micelles, we tested four micelles against RAW 264.7 mouse macrophages. The surface chemistries of nanoparticles play a dominant role in determining their fate both in vitro and in vivo. See Elsabahy, M.; Wooley, K. L. Chem. Soc. Rev. 2012, 41, 2545; Albanese, A.; Tang, P. S.; Chan, W. C. W. Annu Rev Biomed Eng. 2012, 14, 1. Although it is easier to control the surface charge of inorganic nanoparticles (see Goodman, C. M.; McCusker, C. D.; Yilmaz, T.; Rotello, V. M. Bioconjugate Chem. 2004, 15, 897; Arvizo, R. R.; Miranda, O. R.; Thompson, M. A.; Pabelick, C. M.; Bhattacharya, R.; Robertson, J. D.; Rotello, V. M.; Prakash, Y. S.; Mukherjee, P. Nano. Lett. 2010, 10, 2543; Walkey, C. D.; Olsen, J. B.; Guo, H. B.; Emili, A.; Chan, W. C. W. J. Am. Chem. Soc. 2012, 134, 2139), there is a limited understanding of the correlation between the cytotoxicity and the surface properties of polymeric micelles, due to the difficulty of preparing polymeric micelles with different surface charges and functionalities, while maintaining similar particle sizes. The micellar systems developed in this study had the same polymer backbone, similar sizes and size distribution characteristics (FIG. 24), with various side chain functionalities that resulted in micellar nanoparticles with various surface charges, which allowed for direct comparison of their biological properties.

Four micelles, 9, 10, 11 and 12 were tested for their cytotoxicity in RAW 264.7 mouse macrophages at different concentrations (FIG. 26). No cytotoxicity was observed for the non-ionic, zwitterionic and anionic micelles at the range of the tested concentrations (5-to-3000 µg/mL after 24 h-incubation), except for the highest tested concentration of the anionic micelles. On the contrary, the cationic micelles showed a dose-dependent toxicity, which is in accordance with the known cytotoxicity of cationic nanoparticles, due to the interactions with the negatively-charged cell membranes. As the cationic micelles may have potential applications as transfection reagents and nucleic acids-delivery carriers, their cytotoxicity was compared with that of Lipofectamine®, a commercially-available cationic transfection agent. The $IC_{50}$ value of the cationic micelles was 180±48 µg/mL, while that of Lipofectamine® was 31±6 µg/mL. The approximately 6-fold lower cytotoxicity for the polyphosphoester-based cationic nanoparticles may result from the degradability or the surface characteristics of the system, and may provide an alternative cationic carrier with better biocompatibility. See Wang, J.; Mao, H.; Leong, K. W. J Am Chem Soc 2001, 123, 9480.

Conclusion:

In this study, a retrosynthetic methodology has been used to develop a versatile platform for the construction of a family of polymeric micelles with varying surface charges and functionalities based on biodegradable polyphosphoesters. In this strategy, all steps of the entire engineering process, from small molecule chemistry to nanoparticle assembly, were equipped with "click" type advantageous features, such as quantitative conversion, rapid reaction, mild conditions, high functional group tolerance, with an absence of byproducts and side reactions. The construction of the polymeric micelle system began from the preparation of hydrophobic and alkyne-functionalized monomers, continued through their polymerization, followed by chemical modification and finally involved supramolecular assembly by direct addition of water. To overcome the hydrophilic nature of the polyphosphoester backbone, a hydrophobic monomer (2-ethylbutyl phospholane), was synthesized and its polymerization activity under two organocatalysts was evaluated through the comparison with that of an alkyne-functionalized monomer butynyl phospholane. By taking advantage of the reactivity difference of the two monomers, the well-defined AB diblock polyphosphoester containing a hydrophobic block and a functional block was synthesized by an ultrafast ring-opening polymerization in a one-pot sequential manner. The clickable alkynyl groups on the functional portion of the hydrophobic-functional AB diblock polyphosphoester were transformed with four different thiols by photo-initiated, radical-mediated thiol-yne chemistry, forming four amphiphilic diblock polyphosphoesters with different charge types. Those non-ionic, anionic, cationic and zwitterionic amphiphilic diblock polyphosphoesters underwent self assembly in water by direct dissolution and sonication to afford uniform spherical micelles with average sizes of ca. 15, 18, 18 and 23 nm (by TEM), respectively. The surface charges of those four micelles were found to coincide with the presence of their respective chemical functional groups. The micelles have also shown high biocompatibility, and even the cationic micelles had a 6-fold lower cytotoxicity when compared to Lipofectamine®, a commercial transfection agent. Currently, this degradable nanoparticle family is being applied to various bio-applications.

Example 4

Azide Alkyne Huisgen Cycloaddition of PEBP-b-PBYP with α-methoxy-ω-azido PEG

FIG. 31 illustrates a reaction scheme for Azide Alkyne Huisgen Cycloaddition of PEBP-b-PBYP with α-methoxy-ω-azido PEG. In a typical experiment, a dried vial containing a magnetic stir bar was charged with PEBP-b-PBYP (0.89 g, 46 µmol, 1 equiv), α-methoxy-ω-azido PEG (0.36 g, 0.18 µmol, 4 eq.), N,N,N',N',N''-pentamethyldiethylenetriamine (PMDETA, 13 mg, 74 mmol, 1.6 eq.) and 7 mL of DMF. The reaction mixture was degassed by several freeze-pump-thaw cycles (N>3), during which copper(I) bromide (5.3 mg, 37 mmol, 0.8 equiv.) was added. The flask was allowed to return to room temperature after the final cycle and stirred for another 4 hours. The solution was subsequently filtered through a neutral alumina column and dialysized against Chelex 100 resin in nanopure water in presoaked dialysis tubing (MWCO. ca. 6-8 kDa) for 2 days to remove copper ions, followed by lyophilization to yield white powder with a 72% yield. Inductively coupled plasma-mass spectrometry (ICP-MS) confirmed that ca. 10 ppm of copper was present in the polymer. $^1$H NMR (CDCl$_3$, ppm): δ 0.89 (t, J=7.4 Hz, POCH$_2$CH(CH$_2$CH$_3$)$_2$), 1.36 (m, POCH$_2$CH(CH$_2$CH$_3$)$_2$), 1.50 (m, POCH$_2$CH), 2.05-2.24 (b, POCH$_2$CH$_2$C≡CH), 2.56-2.65 (b, POCH$_2$CH$_2$C≡CH), 3.12 (m, NCH$_2$CH$_2$), 3.37 (s, OCH$_3$), 3.63 (s, OCH$_2$CH$_2$), 3.96-4.02 (t, J=5.6 Hz, POCH$_2$CH), 4.14-4.39 (br, POCH2CH2, POCH2CH2OP), 5.07 (d, J=8.3 Hz, OCH$_2$Ar), 7.31-7.40 (m, Ar—H), 7.63 (m, CH$_2$CH$_2$CCHNCH$_2$). $^{13}$C NMR (CDCl$_3$, ppm): δ 11.03, 20.72, 22.79, 41.60, 65.52-67.15, 70.13, 70.68, 70.95, 79.72, 128.06, 128.73. $^{31}$P NMR (CDCl$_3$, ppm): δ −0.99, −1.64. GPC: $M_n$=21800 g/mol, PDI=1.24. DSC: $T_g$=−36.2° C., −18.6° C.; $T_m$=45.8° C. TGA in N$_2$: 140-270° C., 40% mass loss; 270-360° C., 35% mass loss, 360-600° C., 3% mass loss, 22% mass remaining above 600° C. IR (cm$^{-1}$): 3700-3100, 3050-2800, 166, 1465, 1342, 1275, 1109, 1016, 962, 841, 808 cm$^{-1}$.

Preparation of Shell Crosslinked (SCK) Nanoparticles from PEBP-b-(PBYP-g-PEG).

In a typical experiment, 30 mg polymers PEBP-b-(PBYP-g-PEG) were dissolved in 15.0 mL methanol in a 100 mL flask and allowed to stir for 30 min at room temperature. To this solution, 15.0 mL nanopure water was added dropwise via a syringe pump over a period of 4 min. The mixture was allowed to stir another 30 min at room temperature and bubbled with nitrogen. To the micelle solution was added a solution of hexa(ethylene glycol) dithiol (3.5 mg, 0.1 eq., with respect to alkyne, nominal 20% crosslinking) in 1:1 methanol/nanopure water mixture, 2,2-dimethoxy-2-phenylacetophenone (DMPA, 2.9 mg, eq., with respect to alkyne residues). The resulting mixture was placed under UV lamp with an irradiation at 365 nm for 3 hours before dialysis against nanopure water for 2 days in presoaked dialysis tubing (MWCO. ca. 6-8 kDa), and then lyophilized to yield yellowish powder with a 87% yield.

PTX Loading into PEBP-b-(PBYP-g-PEG) Micelles/SCKs.

In a typical experiment, to a vial containing 4.5 mL polymer/SCKs ethanol solution (polymer concentration: 4.0 mg/mL), a solution of PTX (2.0 mg/mL in ethanol, 10 wt %) was added. The vial was shaken vigorously to mix the solution, and then ethanol was completely removed in vacuo. Subsequently, 2 mL of nanopure water was added to the vial to resuspend the micelles/SCKs and PTX mixture. After sonication for 5 min, a well dispersed nanoparticles suspension was obtained. DLS and TEM were used to characterize these PTX-loaded nanoparticles, and HPLC was used to confirm the actual loading amount of PTX. Loading efficiency is provided in Table 5.

TABLE 5

| Sample name | Polymer conc. (mg/mL) | Theoretical PTX conc. (ug/mL) | Actual PTX conc. by HPLC (μg/mL) | Stability |
| --- | --- | --- | --- | --- |
| Micelles-10%-A | 9.0 | 1000 | 1039 | Stable over 1 month at 6° C. |
| Micelles-10%-B | 13.5 | 1500 | 1509 | Stable over 1 month at 6° C. |
| Micelles-10%-C | 18.0 | 2000 | 2043 | Stable over 1 month at 6° C. |
| Micelles-10%-D | 45.0 | 5000 | 4818 | Stable over 1 month at 6° C. |
| Micelles-15% | 8.5 | 1500 | 1487 | Precipitated after 2 days |
| Micelles-20% | 32.0 | 800 | — | Precipitated after 2 days |
| SCKs-10%-A | 9.0 | 1000 | 977 | Stable over 1 month at 6° C. |
| SCKs-10%-B | 18.0 | 2000 | 1963 | Stable over 1 month at 6° C. |
| SCKs-10%-C | 45.0 | 5000 | 4948 | Stable over 1 month at 6° C. |

Table 6 provides in vitro toxicity results.

TABLE 6

| Formulation | IC50 (μM) | |
| --- | --- | --- |
| | OVCAR-3 | RAW 264.7 |
| Taxol | 0.005 ± 0.002 | 0.04 ± 0.01 |
| PTX-loaded Micelles | 0.015 ± 0.010 | 0.10 ± 0.04 |
| PTX-loaded SCKs | 0.010 ± 0.008 | 0.08 ± 0.02 |

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A composition comprising:
   an amphiphilic block copolymer derived from poly(ethylbutyl phospholane)-block-poly (butynyl phospholane) (PEBP-b-PBYP) by modifying from poly(ethylbutyl phospholane)-block-poly (butynyl phospholane) (PEBP-b-PBYP) with a functionality comprising an anionic, cationic, zwitterionic, or neutral moiety or a combination thereof, the amphiphilic block copolymer comprising a hydrophobic-functional AB diblock polyphosphoester comprising at least one degradable polyphosphoester block; and
   a chemotherapeutic agent.

2. The composition of claim 1, wherein the amphiphilic block copolymer comprises a polymer backbone and the chemotherapeutic agent is conjugated with the copolymer along a selective region of the polymer backbone.

3. The composition of claim 1, further comprising a pendant compound selected from the following group: a dye, an imaging agent, and a hydrophilic polymer, wherein the pendant compound is chemically reacted with the polyphosphoester via the reactive side chain functionality of the polyphosphoester.

4. The composition of claim 1, wherein the block copolymer encapsulates the chemotherapeutic agent.

5. The composition of claim 1, wherein the chemotherapeutic agent comprises paclitaxel (PTX).

6. A composition of comprising:
   a poly(ethylbutyl phospholane)-block-poly (butynyl phospholane)-graft-polyethylene glycol (PEBP-b-PBYP-g-PEG) amphiphilic block copolymer; and
   a chemotherapeutic agent.

7. The composition of claim 6, wherein the amphiphilic block copolymer comprises a polymer backbone and the chemotherapeutic agent is conjugated with the copolymer along a selective region of the polymer backbone.

8. The composition of claim 6, wherein the block copolymer encapsulates the chemotherapeutic agent.

9. The composition of claim 6, wherein the chemotherapeutic agent comprises paclitaxel (PTX).

10. The composition of claim 6, further comprising a pendant compound selected from the following group: a dye, an imaging agent, and a hydrophilic polymer, wherein the pendant compound is chemically reacted with the polyphosphoester via the reactive side chain functionality of the polyphosphoester.

* * * * *